(12) United States Patent
Goto et al.

(10) Patent No.: US 8,053,604 B2
(45) Date of Patent: *Nov. 8, 2011

(54) PROCESS FOR PREPARATION OF DIPHOSPHINE COMPOUNDS AND INTERMEDIATES FOR THE PROCESS

(75) Inventors: Mitsutaka Goto, Osaka (JP); Mitsuhisa Yamano, Nishinomiya (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 12/694,658

(22) Filed: Jan. 27, 2010

(65) Prior Publication Data

US 2010/0125153 A1  May 20, 2010

Related U.S. Application Data

(62) Division of application No. 11/682,630, filed on Mar. 6, 2007, now Pat. No. 7,678,942, which is a division of application No. 10/497,808, filed as application No. PCT/JP02/12758 on Dec. 5, 2002, now Pat. No. 7,208,633.

(30) Foreign Application Priority Data

Dec. 7, 2001  (JP) .................................. 2001-374909

(51) Int. Cl.
C07F 5/02 (2006.01)
C07F 9/50 (2006.01)
(52) U.S. Cl. ............................................. 568/2; 568/17
(58) Field of Classification Search .................. None
See application file for complete search history.

(56) References Cited

U.S. PATENT DOCUMENTS 2,926,194 A    2/1960   Burg et al.

FOREIGN PATENT DOCUMENTS

WO    98/42716    1/1998

OTHER PUBLICATIONS

Ager, D., et al., "Convenient and Direct Preparation of Tertiary Phosphines via Nickel-Catalysed Cross-Coupling", Chem. Commun., (1997), pp. 2359-2360.

(Continued)

*Primary Examiner* — Daniel Sullivan
*Assistant Examiner* — Yevegeny Valenrod
(74) *Attorney, Agent, or Firm* — Wenderoth, Lind & Ponack, L.L.P.

(57) ABSTRACT

A production method of a compound represented by the formula

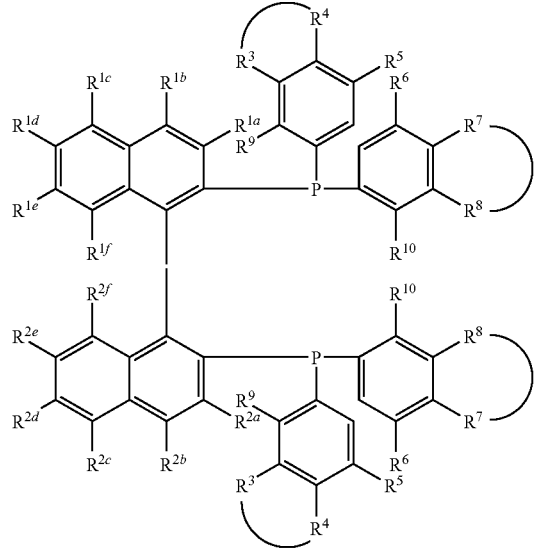

wherein $R^{1a}$, $R^{1b}$, $R^{1c}$, $R^{1d}$, $R^{1e}$, $R^{1f}$, $R^{2a}$, $R^{2b}$, $R^{2c}$, $R^{2d}$, $R^{2e}$ and $R^{2f}$ are the same or different and each is a hydrogen atom and the like, and $R^3$, $R^4$, $R^5$, $R^6$, $R^7$, $R^8$, $R^9$ and $R^{10}$ are the same or different and each is a hydrogen atom and the like, or a salt thereof, which comprises reacting a compound represented by the formula

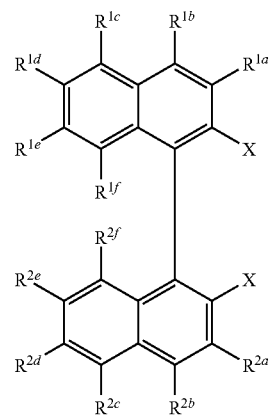

wherein X is a leaving group and other symbols are as defined above, or a salt thereof, with a phosphine-borane complex represented by the formula

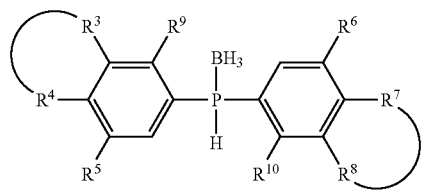

wherein the symbols are as defined above, or a salt thereof, in a solvent in the presence of an amine and a nickel catalyst, is provided.

2 Claims, No Drawings

U.S. PATENT DOCUMENTS

| | | | |
|---|---|---|---|
| 5,399,771 | A | 3/1995 | Cai et al. |
| 5,808,162 | A | 9/1998 | Sayo et al. |
| 5,874,628 | A | 2/1999 | Laneman et al. |
| 7,135,582 | B2 | 11/2006 | Goto et al. |
| 7,678,942 | B2 * | 3/2010 | Goto et al. ............... 568/2 |

FOREIGN PATENT DOCUMENTS

| | | |
|---|---|---|
| EP | 0 754 696 | 1/1997 |
| JP | 3255090 | 11/1991 |
| JP | 9124669 | 5/1997 |
| JP | 10182678 | 7/1998 |
| JP | 2000-7688 | 1/2000 |
| JP | 2000-136194 | 5/2000 |
| JP | 2004-196793 | 7/2004 |

OTHER PUBLICATIONS

Horiuchi, T., et al., "Synthesis of (R)- and (S)-7,7'-Bis(diphenylphosphino)-2,2'-dimethoxy-1,1'binaphthyl, a New Axially Dissymmetric Bis(triarylphosphine)", Tetrahedron: Asymmetry, (1994), vol. 5, No. 3, pp. 325-328.

Imamoto., et al., "Phosphine Oxides and LiAlH4-NaBH4-CeCl3: Synthesis and Reactions of Phosphine-Boranes", J. Am. Chem. Soc., (1985), vol. 107, pp. 5301-5303.

Kumobayashi, H., et al., "Recent Advances of BINAP Chemistry in the Industrial Aspects", Synlett, (2001), No. S1, pp. 1055-1064.

Saito, t., et al., "New Chiral Diphosphine Ligands Designed to have a Narrow Dihedral Angle in the Biaryl Backbone", Adv. Synth. Catal., (2001), vol. 343, No. 5, pp. 264-267.

Lipshutz, B., et al., "Pd(0)-Mediated Couplings of Aryl Nonaflates and Triflates with Diphenylphosphine-Borane. Preparation of BH3-Stabilized, Unsymmetrical Triarylphosphines", Tetrahedron Letters 40, (1999), pp. 201-204.

McKinstry, L., et al., "An Efficient Procedure for the Synthesis of C-Chiral Bisphosphines", Tetrahedron, (1995), vol. 51, No. 28, pp. 7655-7666.

Miura, T., et al., "Synthesis and Reactions of Optically Active Secondary Dialkylphosphine-Boranes", J. Org. Chem., (2000), vol. 65, No. 6, pp. 1877-1880.

Ohff, M., et al., "Borane Complexes of Trivalent Organophosphorus Compounds. Versatile Precursors for the Synthesis of Chiral Phosphine Ligands for Asymmetric Catalysis", Synthesis, (1998), No. 10, pp. 1391-1415.

Hayashi, T., et al., "Rhodium-Catalyzed Asymmetric Conjugate Addition of Organoboronic Acids to Nitroalkenes", J. Am. Chem. Soc., (2000), vol. 122, No. 43, pp. 10716-10717.

Lee et al., Angewandte. Chemie. International, Edition. 2002, 41(5), pp. 847-849.

Japanese Office Action (with English translation) issued Feb. 10, 2009 in connection with Japanese Application No. 2002-354338, which corresponds to U.S. Appl. No. 11/682,630.

Imamoto, T., "Synthesis and Reactions of Phosphine-Boranes", Journal of Synthetic Organic Chemistry, Japan (1993), vol. 51, No. 3, pp. 223-231 (with English translation).

\* cited by examiner

PROCESS FOR PREPARATION OF DIPHOSPHINE COMPOUNDS AND INTERMEDIATES FOR THE PROCESS

This application is a divisional application of U.S. application Ser. No. 11/682,630, filed Mar. 6, 2007 now U.S. Pat. No. 7,678,942, which is a divisional application of U.S. Ser. No. 10/497,808, filed Jun. 4, 2004, now U.S. Pat. No. 7,208,633 which was the national phase filing of International Patent Application No. PCT/JP02/12758, filed Dec. 5, 2002.

TECHNICAL FIELD

The present invention relates to a production method of diphosphine compounds. More particularly, the present invention relates to a production method of phosphinobinaphthyl using a phosphine-borane complex, which is useful as a ligand for a transition metal catalyst for an asymmetric synthesis reaction.

BACKGROUND ART

In asymmetric reduction, asymmetric isomerization and the like using a transition metal coordinated with optically active phosphine as a catalyst, 2,2'-(bis(diphenylphosphino)-1,1'-binaphthyl (hereinafter sometimes to be abbreviated as BINAP) is generally used as the optically active phosphine. Depending on the kind of substrate, however, reactivity, stereoselectivity, catalytic efficiency and the like are insufficient. Therefore, various optically active phosphines have been produced and reported (e.g., Handbook of Enantioselective Catalysis with Transition Metal Compounds, VCH Publishers (1993)). For example, JP-A-S63-63690 teaches that a ruthenium complex using 2,2'-bis(di(p-toluoyl)phosphino)-1,1'-binaphthyl as a ligand is useful for the asymmetric reduction of a carbon-carbon double bond, JP-A-H3-255090 teaches that a ruthenium complex using 2,2'-bis(di(3,5-dialkylphenyl)phosphino)-1,1'-binaphthyl as a ligand is useful for the asymmetric reduction of β-keto ester.

As the production methods of BINAP and BINAP analogs,

1) JP-A-H3-255090 describes the following reaction formula as a production method of a compound represented by the formula

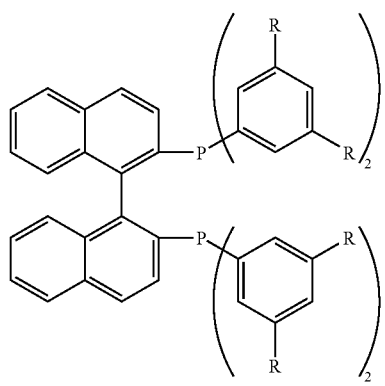

wherein R is a lower alkyl group (hereinafter to be abbreviated as 3,5-DABIN):

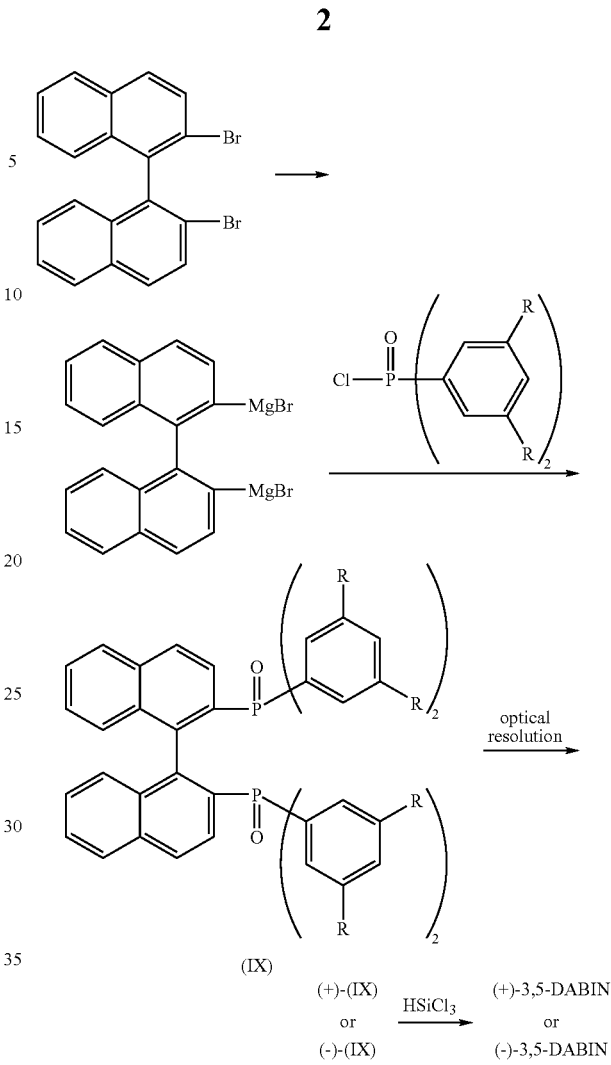

As regards the above-mentioned optical resolution, this reference describes as follows. That is, racemic compound (IX) is dissolved by heating in carbon tetrachloride, a solution of (−)-benzoyltartaric acid in ether is added and the mixture is stirred. The crystals are precipitated, and the crystals are repeatedly recrystallized until they show a certain level of rotation. The purified crystals are suspended in methylene chloride, and 2N sodium hydroxide is added, whereby free phosphine oxide (−)-(IX) in a (−) form is obtained.

2) JP-T-H10-501234 or WO 95/32934 describes a production method of BINAP, which comprises reacting a compound represented by the formula

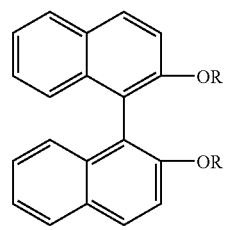

wherein R is triflate, mesylate or tosylate, with diphenylphosphine in the presence of an amine base and a nickel catalyst.

3) JP-A-H9-124669 describes a production method of optically active diphosphine represented by the formula

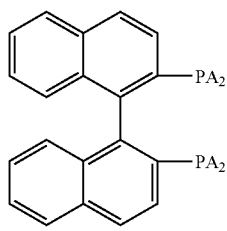

wherein A is a phenyl group, a substituted phenyl group, a naphthyl group optionally substituted by a lower alkyl group or a lower alkoxy group, which comprises reacting an optically active 2,2'-bis(trifluoromethanesulfonyloxy)-1,1'-binaphthyl with phosphine oxide represented by the formula $A_2P(O)H$ wherein A is as defined above, in the presence of a transition metal-phosphine complex to synthesize a mixture containing an optically active diphosphine compound and/or an optically active diphosphine monoxide compound, and further reacting the mixture containing the optically active diphosphine compound and/or the optically active diphosphine monoxide compound with a reducing agent.

4) *Chemical Communications*, pp. 2359-2360 (1997) describes a production method to give (S)-BINAP, which comprises reacting (S)-2,2'-bis(trifluoromethanesulfonyloxy)-1,1'-binaphthyl with diphenylphosphine chloride in the presence of $NiCl_2$.[1,2-bis(diphenylphosphino)ethane] and zinc.

5) JP-A-2000-7688 describes a production method of optically active 2,2'-bis(di-substituted phosphino)-1,1'-binaphthyl, which comprises reacting a sulfonic acid ester of optically active 2,2'-dihydroxy-1,1'-binaphthyl represented by the formula

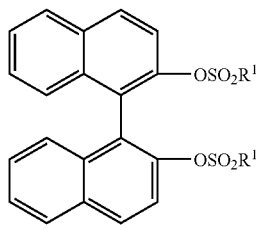

wherein $R^1$ is an alkyl group, a perfluoroalkyl group, an aryl group or a perfluoroaryl group, with chloro di-substituted phosphine represented by the formula

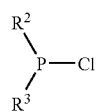

wherein $R^2$ and $R^3$ may be the same or different and each is an aryl group or a cycloalkyl group, in the presence of a hydrogen, an amine, a hydrogenation catalyst and a transition metal catalyst.

6) JP-A-2000-136194 describes a production method of a compound represented by the formula

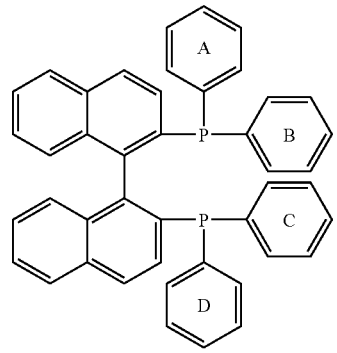

wherein ring A, ring B, ring C and ring D are each a benzene ring having a substituent, which comprises reacting a compound represented by the formula

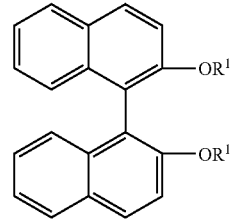

wherein $R^1$ and $R^2$ are each an optionally substituted alkylsulfonyl group or an optionally substituted arylsulfonyl group, with diphenylphosphine having a substituent, in the presence of an amine and a transition metal.

As a phosphine-borane complex,

7) *Tetrahedron Letters*, vol. 40, pp. 201-204 (1999) describes a production method to give a monophosphine compound by reacting aryl triflate or aryl nonaflate with a diphenylphosphine-borane complex in the presence of a transition metal and a base.

8) *Tetrahedron Asymmetry*, vol. 5, pp. 325-328 (1994) describes that synthesis of a diphosphine compound by reacting 2,2'-dimethoxy-7,7'-bis(trifluoromethanesulfonyloxy)-1,1'-binaphthyl with a diphenylphosphine-borane complex in the presence of a transition metal did not succeed.

9) As regards a diphenylphosphine-borane complex wherein a phenyl group has a substituent, U.S. Pat. No. 2,926,194 describes a bis(p-methylphenyl)phosphine-borane complex, a bis(p-biphenylyl)phosphine-borane complex and a bis(2-naphthyl)phosphine-borane complex, and *Tetrahedron*, vol. 51, pp. 7655-7666 (1995) describes a bis(4-methoxy-2-methylphenyl)phosphine-borane complex.

In the aforementioned 2), 4), 5) and 6), a trivalent organic phosphorus compound which is susceptible to oxidization and unstable is used as a reaction reagent, and in the aforementioned 1) and 3), trichlorosilane is used as a reducing agent. Therefore, they are not industrially advantageous methods, and establishment of a production method of BINAP and BINAP analogs, which is suitable for industrial mass production, has been desired.

On the other hand, in the aforementioned 7) and 8), reaction of a diphenylphosphine-borane complex, which is stable and easy to handle, with aryl triflate was tried. In 7), synthesis of a monophosphine compound alone was successful but as described in 8), synthesis of a diphosphine compound necessary for the production method of BINAP was not successful.

For synthesis of various BINAP analogs from a diphenylphosphine-borane complex, a diphenylphosphine-borane complex comprising a phenyl group having a substituent is necessary. However, in 9), synthesis examples of only 4 kinds of diphenylphosphine-borane complexes are merely described.

DISCLOSURE OF THE INVENTION

The present inventors have studied various aspects of a production method suitable for industrial mass production of BINAP analogs, and first reacted a compound represented by the formula

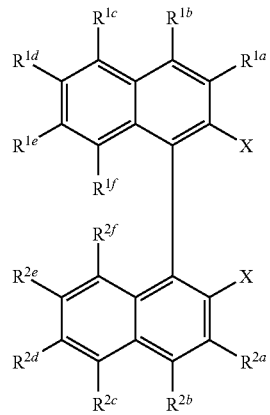

(II)

wherein $R^{1a}$, $R^{1b}$, $R^{1c}$, $R^{1d}$, $R^{1e}$, $R^{1f}$, $R^{2a}$, $R^{2b}$, $R^{2c}$, $R^{2d}$, $R^{2e}$ and $R^{2f}$ are the same or different and each is a hydrogen atom, a fluorine atom, a chlorine atom, an optionally substituted alkyl group, an optionally substituted cycloalkyl group, an optionally substituted aryl group, an optionally substituted hydroxy group, an optionally substituted amino group, an optionally substituted alkylcarbonyl group, an optionally substituted alkoxycarbonyl group, a carboxyl group or an optionally substituted carbamoyl group, X is a leaving group [hereinafter sometimes to be abbreviated as compound (II)] or a salt thereof, with a phosphine-borane complex represented by the formula

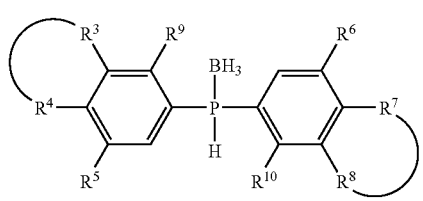

(III)

wherein $R^3$, $R^4$, $R^5$, $R^6$, $R^7$, $R^8$, $R^9$ and $R^{10}$ are the same or different and each is a hydrogen atom, a fluorine atom, a chlorine atom, an optionally substituted hydrocarbon group, an optionally substituted hydroxy group or an optionally substituted amino group, and $R^3$ and $R^4$ and $R^7$ and $R^8$ may form, together with the adjacent carbon atoms, a 5- to 8-membered homocyclic ring or heterocyclic ring [hereinafter sometimes to be abbreviated as compound (III)] or a salt thereof, in a solvent in the presence of an amine and a nickel catalyst to find that a compound represented by the formula

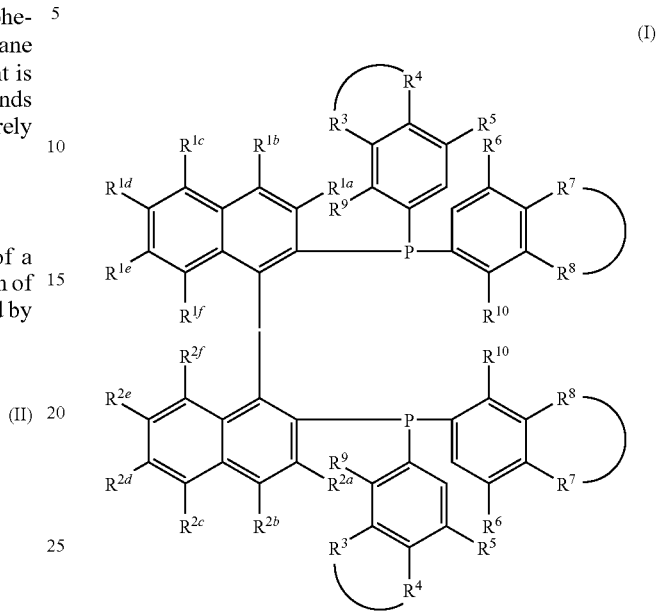

(I)

wherein the symbols are as defined above [hereinafter sometimes to be abbreviated as compound (I)] or a salt thereof can be efficiently obtained in a short step without isomerization, and this method is an industrially superior production method in terms of convenience, economic aspect, easiness of operation based on stability of the starting material and the like, which resulted in the completion of the present invention.

Accordingly, the present invention relates to

[1] a production method of a compound represented by the formula

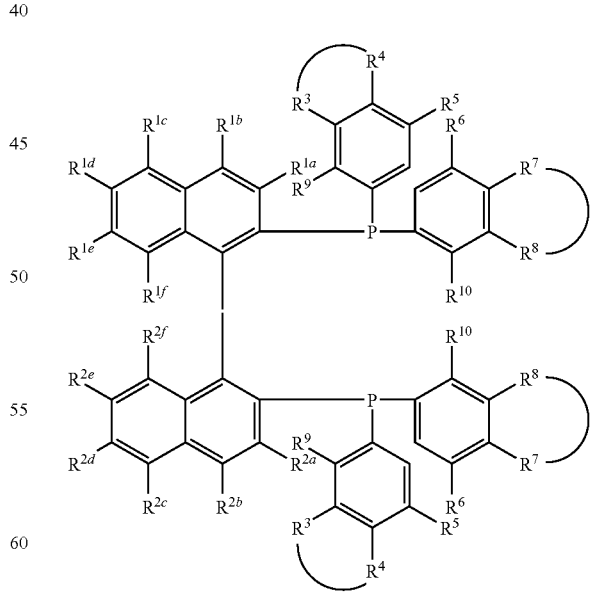

wherein $R^{1a}$, $R^{1b}$, $R^{1c}$, $R^{1d}$, $R^{1e}$, $R^{1f}$, $R^{2a}$, $R^{2b}$, $R^{2c}$, $R^{2d}$, $R^{2e}$ and $R^{2f}$ are the same or different and each is a hydrogen atom, a fluorine atom, a chlorine atom, an optionally substituted alkyl group, an optionally substituted cycloalkyl group, an optionally substituted aryl group, an optionally substituted hydroxy group, an optionally substituted amino group, an optionally substituted alkylcarbonyl group, an optionally substituted alkoxycarbonyl group, a carboxyl group or an optionally substituted carbamoyl group, $R^3$, $R^4$, $R^5$, $R^6$, $R^7$, $R^8$, $R^9$ and $R^{10}$ are the same or different and each is a hydrogen atom, a fluorine atom, a chlorine atom, an optionally substituted hydrocarbon group, an optionally substituted hydroxy group or an optionally substituted amino group, and $R^3$ and $R^4$, and $R^7$ and $R^8$ may each form, together with the adjacent carbon atoms, a 5- to 8-membered homocyclic or heterocyclic ring, or a salt thereof, which comprises reacting a compound represented by the formula

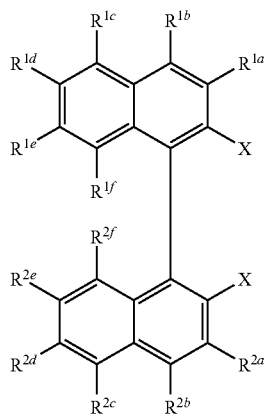

wherein X is a leaving group and other symbols are as defined above, or a salt thereof, with a phosphine-borane complex represented by the formula

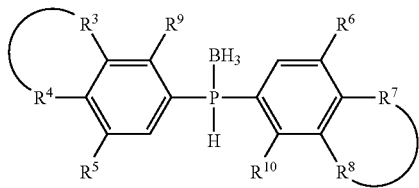

wherein the symbols are as defined above, or a salt thereof, in a solvent in the presence of an amine and a nickel catalyst,

[2] the production method of the aforementioned [1], wherein X is an optionally substituted alkylsulfonyloxy group or an optionally substituted arylsulfonyloxy group,

[3] the production method of the aforementioned [1], wherein $R^{1a}$, $R^{1b}$, $R^{1c}$, $R^{1d}$, $R^{1e}$, $R^{1f}$, $R^{2a}$, $R^{2b}$, $R^{2c}$, $R^{2d}$, $R^{2e}$ and $R^{2f}$ are the same or different and each is a hydrogen atom, a fluorine atom, a chlorine atom, an optionally substituted alkyl group, an optionally substituted cycloalkyl group, an optionally substituted hydroxy group, an optionally substituted amino group, an optionally substituted alkylcarbonyl group, an optionally substituted alkoxycarbonyl group, a carboxyl group or an optionally substituted carbamoyl group, $R^3$, $R^4$, $R^5$, $R^6$, $R^7$ and $R^8$ are the same or different and each is a hydrogen atom, a fluorine atom, a chlorine atom, an optionally substituted hydrocarbon group, an optionally substituted hydroxy group or an optionally substituted amino group, $R^9$ and $R^{10}$ are each a hydrogen atom, and X is an optionally substituted alkylsulfonyloxy group or an optionally substituted arylsulfonyloxy group,

[4] the production method of the aforementioned [3], wherein $R^{1a}$ and $R^{2a}$, $R^{1b}$ and $R^{2b}$, $R^{1c}$ and $R^{2c}$, $R^{1d}$ and $R^{2d}$, $R^{1e}$ and $R^{2e}$, and $R^{1f}$ and $R^{2f}$ are respectively the same groups,

[5] the production method of the aforementioned [1] to [3], wherein $R^{1a}$, $R^{1f}$, $R^{2a}$ and $R^{2f}$ are each a hydrogen atom,

[6] the production method of the aforementioned [3], wherein $R^{1a}$, $R^{1b}$, $R^{1c}$, $R^{1d}$, $R^{1e}$, $R^{1f}$, $R^{2a}$, $R^{2b}$, $R^{2c}$, $R^{2d}$, $R^{2e}$ and $R^{2f}$ are each a hydrogen atom,

[7] the production method of the aforementioned [3], wherein $R^3$, $R^5$, $R^6$ and $R^8$ are each a lower alkyl group and $R^4$ and $R^7$ are each a hydrogen atom or a lower alkoxy group,

[8] the production method of the aforementioned [3], wherein $R^3$, $R^5$, $R^6$ and $R^8$ are each a hydrogen atom, and $R^4$ and $R^7$ are each a lower alkyl group or a lower alkoxy group,

[9] the production method of the aforementioned [3], wherein $R^3$, $R^4$, $R^5$, $R^6$, $R^7$ and $R^8$ are each a hydrogen atom,

[10] the production method of the aforementioned [1], wherein X is trifluoromethanesulfonyloxy, methanesulfonyloxy or p-toluenesulfonyloxy,

[11] the production method of the aforementioned [1] to [3], wherein the nickel catalyst is $NiCl_2$.bis(diphenyl)phosphino $C_{1-4}$ alkane, $NiBr_2$, $NiCl_2$, $NiCl_2$.bis(diphenyl)phosphinyl ferrocene, $NiCl_2$.bis(triphenylphosphine), Ni.tetrakistriphenylphosphine, Ni.tetrakistriphenylphosphite or Ni.dicarbonylbis(triphenyl)phosphine,

[12] the production method of the aforementioned [1] to [3], wherein the nickel catalyst is $NiCl_2$.bis(diphenyl)phosphino $C_{1-4}$ alkane,

[13] the production method of the aforementioned [1] to [3], wherein the nickel catalyst is $NiCl_2$.bis(diphenyl)phosphinoethane,

[14] the production method of the aforementioned [1] to [3], wherein the amine is a tertiary amine,

[15] the production method of the aforementioned [1] to [3], wherein the amine is 1,4-diazabicyclo[2.2.2]octane,

[16] the production method of the aforementioned [1] to [3], wherein the solvent is a mixed solvent of one or more kinds selected from N,N-dimethylformamide, N,N-dimethylacetamide, 1-methyl-2-pyrrolidone and 1,3-dimethyl-2-imidazolidinone,

[17] the production method of the aforementioned [1], wherein $R^{1a}$, $R^{1b}$, $R^{1c}$, $R^{1f}$, $R^{2a}$, $R^{2b}$, $R^{2c}$ and $R^{2f}$ are each a hydrogen atom, $R^{1d}$ and $R^{2d}$ are each a hydrogen atom or a $C_{6-10}$ aryl group, $R^{1e}$ and $R^{2e}$ are each a hydrogen atom or a $C_{1-6}$ alkoxy group, $R^3$ is a hydrogen atom or a $C_{1-6}$ alkyl group, $R^4$ is a hydrogen atom, a fluorine atom, a chlorine atom, a $C_{1-6}$ alkyl group, a $C_{6-10}$ aryl group, a $C_{1-6}$ alkoxy group or a di-$C_{1-6}$ alkylamino group, or $R^3$ and $R^4$ form, together with the adjacent carbon atoms, a benzene ring or a 1,3-dioxolane ring, $R^5$ is a hydrogen atom or a $C_{1-6}$ alkyl group, $R^6$ is a hydrogen atom or a $C_{1-6}$ alkyl group, $R^7$ is a hydrogen atom, a fluorine atom, a chlorine atom, a $C_{1-6}$ alkyl group, a $C_{6-10}$ aryl group, a $C_{1-6}$ alkoxy group or a di-$C_{1-6}$ alkylamino group, $R^8$ is a hydrogen atom or a $C_{1-6}$ alkyl group, or $R^7$ and $R^8$ form, together with the adjacent carbon atoms, a benzene ring or a 1,3-dioxolane ring, $R^9$ is a hydrogen atom or a $C_{1-6}$ alkyl group, $R^{10}$ is a hydrogen atom or a $C_{1-6}$ alkyl group, X is trifluoromethanesulfonyloxy, and the nickel catalyst is $NiCl_2$ bis(diphenyl)phosphinoethane,

[18] the production method of the aforementioned [1], wherein an axial chiral moiety of the compound represented by the formula

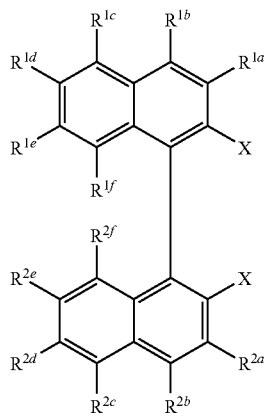

wherein each symbol is as defined in the aforementioned [1], and an axial chiral moiety of the compound represented by the formula

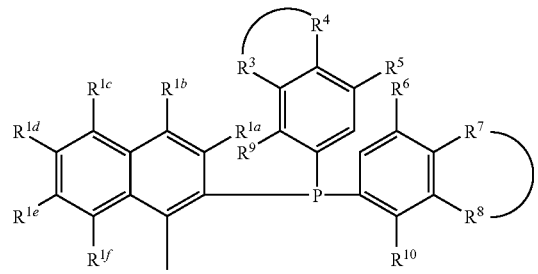

wherein each symbol is as defined in the aforementioned [1], are each an (R) form,

[19] the production method of the aforementioned [18], wherein the reaction is free of racemization,

[20] the production method of the aforementioned [1], wherein an axial chiral moiety of the compound represented by the formula

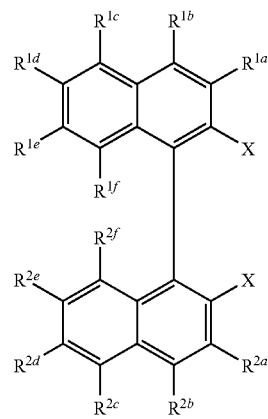

wherein each symbol is as defined in the aforementioned [1], and an axial chiral moiety of the compound represented by the formula

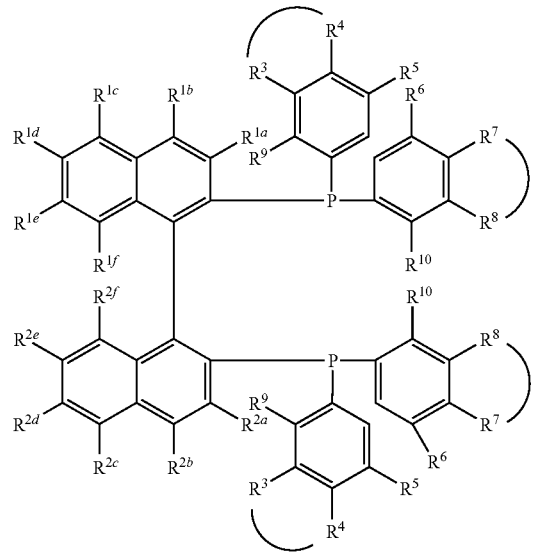

wherein each symbol is as defined in the aforementioned [1], are each an (S) form,

[21] the production method of the aforementioned [20], wherein the reaction is free of racemization,

[22] the production method of the aforementioned [1], wherein an axial chiral moiety of the formula

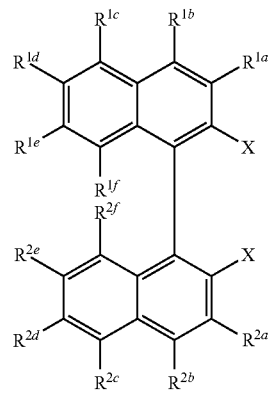

wherein each symbol is as defined in the aforementioned [1], and an axial chiral moiety of the compound represented by the formula

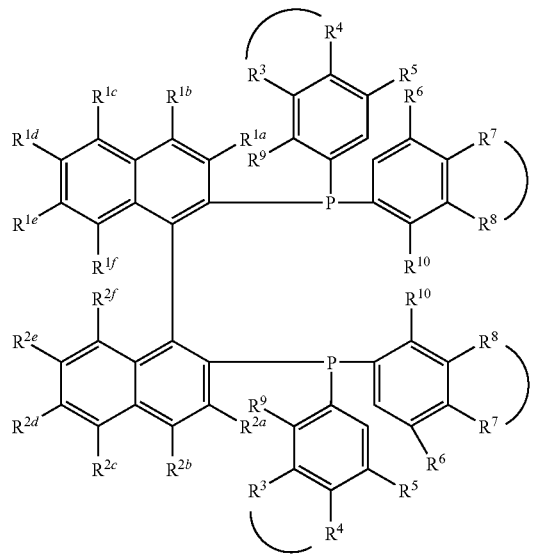

wherein each symbol is as defined in the aforementioned [1], are each a racemate,

[23] 2,2'-bis[bis(3,5-di-tert-butyl-4-methoxyphenyl)phosphino]-1,1'-binaphthyl or a salt thereof,

[24] a phosphine-borane complex represented by the formula

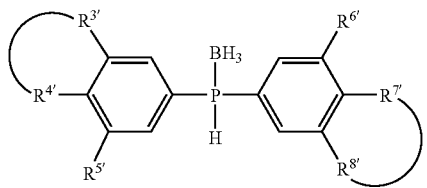

wherein $R^{3'}$, $R^{5'}$, $R^{6'}$ and $R^{8'}$ are each a hydrogen atom, a lower alkyl group or a lower alkoxy group, and $R^{4'}$ and $R^{7'}$ are each a hydrogen atom, a fluorine atom, a chlorine atom, a $C_{2-6}$ alkyl group, a lower alkoxy group, a mono-lower alkylamino group or a di-lower alkylamino group ($R^{3'}$ and $R^{4'}$, and $R^{7'}$ and $R^{8'}$ may each form a lower alkylenedioxy group) (provided that $R^{3'}$, $R^{4'}$, $R^{5'}$, $R^{6'}$, $R^{7'}$ and $R^{8'}$ are not hydrogen atoms at the same time), or a salt thereof,

[25] the phosphine-borane complex of the aforementioned [24], wherein $R^{3'}$, $R^{5'}$, $R^{6'}$ and $R^{8'}$ are each a hydrogen atom or a lower alkyl group, and $R^{4'}$ and $R^{7'}$ are each a hydrogen atom, a fluorine atom, a chlorine atom, a lower alkoxy group, a mono-lower alkylamino group or a di-lower alkylamino group,

[26] the phosphine-borane complex of the aforementioned [25], wherein $R^{3'}$, $R^{5'}$, $R^{6'}$ and $R^{8'}$ are each a hydrogen atom, and $R^{4'}$ and $R^{7'}$ are each a fluorine atom, a chlorine atom, a lower alkoxy group or a di-lower alkylamino group,

[27] the phosphine-borane complex of the aforementioned [25], wherein $R^{3'}$, $R^{5'}$, $R^{6'}$ and $R^{8'}$ are each a lower alkyl group, and $R^{4'}$ and $R^{7'}$ are each a hydrogen atom,

[28] the phosphine-borane complex of the aforementioned [25], wherein $R^{3'}$, $R^{5'}$, $R^{6'}$ and $R^{8'}$ are each a lower alkyl group, and $R^{4'}$ and $R^{7'}$ are each a lower alkoxy group,

[29] the phosphine-borane complex of the aforementioned [24], wherein $R^{5'}$ and $R^{6'}$ are each a hydrogen atom, and $R^{3'}$ and $R^{4'}$, and $R^{7'}$ and $R^{8'}$ each form a methylenedioxy group,

[30] the phosphine-borane complex of the aforementioned [24], wherein $R^{3'}$, $R^{5'}$, $R^{6'}$ and $R^{8'}$ are each a hydrogen atom, and $R^{4'}$ and $R^{7'}$ are each a $C_{2-6}$ alkyl group,

[31] the phosphine-borane complex of the aforementioned [24], wherein $R^{4'}$, $R^{5'}$, $R^{7'}$ and $R^{8'}$ are each a hydrogen atom, and $R^{3'}$ and $R^{6'}$ are each a lower alkyl group,

[32] a phosphine-borane complex represented by the formula

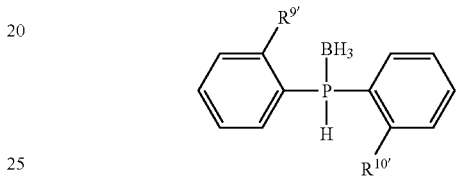

wherein $R^{9'}$ and $R^{10'}$ are each a lower alkyl group,

[33] a production method of a phosphine-borane complex represented by the formula

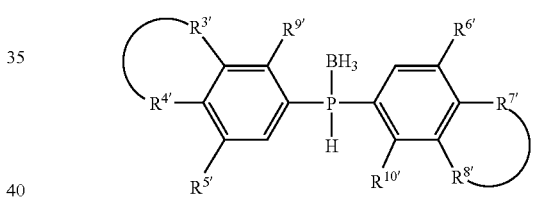

wherein $R^{3'}$, $R^{5'}$, $R^{6'}$ and $R^{8'}$ are each a hydrogen atom, a lower alkyl group or a lower alkoxy group, $R^{4'}$ and $R^{7'}$ are each a hydrogen atom, a fluorine atom, a chlorine atom, a $C_{2-6}$ alkyl group, a lower alkoxy group, a mono-lower alkylamino group or a di-lower alkylamino group, and $R^{9'}$ and $R^{10'}$ are each a hydrogen atom or a lower alkyl group ($R^{3'}$ and $R^{4'}$, and $R^{7'}$ and $R^{8'}$ may each form a lower alkylenedioxy group) (provided that $R^{3'}$, $R^{4'}$, $R^{5'}$, $R^{6'}$, $R^{7'}$, $R^{8'}$, $R^{9'}$ and $R^{10'}$ are not hydrogen atoms at the same time), or a salt thereof, which comprises reducing a compound represented by the formula

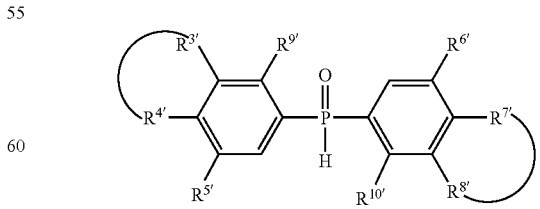

wherein each symbol is as defined above, or a salt thereof, with lithium aluminum hydride in the presence of cerium chloride and sodium borohydride,

[34] a production method of an optically active compound, which comprises reducing a compound to be reduced, in the presence of an optically active compound represented by the formula

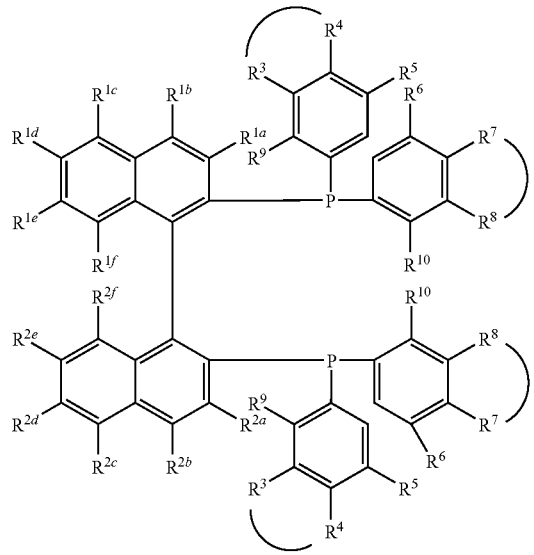

wherein $R^{1a}$, $R^{1b}$, $R^{1c}$, $R^{1d}$, $R^{1e}$, $R^{1f}$, $R^{2a}$, $R^{2b}$, $R^{2c}$, $R^{2d}$, $R^{2e}$ and $R^{2f}$ are the same or different and each is a hydrogen atom, a fluorine atom, a chlorine atom, an optionally substituted alkyl group, an option ally substituted cycloalkyl group, an optionally substituted aryl group, an optionally substituted hydroxy group, an optionally substituted amino group, an optionally substituted alkylcarbonyl group, an optionally substituted alkoxycarbonyl group, a carboxyl group or an optionally substituted carbamoyl group and $R^3$, $R^4$, $R^5$, $R^6$, $R^7$, $R^8$, $R^9$ and $R^{10}$ are the same or different and each is a hydrogen atom, a fluorine atom, a chlorine atom, an optionally substituted hydrocarbon group, an optionally substituted hydroxy group or an optionally substituted amino group, and $R^3$ and $R^4$, and $R^7$ and $R^8$ may each form, together with the adjacent carbon atoms, a 5- to 8-membered homocyclic ring or heterocyclic ring or a salt thereof, which is obtained by reacting an optically active compound represented by the formula

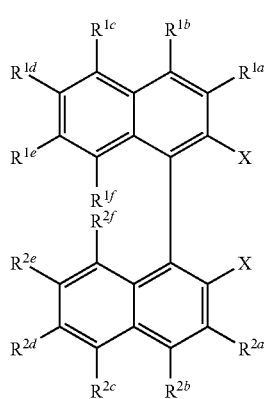

wherein X is a leaving group and other symbols are as defined above, or a salt thereof, with a phosphine-borane complex represented by the formula

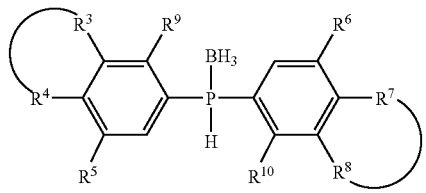

wherein the symbols are as defined above, or a salt thereof, in a solvent in the presence of an amine and a nickel catalyst,

[35] use of a phosphine-borane complex represented by the formula

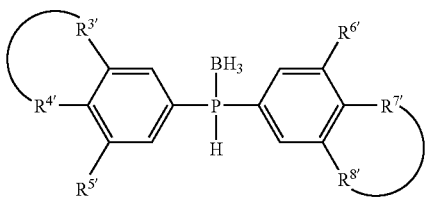

wherein $R^{3'}$, $R^{5'}$, $R^{6'}$ and $R^{8'}$ are each a hydrogen atom, a lower alkyl group or a lower alkoxy group, $R^{4'}$ and $R^{7'}$ are each a hydrogen atom, a fluorine atom, a chlorine atom, a $C_{2-6}$ alkyl group, a lower alkoxy group, a mono-lower alkylamino group or a di-lower alkylamino group ($R^{3'}$ and $R^{4'}$, and $R^{7'}$ and $R^{8'}$ may each form a lower alkylenedioxy group) (provided that $R^{3'}$, $R^{4'}$, $R^{5'}$, $R^{6'}$, $R^{7'}$ and $R^{8'}$ are not hydrogen atoms at the same time) or a phosphine-borane complex represented by the formula

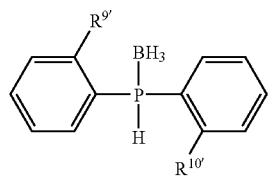

wherein $R^{9'}$ and $R^{10'}$ are each a lower alkyl group, or a salt thereof, for the production of an optically active compound by asymmetric reduction,

[36] use of (S)-2,2'-bis[bis(3,5-di-tert-butyl-4-methoxyphenyl)phosphino]-1,1'-binaphthyl or (R)-2,2'-bis[bis(3,5-di-tert-butyl-4-methoxyphenyl)phosphino]-1,1'-binaphthyl or a salt thereof for the production of an optically active compound by asymmetric reduction, and the like.

The compound (I) and compound (II) include an (R) form, an (S) form and a mixture of an (R) form and an (S) form (the ratio of the two is not limited).

The "alkyl group" of the aforementioned "optionally substituted alkyl group" for $R^{1a}$, $R^{1b}$, $R^{1c}$, $R^{1d}$, $R^{1e}$, $R^{1f}$, $R^{2a}$, $R^{2b}$, $R^{2c}$, $R^{2d}$, $R^{2e}$ or $R^{2f}$ refers to, for example, a lower alkyl group ($C_{1-6}$ alkyl group such as methyl, ethyl, propyl, isopropyl, butyl, isobutyl, sec-butyl, tert-butyl, pentyl, hexyl etc.) and the like.

As the substituent of the "alkyl group", nitro, nitroso, cyano, hydroxy, a lower alkoxy group (e.g., $C_{1-6}$ alkoxy group such as methoxy, ethoxy, propoxy, isopropoxy, butoxy, isobutoxy, sec-butoxy, tert-butoxy, pentoxy, hexyloxy etc.), formyl, a lower alkylcarbonyl group (e.g., $C_{1-6}$ alkyl-carbonyl group such as acetyl, propionyl, butyryl, isobutyryl, valeryl, isovaleryl, pivaloyl etc.), a lower alkoxycarbonyl group (e.g., $C_{1-6}$ alkoxy-carbonyl group such as methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentoxycarbonyl, hexyloxycarbonyl etc.), carboxyl, an N-mono-lower alkylcarbamoyl group (e.g., N-mono-$C_{1-6}$ alkyl-carbamoyl group such as N-methylcarbamoyl, N-ethylcarbamoyl, N-propylcarbamoyl, N-isopropylcarbamoyl, N-butylcarbamoyl, N-isobutylcarbamoyl, N-tert-butylcarbamoyl etc.), an N,N-di-lower alkylcarbamoyl group (e.g., N,N-di-$C_{1-6}$ alkyl-carbamoyl group such as N,N-dimethylcarbamoyl, N,N-diethylcarbamoyl, N,N-dipropylcarbamoyl, N,N-diisopropylcarbamoyl, N-ethyl-N-methylcarbamoyl etc.) and the like can be mentioned. It may have 1 to 3 selected from these substituents at substitutable position(s).

The "cycloalkyl group" of the "optionally substituted cycloalkyl group" for the aforementioned $R^{1a}$, $R^{1b}$, $R^{1c}$, $R^{1d}$, $R^{1e}$, $R^{1f}$, $R^{2a}$, $R^{2b}$, $R^{2c}$, $R^{2d}$, $R^{2e}$ or $R^{2f}$ refers to, for example, a $C_{3-6}$ cycloalkyl group such as cyclopropyl, cyclobutyl, cyclopentyl, cyclohexyl and the like, and the like.

As the substituent of the "cycloalkyl group", the same number and the same substituents as the substituents that the "optionally substituted alkyl group" for $R^{1a}$, $R^{1b}$, $R^{1c}$, $R^{1d}$, $R^{1e}$, $R^{1f}$, $R^{2a}$, $R^{2b}$, $R^{2c}$, $R^{2d}$, $R^{2e}$ or $R^{2f}$ may have can be mentioned.

The "aryl group" of the "optionally substituted aryl group" for the aforementioned $R^{1a}$, $R^{1b}$, $R^{1c}$, $R^{1d}$, $R^{1e}$, $R^{1f}$, $R^{2a}$, $R^{2b}$, $R^{2c}$, $R^{2d}$, $R^{2e}$ or $R^{2f}$ refers to, for example, a $C_{6-10}$ aryl group such as phenyl, 1-naphthyl, 2-naphthyl and the like, and the like.

As the substituent of the "aryl group", the same number and the same substituents as the substituents that the "optionally substituted alkyl group" for $R^{1a}$, $R^{1b}$, $R^{1c}$, $R^{1d}$, $R^{1e}$, $R^{1f}$, $R^{2a}$, $R^{2b}$, $R^{2c}$, $R^{2d}$, $R^{2e}$ or $R^{2f}$ may have can be mentioned.

As the substituent of the "optionally substituted hydroxy group" for the aforementioned $R^{1a}$, $R^{1b}$, $R^{1c}$, $R^{1d}$, $R^{1e}$, $R^{1f}$, $R^{2a}$, $R^{2b}$, $R^{2c}$, $R^{2d}$, $R^{2e}$ or $R^{2f}$, an optionally substituted lower alkyl group (e.g., $C_{1-6}$ alkyl group such as methyl, ethyl, propyl, isopropyl, butyl, isobutyl, sec-butyl, tert-butyl, pentyl, hexyl etc.), an optionally substituted lower alkylcarbonyl group (e.g., $C_{1-6}$ alkyl-carbonyl group such as acetyl, propionyl, butyryl, isobutyryl, valeryl, isovaleryl, pivaloyl etc.) and the like can be mentioned.

As the substituent that the "optionally substituted lower alkyl group" and "optionally substituted lower alkylcarbonyl group" may have as the substituent of the "optionally substituted hydroxy group", the same number and the same substituents as the substituents that the "optionally substituted alkyl group" for $R^{1a}$, $R^{1b}$, $R^{1c}$, $R^{1d}$, $R^{1e}$, $R^{1f}$, $R^{2a}$, $R^{2b}$, $R^{2c}$, $R^{2d}$, $R^{2e}$ or $R^{2f}$ may have can be mentioned.

As the substituent of the "optionally substituted amino group" for the aforementioned $R^{1a}$, $R^{1b}$, $R^{1c}$, $R^{1d}$, $R^{1e}$, $R^{1f}$, $R^{2a}$, $R^{2b}$, $R^{2c}$, $R^{2d}$, $R^{2e}$ or $R^{2f}$, an optionally substituted lower alkyl group (e.g., $C_{1-6}$ alkyl group such as methyl, ethyl, propyl, isopropyl, butyl, isobutyl, sec-butyl, tert-butyl, pentyl, hexyl etc.), an optionally substituted lower alkylcarbonyl group (e.g., $C_{1-6}$ alkyl-carbonyl group such as acetyl, propionyl, butyryl, isobutyryl, valeryl, isovaleryl, pivaloyl etc.) and the like can be mentioned, and the group is optionally mono-substituted or di-substituted by these substituents.

As the substituent that the "optionally substituted lower alkyl group" and "optionally substituted lower alkylcarbonyl group" may have as the substituent of the "optionally substituted amino group", the same number and the same substituents as the substituents that the "optionally substituted alkyl group" for $R^{1a}$, $R^{1b}$, $R^{1c}$, $R^{1d}$, $R^{1e}$, $R^{1f}$, $R^{2a}$, $R^{2b}$, $R^{2c}$, $R^{2d}$, $R^{2e}$ or $R^{2f}$ may have can be mentioned As the "alkylcarbonyl group" of the "optionally substituted alkylcarbonyl group" for the aforementioned $R^{1a}$, $R^{1b}$, $R^{1c}$, $R^{1d}$, $R^{1e}$, $R^{1f}$, $R^{2a}$, $R^{2b}$, $R^{2c}$, $R^{2d}$, $R^{2e}$ or $R^{2f}$, for example, a lower alkylcarbonyl group (e.g., a $C_{1-6}$ alkyl-carbonyl group such as acetyl, propionyl, butyryl, isobutyryl, valeryl, isovaleryl, pivaloyl etc.) and the like can be mentioned.

As the substituent of the "optionally substituted alkylcarbonyl group", the same number and the same substituents as the substituents that the "optionally substituted alkyl group" for $R^{1a}$, $R^{1b}$, $R^{1c}$, $R^{1d}$, $R^{1e}$, $R^{1f}$, $R^{2a}$, $R^{2b}$, $R^{2c}$, $R^{2d}$, $R^{2e}$ or $R^{2f}$ may have can be mentioned.

As the "alkoxycarbonyl group" of the "optionally substituted alkoxycarbonyl group" for the aforementioned $R^{1a}$, $R^{1b}$, $R^{1c}$, $R^{1d}$, $R^{1e}$, $R^{1f}$, $R^{2a}$, $R^{2b}$, $R^{2c}$, $R^{2d}$, $R^{2e}$ or $R^{2f}$, for example, a lower alkoxycarbonyl group (e.g., $C_{1-6}$ alkoxycarbonyl group such as methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentoxycarbonyl, hexyloxycarbonyl etc.) and the like can be mentioned.

As the substituent of the "optionally substituted alkoxycarbonyl group", the same number and the same substituents as the substituents that the "optionally substituted alkyl group" for $R^{1a}$, $R^{1b}$, $R^{1c}$, $R^{1d}$, $R^{1e}$, $R^{1f}$, $R^{2a}$, $R^{2b}$, $R^{2c}$, $R^{2d}$, $R^{2e}$ or $R^{2f}$ may have can be mentioned.

As the substituent of the "optionally substituted carbamoyl group" for the aforementioned $R^{1a}$, $R^{1b}$, $R^{1c}$, $R^{1d}$, $R^{1e}$, $R^{1f}$, $R^{2a}$, $R^{2b}$, $R^{2c}$, $R^{2d}$, $R^{2e}$ or $R^{2f}$, for example, an optionally substituted lower alkyl group (e.g., $C_{1-6}$ alkyl group such as methyl, ethyl, propyl, isopropyl, butyl, isobutyl, sec-butyl, tert-butyl, pentyl, hexyl etc.), an optionally substituted lower alkylcarbonyl group (e.g., $C_{1-6}$ alkyl-carbonyl group such as acetyl, propionyl, butyryl, isobutyryl, valeryl, isovaleryl, pivaloyl etc.) and the like can be mentioned, and the group is optionally mono-substituted or di-substituted by these substituents.

As the substituent that the "optionally substituted lower alkyl group" and "optionally substituted lower alkylcarbonyl group" may have as the substituent of the "optionally substituted carbamoyl group", the same number and the same substituents as the substituents that the "optionally substituted alkyl group" for $R^{1a}$, $R^{1b}$, $R^{1c}$, $R^{1d}$, $R^{1e}$, $R^{1f}$, $R^{2a}$, $R^{2b}$, $R^{2c}$, $R^{2d}$, $R^{2e}$ or $R^{2f}$ may have can be mentioned.

As the leaving group for the aforementioned X, for example, a bromine atom, an iodine atom, an optionally substituted alkylsulfonyloxy group, an optionally substituted arylsulfonyloxy group and the like can be mentioned. As the "optionally substituted alkylsulfonyloxy group" as the leaving group for X, for example, a $C_{1-6}$ alkylsulfonyloxy group (e.g., methanesulfonyloxy, ethanesulfonyloxy and the like) optionally having 1 to 13 substituents selected from a halogen atom (e.g., fluorine, chlorine, bromine, iodine etc.), an optionally halogenated $C_{1-6}$ alkyl group and a $C_{1-6}$ alkoxy group (e.g., methoxy, ethoxy, propoxy, isopropoxy, butoxy, isobutoxy etc.), and the like can be mentioned.

As the aforementioned "optionally halogenated $C_{1-6}$ alkyl group", for example, a $C_{1-6}$ alkyl group (e.g., methyl, ethyl, propyl, isopropyl, butyl, isobutyl, sec-butyl, tert-butyl, pentyl, hexyl etc.) optionally having 1 to 13, preferably 1 to 9, halogen atoms (e.g., fluorine, chlorine, bromine, iodine etc.) and the like can be mentioned.

Specific examples of the "optionally substituted alkylsulfonyloxy group" as the leaving group for X include methanesulfonyloxy, ethanesulfonyloxy, trifluoromethanesulfonyloxy, chloromethanesulfonyloxy, trichloromethanesulfonyloxy, nonafluorobutanesulfonyloxy and the like. Of these, methanesulfonyloxy, trifluoromethanesulfonyloxy and the like are preferable.

As the "optionally substituted arylsulfonyloxy group" as the leaving group for X, for example, a $C_{6-10}$ arylsulfonyloxy group (e.g., benzenesulfonyloxy, 1-naphthalenesulfonyloxy, 2-naphthalenesulfonyloxy and the like) optionally having 1 to 5 substituents selected from a halogen atom (e.g., fluorine, chlorine, bromine, iodine etc.), a $C_{1-6}$ alkyl group (e.g., methyl, ethyl, propyl, isopropyl, butyl, isobutyl, sec-butyl, tert-butyl, pentyl, hexyl etc.), a $C_{1-6}$ alkoxy group (e.g., methoxy, ethoxy, propoxy, isopropoxy, butoxy, isobutoxy etc.), nitro and cyano, and the like can be mentioned. Specific examples thereof include benzenesulfonyloxy, p-toluenesulfonyloxy, 1-naphthalenesulfonyloxy, 2-naphthalenesulfonyloxy, p-nitrobenzenesulfonyloxy, m-nitrobenzenesulfonyloxy, m-toluenesulfonyloxy, o-toluenesulfonyloxy, 4-chlorobenzenesulfonyloxy, 3-chlorobenzenesulfonyloxy, 4-methoxybenzenesulfonyloxy and the like. Of these, p-toluenesulfonyloxy and the like are preferable.

As X, methanesulfonyloxy, trifluoromethanesulfonyloxy, p-toluenesulfonyloxy and the like are preferable, and trifluoromethanesulfonyloxy is particularly preferable.

As the "hydrocarbon group" of the "optionally substituted hydrocarbon group" for the aforementioned $R^3$, $R^4$, $R^5$, $R^6$, $R^7$, $R^8$, $R^9$ or $R^{10}$, an alkyl group, an alkenyl group, an alkynyl group, a cycloalkyl group, an aryl group, an aralkyl group and the like can be mentioned.

The "alkyl group" refers to a lower alkyl group (e.g., $C_{1-6}$ alkyl group such as methyl, ethyl, propyl, isopropyl, butyl, isobutyl, sec-butyl, tert-butyl, pentyl, hexyl etc.) and the like.

The "alkenyl group" refers to a lower alkenyl group (e.g., $C_{2-6}$ alkenyl group such as vinyl, allyl, isopropenyl, 1-butenyl, 2-butenyl, 3-butenyl, butadienyl, 2-methylallyl, hexatrienyl, 3-octenyl etc.) and the like.

The "alkynyl group" refers to a lower alkynyl group (e.g., $C_{2-6}$ alkynyl group such as ethynyl, 2-propynyl, butynyl, 3-hexynyl etc.) and the like.

The "cycloalkyl group" refers to, for example, a $C_{3-6}$ cycloalkyl group such as cyclopropyl, cyclobutyl, cyclopentyl, cyclohexyl and the like, and the like.

The "aryl group" refers to, for example, a $C_{6-10}$ aryl group such as phenyl, naphthyl and the like, and the like.

The "aralkyl group" refers to, for example, a $C_{7-10}$ aralkyl group such as benzyl, phenethyl and the like, and the like.

As the substituent of the "optionally substituted hydrocarbon group" for $R^3$, $R^4$, $R^5$, $R^6$, $R^7$, $R^8$, $R^9$ or $R^{10}$, the same number and the same substituents as the substituents that the "optionally substituted alkyl group" for $R^{1a}$, $R^{1b}$, $R^{1c}$, $R^{1d}$, $R^{1e}$, $R^{1f}$, $R^{2a}$, $R^{2b}$, $R^{2c}$, $R^{2d}$, $R^{2e}$ or $R^{2f}$ may have can be mentioned.

As the "optionally substituted hydroxy group" for the aforementioned $R^3$, $R^4$, $R^5$, $R^6$, $R^7$, $R^8$, $R^9$ or $R^{10}$, those similar to the "optionally substituted hydroxy group" for $R^{1a}$, $R^{1b}$, $R^{1c}$, $R^{1d}$, $R^{1e}$, $R^{1f}$, $R^{2a}$, $R^{2b}$, $R^{2c}$, $R^{2d}$, $R^{2e}$ or $R^{2f}$ can be mentioned. Of these, a lower alkoxy group ($C_{1-6}$ alkoxy group), namely, a hydroxy group substituted by a lower alkyl group ($C_{1-6}$ alkyl group) is preferable.

As the "optionally substituted amino group" for the aforementioned $R^3$, $R^4$, $R^5$, $R^6$, $R^7$, $R^8$, $R^9$ or $R^{10}$, those similar to the "optionally substituted amino group" for $R^{1a}$, $R^{1b}$, $R^{1c}$, $R^{1d}$, $R^{1e}$, $R^{1f}$, $R^{2a}$, $R^{2b}$, $R^{2c}$, $R^{2d}$, $R^{2e}$ or $R^{2f}$ can be mentioned. Of these, a di-lower alkylamino group (di-$C_{1-6}$ alkylamino group), namely, an amino group di-substituted by a lower alkyl group ($C_{1-6}$ alkyl group) is preferable.

As the aforementioned "5- to 8-membered homocyclic ring" that may be formed by $R^3$ and $R^4$ and $R^7$ and $R^8$ together with the adjacent carbon atoms, for example, cyclopentane, cyclohexane, cycloheptane, cyclooctane, benzene and the like can be mentioned.

The "5- to 8-membered homocyclic ring" may have substituent(s), and as the substituent, the same number and the same substituents as the substituents that the "optionally substituted alkyl group" for $R^{1a}$, $R^{1b}$, $R^{1c}$, $R^{1d}$, $R^{1e}$, $R^{1f}$, $R^{2a}$, $R^{2b}$, $R^{2c}$, $R^{2d}$, $R^{2e}$ or $R^{2f}$ may have can be mentioned.

As the "5- to 8-membered homocyclic ring", a 6-membered homocyclic ring such as cyclohexane, benzene and the like are preferable, and benzene is particularly preferable.

As the "5- to 8-membered heterocyclic ring" that may be formed by $R^3$ and $R^4$ and $R^7$ and $R^8$ together with the adjacent carbon atoms, for example, pyrrole, imidazole, pyrrolidine, pyrroline, imidazolidine, imidazoline, pyridine, pyrazine, pyrimidine, piperidine, pyrimidine, oxazole, furan, pyran, 1,3-dioxolane, 1,4-dioxane and the like can be mentioned.

The "5- to 8-membered heterocyclic ring" may have substituent(s), and as the substituent, the same number and the same substituents as the substituents that the "optionally substituted alkyl group" for $R^{1a}$, $R^{1b}$, $R^{1c}$, $R^{1d}$, $R^{1e}$, $R^{1f}$, $R^{2a}$, $R^{2b}$, $R^{2c}$, $R^{2d}$, $R^{2e}$ or $R^{2f}$ may have can be mentioned.

As the "5- to 8-membered heterocyclic ring", oxygen-containing heterocyclic rings are preferable, and of such rings, 1,3-dioxolane, 1,4-dioxane and the like are preferable, and 1,3-dioxolane is particularly preferable.

As the compound (II), a compound wherein $R^{1a}$ and $R^{2a}$, $R^{1b}$ and $R^{2b}$, $R^{1c}$ and $R^{2c}$, $R^{1d}$ and $R^{2d}$, $R^{1e}$ and $R^{2e}$, and $R^{1f}$ and $R^{2f}$ are respectively the same groups is preferable, and a compound wherein $R^{1a}$, $R^{1f}$, $R^{2a}$ and $R^{2f}$ are each a hydrogen atom is particularly preferable. Furthermore, a compound wherein $R^{1a}$, $R^{1b}$, $R^{1c}$, $R^{1f}$, $R^{2a}$, $R^{2b}$, $R^{2c}$ and $R^{2f}$ are each a hydrogen atom, $R^{1d}$ and $R^{2d}$ are each a hydrogen atom or a $C_{6-10}$ aryl group, and $R^{1e}$ and $R^{2e}$ are each a hydrogen atom or a $C_{1-6}$alkoxy group is preferable, and a compound wherein $R^{1a}$, $R^{1b}$, $R^{1c}$, $R^{1d}$, $R^{1e}$, $R^{1f}$, $R^{2a}$, $R^{2b}$, $R^{2c}$, $R^{2d}$, $R^{2e}$ and $R^{2f}$ are each a hydrogen atom is particularly preferable.

Specific examples of compound (II) include 2,2'-bis(methanesulfonyloxy)-1,1'-binaphthyl, 2,2'-bis(trifluoromethanesulfonyloxy)-1,1'-binaphthyl, 2,2'-bis(p-toluenesulfonyloxy)-1,1'-binaphthyl, 6,6'-diphenyl-2,2'-bis(trifluoromethanesulfonyloxy)-1,1'-binaphthyl, 7,7'-dimethoxy-2,2'-bis(trifluoromethanesulfonyloxy)-1,1'-binaphthyl and the like. Of these, 2,2'-bis(trifluoromethanesulfonyloxy)-1,1'-binaphthyl, 6,6'-diphenyl-2,2'-bis(trifluoromethanesulfonyloxy)-1,1'-binaphthyl, 7,7'-dimethoxy-2,2'-bis(trifluoromethanesulfonyloxy)-1,1'-binaphthyl and the like are preferable, and 2,2'-bis(trifluoromethanesulfonyloxy)-1,1'-binaphthyl is more preferable.

As compound (II), an optically active compound (II) [(R) form or (S) form] is preferable. As an example of the optically active compound (II), (R)-2,2'-bis(trifluoromethanesulfonyloxy)-1,1'-binaphthyl means a compound represented by the formula

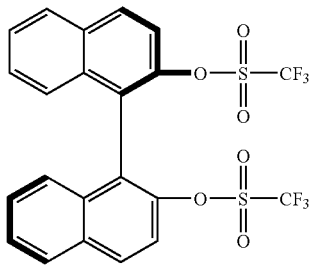

and (S)-2,2'-bis(trifluoromethanesulfonyloxy)-1,1'-binaphthyl means a compound represented by the formula

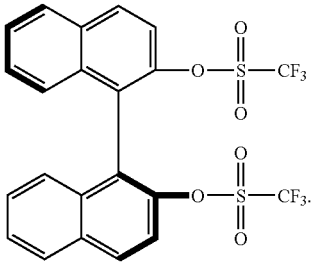

As compound (III), a compound wherein $R^3$ is a hydrogen atom or a $C_{1-6}$ alkyl group, $R^4$ is a hydrogen atom, a fluorine atom, a chlorine atom, a $C_{1-6}$ alkyl group, a $C_{6-10}$ aryl group, a $C_{1-6}$ alkoxy group or a di-$C_{1-6}$ alkylamino group, or $R^3$ and $R^4$ form, together with the adjacent carbon atoms, a benzene ring or a 1,3-dioxolane ring, $R^5$ is a hydrogen atom or a $C_{1-6}$ alkyl group, $R^6$ is a hydrogen atom or a $C_{1-6}$ alkyl group, $R^7$ is a hydrogen atom, a fluorine atom, a chlorine atom, a $C_{1-6}$ alkyl group, a $C_{6-10}$ aryl group, a $C_{1-6}$ alkoxy group or a di-$C_{1-6}$ alkylamino group, $R^8$ is a hydrogen atom or a $C_{1-6}$ alkyl group, or $R^7$ and $R^8$ form, together with the adjacent carbon atoms, a benzene ring or a 1,3-dioxolane ring, $R^9$ is a hydrogen atom or a $C_{1-6}$ alkyl group, and $R^{10}$ is a hydrogen atom or a $C_{1-6}$ alkyl group is preferable.

Particularly, a compound wherein $R^3$, $R^5$, $R^6$ and $R^8$ are the same group, $R^4$ and $R^7$ are the same group, and $R^9$ and $R^{10}$ are each a hydrogen atom is preferable. For example, (i) a compound wherein $R^3$, $R^4$, $R^5$, $R^6$, $R^7$, $R^8$, $R^9$ and $R^{10}$ are each a hydrogen atom, (ii) a compound wherein $R^3$, $R^5$, $R^6$, $R^8$, $R^9$ and $R^{10}$ are each a hydrogen atom, and $R^4$ and $R^7$ are each a fluorine atom or a chlorine atom, (iii) a compound wherein $R^3$, $R^5$, $R^6$, $R^8$, $R^9$ and $R^{10}$ are each a hydrogen atom, and $R^4$ and $R^7$ are each a lower alkyl group ($C_{1-6}$ alkyl group), (iv) a compound wherein $R^3$, $R^5$, $R^6$, $R^8$, $R^9$ and $R^{10}$ are each a hydrogen atom, and $R^4$ and $R^7$ are each a lower alkoxy group ($C_{1-6}$ alkoxy group), (v) a compound wherein $R^3$, $R^5$, $R^6$, $R^8$, $R^9$ and $R^{10}$ are each a hydrogen atom, and $R^4$ and $R^7$ are each a di-lower alkylamino group (di-$C_{1-6}$ alkylamino group), (vi) a compound wherein $R^3$, $R^5$, $R^6$ and $R^8$ are each a lower alkyl group ($C_{1-6}$ alkyl group), and $R^4$, $R^7$, $R^9$ and $R^{10}$ are each a hydrogen atom, (vii) a compound wherein $R^3$, $R^5$, $R^6$ and $R^8$ are each a lower alkyl group ($C_{1-6}$ alkyl group), $R^4$ and $R^7$ are each a lower alkoxy group ($C_{1-6}$ alkoxy group), and $R^9$ and $R^{10}$ are each a hydrogen atom and (viii) a compound wherein $R^3$, $R^5$, $R^6$, $R^8$, $R^9$ and $R^{10}$ are each a hydrogen atom, and $R^4$ and $R^7$ are each a $C_{6-10}$ aryl group can be mentioned.

Particularly, (i) a compound wherein $R^3$, $R^4$, $R^5$, $R^6$, $R^7$, $R^8$, $R^9$ and $R^{10}$ are each a hydrogen atom, (ii) a compound wherein $R^3$, $R^5$, $R^6$, $R^8$, $R^9$ and $R^{10}$ are each a hydrogen atom, and $R^4$ and $R^7$ are each a lower alkyl group ($C_{1-6}$ alkyl group), (iii) a compound wherein $R^3$, $R^5$, $R^6$, $R^8$, $R^9$ and $R^{10}$ are each a hydrogen atom, and $R^4$ and $R^7$ are each a lower alkoxy group ($C_{1-6}$ alkoxy group), (iv) a compound wherein $R^3$, $R^5$, $R^6$ and $R^8$ are each a lower alkyl group ($C_{1-6}$ alkyl group), and $R^4$, $R^7$, $R^9$ and $R^{10}$ are each a hydrogen atom and (v) a compound wherein $R^3$, $R^5$, $R^6$ and $R^8$ are each a lower alkyl group ($C_{1-6}$ alkyl group), $R^4$ and $R^7$ are each a lower alkoxy group ($C_{1-6}$ alkoxy group), and $R^9$ and $R^{10}$ are each a hydrogen atom are preferable.

In addition, as preferable examples thereof, (i) a compound wherein $R^3$ and $R^6$ are each a lower alkyl group ($C_{1-6}$ alkyl group), and $R^4$, $R^5$, $R^7$, $R^8$, $R^9$ and $R^{10}$ are each a hydrogen atom and (ii) a compound wherein $R^3$ and $R^4$ and $R^7$ and $R^8$ form, together with the adjacent carbon atoms, a benzene ring or a 1,3-dioxolane and $R^5$, $R^6$, $R^9$ and $R^{10}$ are each a hydrogen atom can be also mentioned.

Specific examples of compound (III) include a diphenylphosphine-borane complex, a bis(4-methylphenyl)phosphine-borane complex, a bis(4-methoxyphenyl)phosphine-borane complex, a bis(3,5-dimethylphenyl)phosphine-borane complex, a bis(3,5-di-tert-butyl-4-methoxyphenyl)phosphine-borane complex, a bis(4-fluorophenyl)phosphine-borane complex, a bis(4-dimethylaminophenyl)phosphine-borane complex, a bis(1,3-benzodioxol-5-yl)phosphine-borane complex, a bis(4-chlorophenyl)phosphine-borane complex, a bis(3,5-dimethyl-4-methoxyphenyl)phosphine-borane complex, a bis(4-tert-butylphenyl)phosphine-borane complex, a bis(3-methylphenyl)phosphine-borane complex, a bis(3,5-di-tert-butylphenyl)phosphine-borane complex and the like.

As the "amine" to be used in the present invention, for example, amines such as 1,4-diazabicyclo[2.2.2]octane (abbreviated as DABCO), triethylamine, diisopropylethylamine, tri(n-propyl)amine, tri(n-butyl)amine, 1,8-diazabicyclo[5.4.0]-7-undecene (abbreviated as DBU), tetramethylethylenediamine, dimethylaniline, 1,4-dimethylpiperazine, 1-methylpiperidine, 1-methylpyrrolidine, 4-dimethylaminopyridine, pyridine, diethylamine and the like can be mentioned. Of these, tertiary amines such as 1,4-diazabicyclo[2.2.2]octane, triethylamine, diisopropylethylamine and the like are preferable. Particularly, 1,4-diazabicyclo[2.2.2]octane is preferable.

As the nickel catalyst to be used in the present invention, $NiCl_2$.bis(diphenyl)phosphino $C_{1-4}$ alkane, $NiBr_2$, $NiCl_2$, $NiCl_2$.bis(diphenyl)phosphinyl ferrocene, $NiCl_2$.bis(triphenylphosphine), Ni.tetrakistriphenylphosphine, Ni.tetrakistriphenylphosphite, Ni.dicarbonylbis(triphenyl)phosphine, $NiBr_2$.bis(triphenylphosphine), Ni.bis(1,5-cyclooctadiene), Ni.bis(cyclopentadienyl), Ni.bis(ethylcyclopentadienyl), $NiCl_2$.dimethoxyethane, $Ni(BF_4)_2$ or $Ni(PF_3)_4$ and the like can be mentioned.

Of these, $NiCl_2$.bis(diphenyl)phosphino $C_{1-4}$ alkane, $NiBr_2$, $NiCl_2$, $NiCl_2$.bis(diphenyl)phosphinyl ferrocene, $NiCl_2$.bis(triphenylphosphine), Ni.tetrakistriphenylphosphine, Ni.tetrakistriphenylphosphite or Ni.dicarbonylbis(triphenyl)phosphine and the like are preferable.

Specifically, $NiCl_2$.bis(diphenyl)phosphino $C_{1-4}$alkane and the like are preferable, and $NiCl_2$.bis(diphenyl)phosphinoethane is particularly preferable.

Specific examples of compound (I) include 2,2'-bis[bis(3,5-dimethylphenyl)phosphino]-1,1'-binaphthyl, 2,2'-bis[bis (4-methoxyphenyl)phosphino]-1,1'-binaphthyl, 2,2'-bis[bis(4-dimethylaminophenyl)phosphino]-1,1'-binaphthyl, 2,2'-bis[bis(4-fluorophenyl)phosphino]-1,1'-binaphthyl, 2,2'-bis[bis(3,5-di-tert-butyl-4-methoxyphenyl)phosphino]-1,1'-binaphthyl, 2,2'-bis(diphenylphosphino)-1,1'-binaphthyl, 2,2'-bis[bis(2-methylphenyl)phosphino]-1,1'-binaphthyl, 2,2'-bis[bis(3-methylphenyl)phosphino]-1,1'-binaphthyl, 2,2'-bis[bis(4-methylphenyl)phosphino]-1,1'-binaphthyl, 2,2'-bis[bis(4-tert-butylphenyl)phosphino]-1,1'-binaphthyl, 2,2'-bis[bis(3,5-di-tert-butylphenyl)phosphino]-1,1'-binaphthyl, 2,2'-bis[bis(4-methoxy-3,5-dimethylphenyl)phosphino]-1,1'-binaphthyl, 2,2'-bis[bis(4-chlorophenyl)phosphino]-1,1'-binaphthyl, 2,2'-bis[bis(1,3-benzodioxol-5-yl)phosphino]-1,1'-binaphthyl, 2,2'-bis[bis(2-naphthyl)phosphino]-1,1'-binaphthyl, 2,2'-bis(diphenylphosphino)-6,6'-diphenyl-1,1'-binaphthyl, 2,2'-bis(diphenylphosphino)-7,7'-dimethoxy-1,1'-binaphthyl and the like. The abovementioned compounds include an (R) form, an (S) form and a mixture of an (R) form and an (S) form (the ratio of the two is not limited). As the optically active compound (I), for example, (R)-2,2'-bis(diphenylphosphino)-1,1'-binaphthyl means a compound represented by the formula

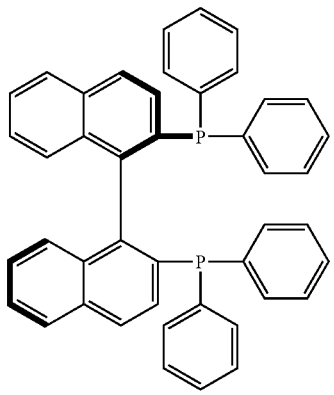

and (S)-2,2'-bis(diphenylphosphino)-1,1'-binaphthyl means a compound represented by the formula

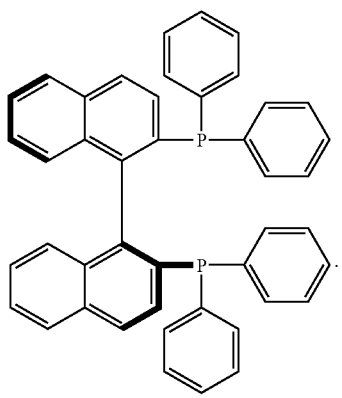

As salts of compound (I), compound (II) and compound (III), for example, salts with inorganic acids (e.g., hydrochloric acid, hydrobromic acid, nitric acid, sulfuric acid, phosphoric acid and the like), or salts with organic acids (e.g., formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid and the like) and the like are used. When compound (I), compound (II) and compound (III) have an acidic group such as a carboxyl group and the like, salts with inorganic base (e.g., alkali metal or alkaline earth metals such as sodium, potassium, calcium, magnesium and the like, ammonia and the like), or salts with organic base (e.g., trimethylamine, triethylamine, pyridine, picoline, ethanolamine, diethanolamine, triethanolamine, dicyclohexylamine, N,N'-dibenzylethylenediamine and the like) and the like are used.

Of compounds (III), a phosphine-borane complex represented by the formula

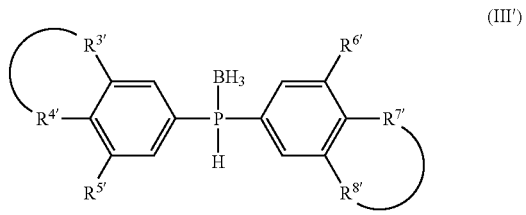

(III')

wherein $R^{3'}$, $R^{5'}$, $R^{6'}$ and $R^{8'}$ are each a hydrogen atom, a lower alkyl group or a lower alkoxy group, and $R^{4'}$ and $R^{7'}$ are each a hydrogen atom, a fluorine atom, a chlorine atom, a $C_{2-6}$ alkyl group, a lower alkoxy group, a mono-lower alkylamino group or a di-lower alkylamino group ($R^{3'}$ and $R^{4'}$ and $R^{7'}$ and $R^{8'}$ may form a lower alkylenedioxy group) (provided that $R^{3'}$, $R^{4'}$, $R^{5'}$, $R^{6'}$, $R^{7'}$ and $R^{8'}$ are not hydrogen atoms at the same time), and a salt thereof [hereinafter sometimes to be abbreviated as compound (III')] and a phosphine-borane complex represented by the formula

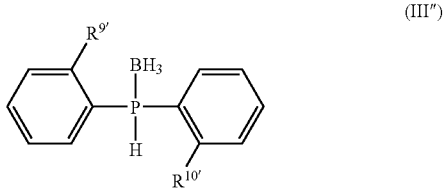

(III")

wherein $R^{9'}$ and $R^{10'}$ are each a lower alkyl group, and a salt thereof [hereinafter sometimes to be abbreviated as compound (III")] are novel compounds.

In compound (III'), the "lower alkyl group" for $R^{3'}$, $R^{5'}$, $R^{6'}$ or $R^{8'}$ is a $C_{1-6}$ alkyl group and, for example, methyl, ethyl, propyl, isopropyl, butyl, isobutyl, sec-butyl, tert-butyl, pentyl, hexyl and the like can be mentioned.

In compound (III'), the "lower alkoxy group" for $R^{3'}$, $R^{5'}$, $R^{6'}$ or $R^{8'}$ is a $C_{1-6}$ alkoxy group and, for example, methoxy, ethoxy, propoxy, isopropoxy, butoxy, isobutoxy, sec-butoxy, tert-butoxy, pentoxy, hexyloxy and the like can be mentioned.

In compound (III'), as the "$C_{2-6}$ alkyl group" for $R^{4'}$ or $R^{7'}$, for example, ethyl, propyl, isopropyl, butyl, isobutyl, sec-butyl, tert-butyl, pentyl, hexyl and the like can be mentioned. In these, branched $C_{3-6}$ alkyl groups such as isopropyl, isobutyl, sec-butyl, tert-butyl and the like are preferable.

In compound (III'), the "lower alkoxy group" for $R^{4'}$ or $R^{7'}$ is a $C_{1-6}$ alkoxy group and, for example, methoxy, ethoxy, propoxy, isopropoxy, butoxy, isobutoxy, sec-butoxy, tert-butoxy, pentoxy, hexyloxy and the like can be mentioned.

In compound (III'), the "mono-lower alkylamino group" for $R^{4'}$ or $R^{7'}$ is a mono-$C_{1-6}$ alkylamino group and, for example, methylamino, ethylamino, propylamino, isopropylamino, butylamino, isobutylamino, sec-butylamino, tert-butylamino, pentylamino, hexylamino and the like can be mentioned.

In compound (III'), the "di-lower alkylamino group" for $R^{4'}$ or $R^{7'}$ is a di-$C_{1-6}$ alkylamino group and, for example, dimethylamino, diethylamino, dipropylamino, diisopropylamino, dibutylamino, diisobutylamino and the like can be mentioned.

In compound (III'), the "lower alkylenedioxy group" formed by $R^{3'}$ and $R^{4'}$, or $R^{7'}$ and $R^{8'}$ is exemplified by —OCH$_2$O—, —OCH$_2$CH$_2$O—, —OCH$_2$CH$_2$CH$_2$O—, —OCH$_2$CH$_2$CH$_2$CH$_2$O— and the like. Of these, —OCH$_2$O— and —OCH$_2$CH$_2$O— are preferable.

As the compounds preferable as compound (III'),
(i) a compound wherein $R^{3'}$, $R^{5'}$, $R^{6'}$ and $R^{8'}$ are each a lower alkyl group ($C_{1-6}$ alkyl group), and $R^{4'}$ and $R^{7'}$ are each a hydrogen atom,
(ii) a compound wherein $R^{3'}$, $R^{5'}$, $R^{6'}$ and $R^{8'}$ are each a lower alkyl group ($C_{1-6}$ alkyl group), and $R^{4'}$ and $R^{7'}$ are each a lower alkoxy group ($C_{1-6}$ alkoxy group),
(iii) a compound wherein $R^{3'}$, $R^{5'}$, $R^{6'}$ and $R^{8'}$ are each a hydrogen atom, and $R^{4'}$ and $R^{7'}$ are each a fluorine atom or a chlorine atom,
(iv) a compound wherein $R^{3'}$, $R^{5'}$, $R^{6'}$ and $R^{8'}$ are each a hydrogen atom, and $R^{4'}$ and $R^{7'}$ are each a lower alkoxy group ($C_{1-6}$ alkoxy group) and
(v) a compound wherein $R^{3'}$, $R^{5'}$, $R^{6'}$ and $R^{8'}$ are each a hydrogen atom, and $R^{4'}$ and $R^{7'}$ are each a di-lower alkylamino group (di-$C_{1-6}$ alkylamino group), salts thereof and the like can be mentioned.

In addition,
(vi) a compound wherein $R^{5'}$ and $R^{8'}$ are each a hydrogen atom, and $R^{3'}$ and $R^{4'}$, and $R^{7'}$ and $R^{8'}$ each form a methylenedioxy group,
(vii) a compound wherein $R^{3'}$, $R^{5'}$, $R^{6'}$ and $R^{8'}$ are each a hydrogen atom, and $R^{4'}$ and $R^{7'}$ are each a $C_{2-6}$ alkyl group, and
(viii) a compound wherein $R^{4'}$, $R^{5'}$, $R^{7'}$ and $R^{8'}$ are each a hydrogen atom, and $R^{3'}$ and $R^{6'}$ are each a lower alkyl group ($C_{1-6}$ alkyl group) are also preferable.

More specifically, a bis(3,5-dimethylphenyl)phosphine-borane complex, a bis(3,5-di-tert-butyl-4-methoxyphenyl)phosphine-borane complex, a bis(4-fluorophenyl)phosphine-borane complex, a bis(4-methoxyphenyl)phosphine-borane complex, a bis(4-dimethylaminophenyl)phosphine-borane complex, a bis(1,3-benzodioxol-5-yl)phosphine-borane complex, a bis(4-chlorophenyl)phosphine-borane complex, a bis(4-methoxy-3,5-dimethylphenyl)phosphine-borane complex, a bis(4-tert-butylphenyl)phosphine-borane complex, a bis(3-methylphenyl)phosphine-borane complex, a bis(3,5-di-tert-butylphenyl)phosphine-borane complex and the like are preferable.

In compound (III"), the "lower alkyl group" for $R^{9'}$ or $R^{10'}$ is a $C_{1-6}$ alkyl group and, for example, methyl, ethyl, propyl, isopropyl, butyl, isobutyl, sec-butyl, tert-butyl, pentyl, hexyl and the like can be mentioned.

Specific examples of compound (III") include a bis(2-methylphenyl)phosphine-borane complex and the like.

As the salts of compound (III') and compound (III"), those similar to the salts of the aforementioned compound (I), compound (II) and compound (III) can be mentioned.

The production method of the present invention comprises reacting compound (II) with compound (III) in a solvent in the presence of an amine and a nickel catalyst to give compound (I).

The amount of compound (III) to be used is about 2 to 5 mol, preferably about 2 to 3 mol, per 1 mol of compound (II).

The amount of the amine to be used is about 2 to 10 mol, preferably about 2 to 8 mol, per 1 mol of compound (II).

The amount of the nickel catalyst to be used is about 0.01 to 10 mol, preferably about 0.05 to 1 mol, per 1 mol of compound (II).

The aforementioned reaction can be carried out in an inert organic solvent. As the organic solvent, hydrocarbons (e.g., hexane, pentane, cyclohexane etc.), amides (e.g., N,N-dimethylformamide (DMF), N,N-dimethylacetamide, N-methylpyrrolidone, 1,3-dimethyl-2-imidazolidinone etc.), aromatic hydrocarbons (e.g., toluene, benzene, chlorobenzene etc.), aliphatic esters (e.g., ethyl acetate, n-propyl acetate, n-butyl acetate etc.), ethers (e.g., diisopropyl ether, diethyl ether, tetrahydrofuran (THF), 1,4-dioxane, 1,2-dimethoxyethane etc.), halogenated hydrocarbons (e.g., chloroform, dichloromethane, 1,2-dichloroethane, carbon tetrachlorides etc.), alcohols (e.g., methanol, ethanol, isopropanol, tert-butanol etc.), ketones (e.g., acetone, ethyl methyl ketone etc.), sulfoxides (e.g., dimethyl sulfoxide etc.), nitriles (e.g., acetonitrile, propionitrile etc.), phosphoric acid amides (e.g., hexamethylphosphoric acid amide etc.) and the like can be mentioned. These solvents may be used alone or in the form of a mixed solvent. Preferable solvents are amides, sulfoxides, phosphoric acid amides and the like. More preferred are amides (N,N-dimethylformamide (DMF), N,N-dimethylacetamide, N-methylpyrrolidone, 1,3-dimethyl-2-imidazolidinone).

The reaction temperature of the reaction is about 30 to 180° C., preferably about 80 to 120° C. The reaction time of the reaction is about 1 to 240 hrs., preferably about 24 to 168 hrs.

The product can be also isolated from a reaction mixture according to conventional methods, and easily purified by separation means such as recrystallization, distillation, chromatography and the like.

The compound (II) can be produced according to a method known per se, such as the methods described in, for example, *Tetrahedron Letters*, vol. 31, p. 985 (1990), *Journal of Organic Chemistry*, vol. 58, p. 1945 (1993) and the like. The compound (II) thus obtained may be used for the reaction with compound (III) in the form of a reaction mixture without isolation.

The compound (III) can be produced by reacting phosphine oxide having substituent(s), which is obtained according to the method described in *Journal of Organic Chemistry*, vol. 33, p. 3690 (1968), in the presence of cerium chloride, sodium borohydride and lithium aluminum hydride

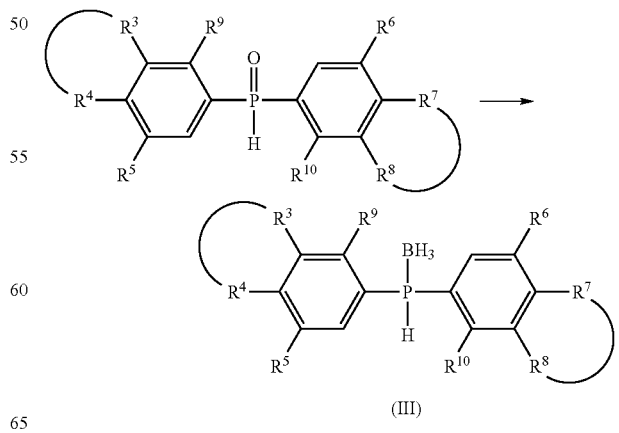

wherein each symbol is as defined above.

The amount of cerium chloride to be used is about 1 to 6 mol, preferably about 3 to 5 mol, per 1 mol of phosphine oxide.

The amount of sodium borohydride to be used is about 2 to 10 mol, preferably about 3 to 5 mol, per 1 mol of phosphine oxide.

The amount of lithium aluminum hydride to be used is about 0.25 to 5 mol, preferably about 1 to 3 mol, per 1 mol of phosphine oxide.

The aforementioned reaction can be carried out in an inert organic solvent. As the organic solvent, hydrocarbons (e.g., hexane, pentane, cyclohexane etc.), amides (e.g., N,N-dimethylformamide (DMF), N,N-dimethylacetamide, N-methylpyrrolidone, 1,3-dimethyl-2-imidazolidinone etc.), aromatic hydrocarbons (e.g., toluene, benzene, chlorobenzene etc.), ethers (e.g., diisopropyl ether, diethyl ether, tetrahydrofuran (THF), 1,4-dioxane, 1,2-dimethoxyethane etc.), phosphoric acid amides (e.g., hexamethylphosphoric acid amide etc.) and the like can be mentioned. These solvents may be used alone or in the form of a mixed solvent. Preferable solvents are ethers, hydrocarbons, aromatic hydrocarbons and the like. More preferable solvents are ethers (e.g., diisopropyl ether, diethyl ether, tetrahydrofuran (THF), 1,4-dioxane, 1,2-dimethoxyethane and the like).

The reaction temperature of the reaction is about −20 to 50° C., preferably about −10 to 35° C. The reaction time of the reaction is about 1 to 48 hrs., preferably about 1 to 20 hrs.

It is also possible to react phosphine having substituent(s) with diborane according to the method described in U.S. Pat. No. 2,926,194 to give compound (III).

The product can be also isolated from a reaction mixture according to conventional methods, and easily purified by separation means such as recrystallization, distillation, chromatography and the like.

The compound (III) thus obtained may be used for the reaction with compound (II) in the form of a reaction mixture without isolation.

By performing the reactions under the aforementioned conditions, compound (I) can be produced without isomerizing the structure of compound (II). That is, in the present invention, if an optical isomer of either an (R) form or an (S) form of optically active compound (II) is appropriately selected, an optical isomer of the object compound (I) can be selectively obtained. For example, when an (R) form of compound (II) is used, an (R) form of compound (I) can be produced efficiently, and when an (S) form of compound (II) is used, an (S) form of compound (I) can be produced efficiently.

The compound (I) obtained by the production method of the present invention, particularly an optical isomer thereof, can be used for the asymmetric synthesis reaction (e.g., asymmetric reduction of carbon-carbon double bond, asymmetric reduction of β-keto ester etc.) for the production of a compound useful as an optically active pharmaceutical product (e.g., a drug for the prophylaxis or treatment of increased urinary frequency or urinary incontinence, a drug for the prophylaxis or treatment of Alzheimer's disease, a drug for the prophylaxis or treatment of hyperlipidemia etc.) or an intermediate therefor, by forming a complex (e.g., a complex can be formed according to the method described in JP-A-H3-255090, JP-A-H9-124669 or a method analogous thereto) with a transition metal (e.g., ruthenium, iridium, palladium, nickel, rhodium etc.). This complex shows superior stereoselective rate, chemical yield, catalytic property and the like in the above-mentioned asymmetric synthesis reaction.

For example, the reduction reaction of the compound to be reduced is carried out in the co-presence of compound (I) obtained by the production method of the present invention, whereby a compound useful as an intermediate for a pharmaceutical product can be obtained with superior stereoselectivity. Particularly, the reduction reaction of α,β-unsaturated ester is carried out in the co-presence of 2,2'-bis[bis(3,5-di-tert-butyl-4-methoxyphenyl)phosphino]-1,1'-binaphthyl or a salt thereof, from among compounds (I), whereby superior stereoselectivity, chemical yield and catalytic property can be achieved.

The present invention is explained in more detail in the following by way of Examples and Reference Examples, which are not to be construed as limitative. In the specification, room temperature means 10° C. to 35° C. For the measurement of each property in Examples, the following instruments were used. $^1$H nuclear magnetic resonance spectrum ($^1$H-NMR): DPX300 (manufactured by Bruker), internal standard substance: tetramethylsilane. $^{13}$C nuclear magnetic resonance spectrum ($^{13}$C-NMR): DPX300 (manufactured by Bruker), internal standard substance: CDCl$_3$. $^{31}$P nuclear magnetic resonance spectrum ($^{31}$P-NMR): DPX300 (manufactured by Bruker), external standard substance: 85% aqueous H$_3$PO$_4$ solution. Mass spectrometry: JMS-700T (manufactured by JEOL). melting point: 530 (manufactured by Buchi).

EXAMPLES

Reference Example 1

(S)-2,2'-bis(trifluoromethanesulfonyloxy)-1,1'-binaphthyl

To a solution of (S)-1,1'-bi-2-naphthol (26.2 g, 91 mmoL) in acetonitrile (130 mL) was added pyridine (19.5 g, 2.7 equivalents) at room temperature. Then, trifluoromethanesulfonic anhydride (64.2 g, 2.5 equivalents) was added at 5° C., and the mixture was stirred at 5 to 10° C. for 2 hrs. Water (100 mL) was added at 3° C., and ethyl acetate (130 mL) was added, and the mixture was stirred at room temperature for 30 min. The reaction mixture was partitioned, and the organic layer was washed with water (50 mL) and concentrated under reduced pressure. To the residue were added diisopropyl ether (150 mL) and activated carbon (0.25 g) and the mixture was stirred at 60° C. for 30 min. The activated carbon was filtered off and the filtrate was concentrated under reduced pressure. The residue was recrystallized from heptane to give the title compound (48.9 g, white crystals). yield 97%

$^1$H-NMR (300 MHz, CDCl$_3$, TMS) δ: 7.33 (d, 2H, J=8.14 Hz), 7.34-7.46 (m, 2H), 7.57-7.63 (m, 2H), 7.68 (d, 2H, J=9.09 Hz), 8.03 (d, 2H, J=8.23 Hz), 8.16 (d, 2H, J=9.08 Hz).

Reference Example 2 bis(3,5-dimethylphenyl)phosphine oxide

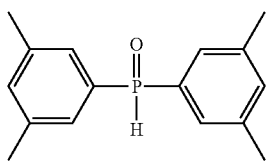

(Production Method 1)

Under an Argon Atmosphere, a Solution of Magnesium (25 g, 0.95 equivalent) and a small amount of iodine in THF (250 mL) was stirred at room temperature for 1 hr. 5-Bromo-m-xylene (200 g, 1.08 moL) was added at 48° C., and the mixture was stirred at 5° C. for 1 hr. Diethyl phosphite (78.3 g, 0.52 equivalent) was added at 5° C., and the mixture was stirred at 5° C. for 2 hrs. Water (200 mL) was added at 3° C., and toluene (200 mL) and 6M-HCl (160 mL) were added. The mixture was stirred at room temperature for 30 min. The reaction mixture was partitioned, and the organic layer was washed successively with water (100 mL), 5% aqueous $NaHCO_3$ solution (100 mL) and 5% aqueous NaCl-solution (100 mL). The organic layer was dried over anhydrous magnesium sulfate and filtered by gravity. The filtrate was concentrated under reduced pressure and the residue was recrystallized from diisopropyl ether-heptane to give the title compound (43.3 g, white crystals). yield 33.3%.

(Production Method 2)

Under a nitrogen stream, a solution of magnesium (3.28 g, 4.01 equivalents), a small amount of iodine and 1,2-dibromo-ethane in THF (10 mL) was stirred at room temperature for 1.5 hrs. A solution of 5-bromo-m-xylene (25.2 g, 4.05 equivalents) in THF (100 mL) was added at 25° C., and the mixture was stirred at 40° C. for 40 min. A solution of diethyl phosphite (4.64 g, 33.6 mmol) in THF (5 mL) was added at −33° C., and the mixture was stirred at 0° C. for 30 min. Water (30 mL) was added at 3° C., and 6M-HCl (20 mL) and toluene (50 mL) were added. The mixture was stirred at room temperature for 30 min. The reaction mixture was partitioned, and the organic layer was washed with 10% aqueous $NaHCO_3$ solution (30 mL), and the organic layer was concentrated under reduced pressure. The residue was recrystallized from heptane and dried (reduced pressure, 50° C.) to give the title compound (6.80 g, white powder). yield 78.3%. melting point: 82.4° C.

$^1$H-NMR (300 MHz, $CDCl_3$, TMS) δ: 2.35 (s, 12H), 7.18 (s, 2H), 7.28 (s, 2H), 7.33 (s, 2H), 7.94 (d, 1H, $J_{H-P}$=477.0 Hz).

$^{31}$P-NMR (121 MHz, $CDCl_3$, 85% $H_3PO_4$) δ: 23.89 (d, quint, $J_{H-P}$=477.1 Hz, $J_{HCC-P}$=13.7 Hz).

Reference Example 3 bis(4-methoxyphenyl)phosphine oxide

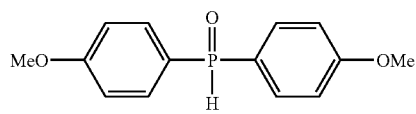

Under an argon atmosphere, a solution of magnesium (6.5 g, 1.0 equivalent) and a small amount of iodine in THF (65 mL) was stirred at room temperature for 1 hr. 4-Bromoanisole (50 g, 0.27 moL) was added at 42° C., and the mixture was stirred at 5° C. for 1 hr. Then, diethyl phosphite (18.4 g, 0.50 equivalent) was added at 15 to 20° C., and the mixture was stirred at 5° C. for 1 hr. Water (60 mL) was added at 3° C., and toluene (120 mL) and 6M-HCl (60 mL) were added. The mixture was stirred at room temperature for 30 min. The reaction mixture was partitioned, and the aqueous layer was extracted 3 times with toluene (60 mL). The combined organic layer was dried over anhydrous magnesium sulfate, filtered by gravity, and the filtrate was concentrated under reduced pressure. The residue was recrystallized from diisopropyl ether to give the title compound (18.9 g, white crystals). yield 54.1%. melting point: 126.0° C.

$^1$H-NMR (300 MHz, $CDCl_3$, TMS) δ: 3.85 (s, 6H), 6.99 (d, 2H, J=8.79 Hz), 7.00 (d, 2H, J=8.73 Hz), 7.61 (dd, 4H, J=8.73 Hz, 13.13 Hz), 8.02 (d, 1H, J=477.2 Hz).

$^{31}$P-NMR (121 MHz, $CDCl_3$, 85% $H_3PO_4$) δ: 21.21 (dquint, J=474.1 Hz, 13.0 Hz).

Elemental Analysis for $C_{14}H_{15}O_3P$ Calculated; C, 64.12; H, 5.77; P, 11.81. Found; C, 64.12; H, 5.89; P, 11.78.

Reference Example 4 bis(4-dimethylaminophenyl)phosphine oxide

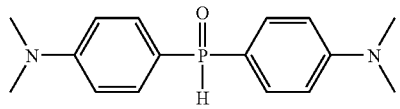

Under an argon atmosphere, a solution of magnesium (3.0 g, 1.0 equivalent) and a small amount of iodine in THF (30 mL) was stirred at room temperature for 1 hr. 4-Bromo-N,N-dimethylaniline (25 g, 0.125 moL) was added at 45° C., and the mixture was stirred at 5° C. for 1 hr. Then, diethyl phosphite (8.63 g, 0.50 equivalent) was added at 5° C., and the mixture was stirred at 5° C. for 1 hr. Water (30 mL) was added at 3° C., and then toluene (60 mL) and 6M-HCl (30 mL) were added. The mixture was stirred at room temperature for 30 min. The reaction mixture was partitioned, and the aqueous layer was neutralized with NaOH and extracted with THF (30 mL). The combined organic layer was dried over anhydrous magnesium sulfate, filtered by gravity, and the filtrate was concentrated under reduced pressure. The residue was recrystallized from diisopropyl ether to give the title compound (9.53 g, slightly brown white crystals). yield 52.9%. melting point: 152.1° C.

$^1$H-NMR (300 MHz, $CDCl_3$, TMS) δ: 3.01 (s, 12H), 6.71 (d, 2H, J=8.94 Hz), 6.72 (d, 2H, J=8.94 Hz), 7.48 (d, 2H, J=8.91 Hz), 7.52 (d, 2H, J=8.88 Hz), 7.96 (d, 1H, J=470.1 Hz).

$^{31}$P-NMR (121 MHz, $CDCl_3$, 85% $H_3PO_4$) δ: 22.78 (dquint, J=469.2 Hz, 12.7 Hz).

Elemental Analysis for $C_{16}H_{21}N_2OP$ Calculated; C, 66.65; H, 7.34; N, 9.72; P, 10.74. Found; C, 66.56; H, 7.43; N, 9.57; P, 10.79.

Reference Example 5 bis(4-fluorophenyl)phosphine oxide

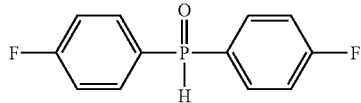

Under an argon atmosphere, a solution of magnesium (6.95 g, 1.0 equivalent) and a small amount of iodine in THF (70 mL) was stirred at room temperature for 1 hr. 1-Bromo-4-fluorobenzene (50 g, 0.286 moL) was added at 40° C., and the mixture was stirred at 3° C. for 1 hr. Then, diethyl phosphite (19.7 g, 0.50 equivalents) was added at 13 to 19° C., and the mixture was stirred at 5° C. for 1 hr. Water (45 mL) was added at 4° C., and toluene (150 mL) and 6M-HCl (45 mL) were added. The mixture was stirred at room temperature for 30 min. The reaction mixture was partitioned, and the organic layer was washed successively with water, 5% aqueous NaHCO$_3$ solution (50 mL), and 5% aqueous NaCl solution (50 mL). The organic layer was dried over anhydrous magnesium sulfate, filtered by gravity, and the filtrate was concentrated under reduced pressure. The residue was purified by column chromatography (silica gel 30 g, n-hexane/ethyl acetate=1/0→3/1) to give the title compound (12.0 g, pale-red oil). yield 35.2%.

$^1$H-NMR (300 MHz, CDCl$_3$, TMS) δ: 7.01-7.03 (m, 4H), 7.64-7.74 (m, 4H), 8.08 (d, 1H, J=485.8 Hz).

$^{31}$P-NMR (121 MHz, CDCl$_3$, 85% H$_3$PO$_4$) δ: 19.39 (dquint, J=485.7 Hz, 13.3 Hz).

Reference Example 6

4-bromo-2,6-di-tert-butylanisole

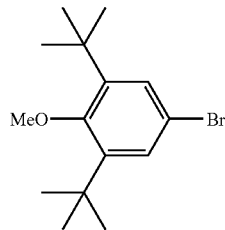

Under an argon atmosphere, to a solution of 4-bromo-2,6-di-tert-butylphenol (50 g, 0.175 moL) and potassium carbonate (96.7 g, 4.0 equivalents) in acetone (750 mL) was added dimethyl sulfate (38.6 g, 1.75 equivalents) at 22° C., and the mixture was stirred under reflux for 13 hrs. Insoluble materials were filtered off and the solvent was evaporated under reduced pressure. Ethylacetate (150 mL) and water (100 mL) were added, the mixture was partitioned, and the organic layer was washed successively with water (100 mL), 5% aqueous NaHCO$_3$ solution (100 mL) and 5% aqueous NaCl solution (100 mL). The organic layer was dried over anhydrous magnesium sulfate, filtered by gravity, and the filtrate was concentrated under reduced pressure to give the title compound (56.1 g, brown oil). yield 95.2%

$^1$H-NMR (300 MHz, CDCl$_3$, TMS) δ: 1.41 (s, 18H), 3.68 (s, 3H), 7.33 (s, 2H).

Reference Example 7 bis(3,5-di-tert-butyl-4-methoxyphenyl)phosphine oxide

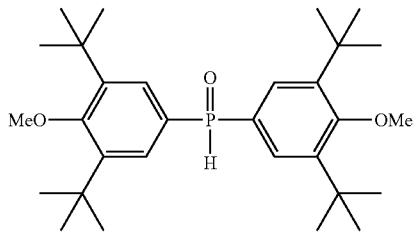

Under an argon atmosphere, a solution of magnesium (4.0 g, 0.95 equivalent) and a small amount of iodine in THF (50 mL) was stirred at room temperature for 1 hr. 4-Bromo-2,6-di-tert-butylanisole (52 g, 0.175 moL) synthesized in Reference Example 6 was added at 46° C. to 53° C., and the mixture was stirred at 5° C. for 1 hr. Then, diethyl phosphite (11.4 g, 0.52 equivalents) was added at 5° C., and the mixture was stirred at 5° C. for 1 hr. Water (50 mL) was added at 3° C. and then toluene (50 mL) and 6M-HCl (20 mL) were added. The mixture was stirred at room temperature for 30 min. The reaction mixture was partitioned, and the organic layer was washed successively with water (20 mL), 5% aqueous NaHCO$_3$ solution (20 mL) and 5% aqueous NaCl solution (20 mL). The organic layer was dried over anhydrous magnesium sulfate, filtered by gravity, and the filtrate was concentrated under reduced pressure. The residue was recrystallized from heptane to give the title compound (11.6 g, pale-yellow white crystals). yield 20.5%. melting point: 166.1° C.

$^1$H-NMR (300 MHz, CDCl$_3$, TMS) δ: 1.38 (s, 36H), 3.68 (s, 6H), 7.49 (s, 2H), 7.54 (s, 2H), 8.01 (d, 1H, J=474.4 Hz).

$^{31}$P-NMR (121 MHz, CDCl$_3$, 85% H$_3$PO$_4$) δ: 23.57 (dquint, J=474.1 Hz, 14.0 Hz).

Elemental Analysis for C$_{30}$H$_{47}$O$_3$P Calculated; C, 74.04; H, 9.73; P, 6.36. Found; C, 74.13; H, 9.93; P, 6.20.

Reference Example 8 bis(4-methylphenyl)phosphine oxide

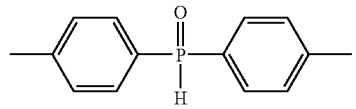

Under an argon atmosphere, a solution of magnesium (3.55 g, 1.0 equivalent) and a small amount of iodine in THF (30 mL) was stirred at room temperature for 1 hr. A solution of p-tolyl bromide (25 g, 0.146 moL) in THF (5 mL) was added at 30° C. The mixture was stirred at 45° C. for 30 min. and then at 5° C. for 1 hr. Diethyl phosphite (10.08 g, 0.5 equivalent) was added at 5° C. and the mixture was stirred at 5° C. for 1 hr and at room temperature (25° C.) for 30 min. Water (10 mL) was added at 3° C., and then toluene (40 mL) and 6M-HCl (20 mL) were added. The mixture was stirred at room temperature for 30 min. The reaction mixture was partitioned, and the organic layer was washed successively with water (10 mL), 5% aqueous NaHCO$_3$ solution (10 mL) and 5% aqueous NaCl solution (10 mL). The organic layer was dried over anhydrous magnesium sulfate, filtered by gravity, and the filtrate was concentrated under reduced pressure. The residue was recrystallized from diisopropyl ether-heptane to give the title compound (7.78 g, white crystals). yield 46.3%. melting point: 93.7° C.

$^1$H-NMR (300 MHz, CDCl$_3$, TMS) δ: 2.41 (s, 6H), 7.26-7.31 (m, 4H), 7.54-7.61 (m, 4H), 8.03 (d, 1H, J=477.5 Hz).

$^{13}$C-NMR (75 MHz, CDCl$_3$, CDCl$_3$) δ: 22.05, 128.22, 129.89, 130.07, 131.06, 131.22, 143.43.

$^{31}$P-NMR (121 MHz, CDCl$_3$, 85% H$_3$PO$_4$) δ: 22.72 (dquint, J=477.1 Hz, 13.8 Hz).

Elemental Analysis for C$_{14}$H$_{15}$OP Calculated; C, 73.03; H, 6.57; P, 13.45. Found; C, 72.80; H, 6.58; P, 13.31.

Reference Example 9 bis(2-methylphenyl)phosphine oxide

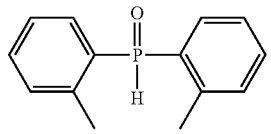

Under an argon atmosphere, a solution of magnesium (3.55 g, 1.0 equivalent) and a small amount of iodine in THF (40 mL) was stirred at room temperature for 1 hr. A solution of o-tolyl bromide (25 g, 0.146 moL) in THF (5 mL) was added at 30° C. After stirring at 40° C. for 30 min., the mixture was stirred at 5° C. for 1 hr. Then, a solution of diethyl phosphite (10.08 g, 0.5 equivalent) in THF (10 mL) was added at 5° C., and the mixture was stirred at 5° C. for 1 hr. Water (20 mL) was added at 3° C., and then toluene (50 mL) and 6M-HCl (20 mL) were added. The mixture was stirred at room temperature for 30 min. The reaction mixture was partitioned, and the organic layer was washed successively with water (10 mL), 5% aqueous $NaHCO_3$ solution (10 mL) and 5% aqueous NaCl solution (10 mL). Then the organic layer was dried over anhydrous magnesium sulfate, filtered by gravity, and the filtrate was concentrated under reduced pressure. The residue was recrystallized from heptane to give the title compound (6.70 g, white crystals). yield 39.9%. melting point: 91.3° C.

$^1$H-NMR (300 MHz, $CDCl_3$, TMS) δ: 2.37 (s, 6H), 7.18-7.26 (m, 2H), 7.29-7.34 (m, 2H), 7.43-7.48 (m, 2H), 7.70 (d, 1H, J=15.06 Hz), 7.72 (d, 1H, J=14.82 Hz), 8.21 (d, 1H, J=476.9 Hz).

$^{13}$C-NMR (75 MHz, $CDCl_3$, $CDCl_3$) δ: 20.59, 126.36, 126.53, 129.04, 130.36, 131.55, 131.69, 132.76, 132.93, 141.44, 141.57.

$^{31}$P-NMR (121 MHz, $CDCl_3$, 85% $H_3PO_4$) δ: 16.66-17.93 (m), 20.26-21.86 (m).

Reference Example 10 bis(4-methoxy-3,5-dimethylphenyl)phosphine oxide

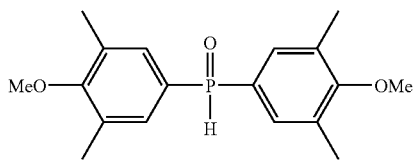

Under an argon atmosphere, a solution of magnesium (2.26 g, 0.95 equivalent), a small amount of iodine and a small amount of 1,2-dibromoethane in THF (25 mL) was stirred at room temperature for 1 hr. A solution of 4-bromo-2,6-dimethylanisole (20 g, 0.093 moL) in THF (10 mL) was added at 20° C. The mixture was stirred at 40° C. for 30 min., and stirred at 5° C. for 30 min. Then, a solution of diethyl phosphite (7.53 g, 0.5 equivalent) in THF (10 mL) was added at 5° C., and the mixture was stirred at 5° C. for 2 hrs. Toluene (50 mL) was added at 3° C., and then 3M-HCl (30 mL) was added. The mixture was stirred at room temperature for 30 min. The reaction mixture was partitioned, and the organic layer was washed successively with water (10 mL), 5% aqueous $NaHCO_3$ solution (10 mL) and 5% aqueous NaCl solution (10 mL). The organic layer was dried over anhydrous magnesium sulfate, filtered by gravity, and the filtrate was concentrated under reduced pressure. The residue was purified by column chromatography (silica gel 20 g, toluene→ethyl acetate) to give the title compound (6.91 g, colorless oil). yield 46.7%.

$^1$H-NMR (300 MHz, $CDCl_3$, TMS) δ: 2.30 (s, 12H), 3.74 (s, 6H), 7.34 (d, 4H, J=13.74 Hz), 7.91 (d, 1H, J=476.8 Hz).

$^{31}$P-NMR (121 MHz, $CDCl_3$, 85% $H_3PO_4$) δ: 22.63 (dquint, J=477.0 Hz, 13.6 Hz).

Reference Example 11 bis(1,3-benzodioxol-5-yl)phosphine oxide

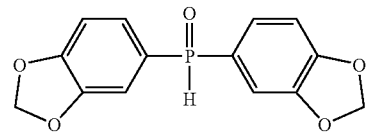

Under an argon atmosphere, a solution of magnesium (3.01 g, 1.0 equivalent), a small amount of iodine and a small amount of 1,2-dibromoethane in THF (30 mL) was stirred at room temperature for 1 hr. A solution of 5-bromo-1,3-benzodioxole (25 g, 0.124 moL) in THF (20 mL) was added at 35° C. and the mixture was stirred at 40° C. for 30 min. and then stirred at 5° C. for 30 min. Then, a solution of diethyl phosphite (10.07 g, 0.5 equivalent) in THF (10 mL) was added at 5° C., and the mixture was stirred at 5° C. for 1 hr. Water (20 mL) was added at 3° C. and then toluene (70 mL) and 6M-HCl (20 mL) were added. The mixture was stirred at room temperature for 30 min. and THF (30 mL) was added. The reaction mixture was partitioned, and the organic layer was washed successively with water (10 mL), 5% aqueous $NaHCO_3$ solution (10 mL) and 5% aqueous NaCl solution (10 mL). The organic layer was dried over anhydrous magnesium sulfate, filtered by gravity, and the filtrate was concentrated under reduced pressure. The residue was recrystallized from diisopropyl ether to give the title compound (7.75 g, white crystals). yield 43.1%. melting point: 127.9° C.

$^1$H-NMR (300 MHz, $CDCl_3$, TMS) δ: 6.01 (s, 4H), 6.90 (dd, 2H, J=7.86 Hz, 2.22 Hz), 7.04 (dd, 2H, J=12.87 Hz, 1.14 Hz), 7.18-7.26 (m, 2H), 7.92 (d, 1H, J=483.0 Hz).

$^{13}$C-NMR (75 MHz, $CDCl_3$, $CDCl_3$) δ: 102.14, 109.31, 109.53, 110.25, 110.44, 124.35, 125.76, 126.52, 126.69, 148.60, 148.85, 151.80.

$^{31}$P-NMR (121 MHz, $CDCl_3$, 85% $H_3PO_4$) δ: 22.59 (dquint, J=483.5 Hz, 13.4 Hz).

Elemental Analysis for $C_{14}H_{11}O_5P$ Calculated; C, 57.94; H, 3.82; P, 10.67. Found; C, 57.88; H, 3.83; P, 10.57.

Reference Example 12 bis(2-naphthyl)phosphine oxide

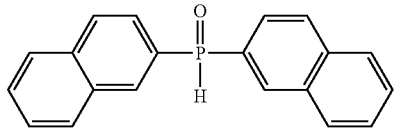

Under an argon atmosphere, a solution of magnesium (2.94 g, 1.0 equivalent), a small amount of iodine and a small amount of 1,2-dibromoethane in THF (30 mL) was stirred at room temperature for 1 hr. A solution of 2-bromonaphthalene (25 g, 0.121 moL) in THF (20 mL) was added at 35°. The mixture was stirred at 40° C. for 30 min. and then stirred at 5° C. for 30 min. Then, a solution of diethyl phosphite (9.77 g, 0.5 equivalent) in THF (10 mL) was added at 5° C., and the mixture was stirred at 5° C. for 3 hrs. Water (20 mL) was added at 3° C. and then toluene (60 mL) and 6M-HCl (20 mL) were added. The mixture was stirred at room temperature for 30 min. The reaction mixture was partitioned, and the organic layer was washed successively with water (10 mL), 5% aqueous NaHCO$_3$ solution (10 mL) and 5% aqueous NaCl solution (10 mL). Then the organic layer was dried over anhydrous magnesium sulfate, filtered by gravity, and the filtrate was concentrated under reduced pressure. The residue was recrystallized from diisopropyl ether-heptane to give the title compound (9.62 g, white crystals). yield 53.0%. melting point: 98.3° C.

$^1$H-NMR (300 MHz, CDCl$_3$, TMS) δ: 7.49-7.64 (m, 6.5H), 7.86-7.95 (m, 6H), 8.40 (d, 2H, J=15.75 Hz), 9.15 (s, 0.5H).
$^{13}$C-NMR (75 MHz, CDCl$_3$, CDCl$_3$) δ: 125.07, 125.23, 127.13, 127.76, 127.93, 128.81, 128.96, 132.43, 132.62, 132.82, 132.96, 135.05.
$^{31}$P-NMR (121 MHz, CDCl$_3$, 85% H$_3$PO$_4$) δ: 22.99 (dquint, J=481.0 Hz, 13.3 Hz).

Reference Example 13 bis(4-chlorophenyl)phosphine oxide

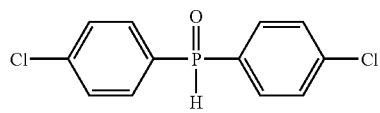

Under an argon atmosphere, to a solution of diethyl phosphite (5.40 g, 0.033 mmoL) in THF (30 mL) was added a 1M solution (100 mL, 3.0 equivalents) of 4-chloromagnesium bromide in diethyl ether at 0° C., and the mixture was stirred at 5° C. for 2 hrs. Water (20 mL) was added at 3° C., and then toluene (80 mL) and 6M-HCl (20 mL) were added. The mixture was stirred at room temperature for 30 min. The reaction mixture was partitioned, and the organic layer was washed successively with water (10 mL), 5% aqueous NaHCO$_3$ solution (10 mL) and 5% aqueous NaCl solution (10 mL). Then the organic layer was dried over anhydrous magnesium sulfate, filtered by gravity, and the filtrate was concentrated under reduced pressure. The residue was recrystallized from heptane to give the title compound (8.70 g, white crystals). yield 97.3%. melting point: 124.0° C.

$^1$H-NMR (300 MHz, CDCl$_3$, TMS) δ: 7.47-7.52 (m, 4H), 7.57-7.65 (m, 4H), 8.05 (d, 1H, J=487.1 Hz).
$^{13}$C-NMR (75 MHz, CDCl$_3$, CDCl$_3$) δ: 129.13, 129.77, 129.95, 130.49, 132.36, 132.53, 139.95.
$^{31}$P-NMR (121 MHz, CDCl$_3$, 85% H$_3$PO$_4$) δ: 17.59-18.54 (m), 21.62-22.70 (m).

Reference Example 14 bis(biphenyl-4-yl)phosphine oxide

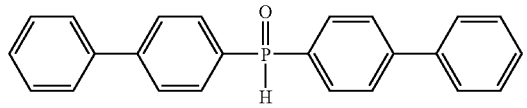

Under an argon atmosphere, a solution of magnesium (2.60 g, 1.0 equivalent), a small amount of iodine and a small amount of 1,2-dibromoethane in THF (20 mL) was stirred at room temperature for 30 min. A solution of 4-bromobiphenyl (25 g, 0.107 moL) in THF (20 mL) was added at 35° C. and the mixture was stirred at 40° C. for 1 hr. and then stirred at 5° C. for 30 min. A solution of diethyl phosphite (7.39 g, 0.5 equivalent) in THF (10 mL) was added at 5° C., and the mixture was stirred at 5° C. for 2 hrs. Toluene (60 mL) was added at 3° C. and 3M-HCl (30 mL) was added. The mixture was stirred at room temperature for 30 min. THF (50 mL) was added, and the reaction mixture was partitioned. The organic layer was washed with 5% aqueous NaCl solution (10 mL). The organic layer was dried over anhydrous magnesium sulfate, filtered by gravity, and the filtrate was concentrated under reduced pressure. The residue was recrystallized from diisopropyl ether to give the title compound (12.47 g, white crystals). yield 65.8%.

$^1$H-NMR (300 MHz, THF-d$_8$, TMS) δ: 7.34-7.43 (m, 7H), 7.57-7.66 (m, 5H), 7.78-7.87 (m, 6H), 8.11 (d, 1H, J=479.3 Hz).
$^{13}$C-NMR (75 MHz, THF-d$_8$, CDCl$_3$) δ: 124.80, 125.06, 125.11, 125.29, 125.99, 126.58, 126.80, 128.95, 129.10.
$^{31}$P-NMR (121 MHz, THF-d$_8$, 85% H$_3$PO$_4$) δ: 16.35 (dquint, J=479.5 Hz, 13.3 Hz).

Reference Example 15 bis(p-tert-butylphenyl)phosphine oxide

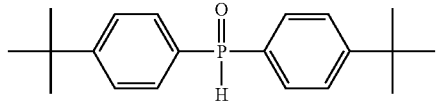

Under a nitrogen stream, a solution of magnesium (3.62 g, 4.0 equivalents) and a small amount of iodine and 1,2-dibromoethane in THF (24 mL) was stirred at room temperature for 30 min. A solution of p-tert-butylbromobenzene (31.62 g, 3.99 equivalents) in THF (130 mL) was added at 24° C., and the mixture was stirred at 40° C. for 30 min. Then, a solution of diethyl phosphite (5.14 g, 37.2 mmol) in THF (8 mL) was added at 21° C., and the mixture was stirred at 22° C. for 30 min. 6M-HCl (20 mL) was added at 4° C., and then water (20 mL) and toluene (60 mL) were added. The mixture was stirred at room temperature for 30 min. The reaction mixture was partitioned, and the organic layer was washed successively with water (20 mL), 10% aqueous NaHCO$_3$ solution (20 mL) and 10% aqueous NaCl solution (20 mL). The organic layer was dried over anhydrous magnesium sulfate, filtered by gravity, and the filtrate was concentrated under reduced pressure. The residue was recrystallized from n-hexane and dried (reduced pressure, 40° C.) to give the title compound (9.17 g, white powder). yield 78.4%. melting point: 142.5° C.

$^1$H-NMR (300 MHz, CDCl$_3$, TMS) δ: 1.33 (s, 18H), 7.50-7.68 (m, 8H), 8.05 (d, 1H, J$_{H-P}$=477.2 Hz).

$^{13}$C-NMR (75 MHz, CDCl$_3$, CDCl$_3$) δ: 31.00, 35.00, 125.88, 127.66, 129.04, 130.47, 130.63, 155.94, 155.98.

$^{31}$P-NMR (121 MHz, CDCl$_3$, 85% H$_3$PO$_4$) δ: 22.32 (d, quint, J$_{H-P}$=478.0 Hz, J$_{HCC-P}$=13.2 Hz).

Elemental Analysis for C$_{20}$H$_{27}$OP Calculated; C, 76.40; H, 8.66, P: 9.85. Found; C, 76.44; H, 8.64, P: 9.53.

Reference Example 16 bis(3,5-di-tert-butylphenyl)phosphine oxide

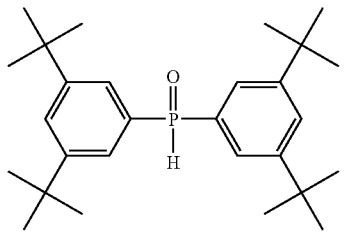

Under a nitrogen stream, a solution of magnesium (1.21 g, 3.61 equivalents) and a small amount of iodine and 1,2-dibromoethane in THF (8 mL) was stirred at room temperature for 1 hr. A solution of 1-bromo-3,5-di-tert-butylbenzene (12.99 g, 3.49 equivalents) in THF (40 mL) was added at 23° C., and the mixture was stirred at 40° C. for 30 min. Then, a solution of diethyl phosphite (1.90 g, 13.8 mmol) in THF (3 mL) was added at 24° C., and the mixture was stirred at 24° C. for 30 min. 6M-HCl (7 mL) was added at 2° C. and then water (7 mL) and toluene (20 mL) were added. The mixture was stirred at room temperature for 30 min. The reaction mixture was partitioned, and the organic layer was washed successively with water (7 mL), 10% aqueous NaHCO$_3$ solution (7 mL) and 10% aqueous NaCl-solution (7 mL). The organic layer was dried over anhydrous magnesium sulfate, filtered by gravity, and the filtrate was concentrated under reduced pressure. The residue was recrystallized from n-hexane and dried (reduced pressure, 40° C.) to give the title compound (3.38 g, white powder). yield 57.5%. melting point: 184.6° C.

$^1$H-NMR (300 MHz, CDCl$_3$, TMS) δ: 1.33 (s, 36H), 7.53 (s, 1H), 7.53 (s, 1H), 7.58 (s, 1H), 7.58 (s, 1H), 7.63 (s, 1H), 7.63 (s, 1H), 8.10 (d, 1H, J$_{H-P}$=474.9 Hz).

$^{13}$C-NMR (75 MHz, CDCl$_3$, CDCl$_3$) δ: 31.23, 35.00, 124.75, 124.91, 126.49, 126.52, 129.96, 131.30, 151.30, 151.46.

$^{31}$P-NMR (121 MHz, CDCl$_3$, 85% H$_3$PO$_4$) δ: 24.94 (d, quint, J$_{H-P}$=474.8 Hz, J$_{HCC-P}$=14.3 Hz).

Elemental Analysis for C$_{28}$H$_{43}$OP Calculated; C, 78.83; H, 10.16, P: 7.26. Found; C, 78.74; H, 9.93, P: 7.16.

Reference Example 17 bis(m-tolyl)phosphine oxide

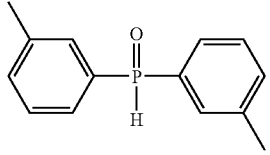

Under a nitrogen stream, a solution of magnesium (3.60 g, 3.50 equivalents) and a small amount of iodine and 1,2-dibromoethane in THF (25 mL) solution was stirred at room temperature for 30 min. A solution of m-bromotoluene (25.36 g, 3.51 equivalents) in THF (130 mL) was added at 24° C., and the mixture was stirred at 40° C. for 30 min. Then, a solution of diethyl phosphite (5.84 g, 42.3 mmol) in THF (10 mL) was added at 25° C., and the mixture was stirred at 24° C. for 1.5 hrs. 6M-HCl (20 mL) was added at 4° C., and then water (20 mL) and toluene (60 mL) were added. The mixture was stirred at room temperature for 30 min. The reaction mixture was partitioned, and the organic layer was washed successively with 10% aqueous NaHCO$_3$ solution (20 mL), water (20 mL) and 10% aqueous NaCl solution (20 mL). The organic layer was dried over anhydrous magnesium sulfate, filtered by gravity, and further passed through a membrane filter (0.2 μm) under reduced pressure. The filtrate was concentrated under reduced pressure to give the title compound (9.09 g, colorless oil). yield 93.3%

$^1$H-NMR (300 MHz, CDCl$_3$, TMS) δ: 2.34 (s, 6H), 7.31-7.54 (m, 8H), 7.97 (d, 1H, J$_{H-P}$=479.3 Hz).

$^{13}$C-NMR (75 MHz, CDCl$_3$, CDCl$_3$) δ: 21.25, 127.53, 127.69, 128.60, 128.78, 130.93, 131.08, 133.25, 133.29, 138.67, 138.84.

$^{31}$P-NMR (121 MHz, CDCl$_3$, 85% H$_3$PO$_4$) δ: 23.25 (d, quint, J$_{H-P}$=479.2 Hz, J$_{HCC-P}$=13.8 Hz).

mass spectrometry (FAB-HR); Calculated; 231.0939 Found; 231.0918 (MH$^+$).

Reference Example 18 bis(4-methylphenyl)phosphine-borane complex

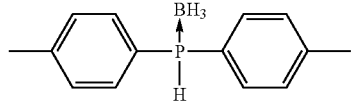

Under an argon atmosphere, a solution of cerium chloride (7.89 g, 3.0 equivalents) in THF (20 mL) was stirred at room temperature (25° C.) for 30 min. Sodium borohydride (1.25 g, 3.1 equivalents) was added, and the mixture was stirred at room temperature for 1 hr. Then bis(4-methylphenyl)phosphine oxide (2.5 g, 0.011 moL) synthesized in Reference Example 8 and lithium aluminum hydride (0.494 g, 1.2 equivalents) were successively added at 5° C., and the mixture was stirred at room temperature for 17 hrs. Water (10 mL) was added at 3° C. and then toluene (20 mL) and 6M-HCl (20 mL) were added. The mixture was stirred at room temperature for 30 min. The reaction mixture was partitioned, and the aqueous layer was extracted with toluene (30 mL). The combined organic layer was washed successively with 5% aqueous NaHCO$_3$ solution (20 mL) and 5% aqueous NaCl solution (20 mL). Then the organic layer was dried over anhydrous magnesium sulfate, filtered by gravity, and the filtrate was concentrated under reduced pressure. The residue was purified by column chromatography (alumina 25 g, n-hexane/ethyl acetate=10/1). The residue was recrystallized from heptane to give the title compound (1.28 g, white crystals). yield 51.0%. melting point: 78.6° C.

$^1$H-NMR (300 MHz, CDCl$_3$, TMS) δ: 0.43-1.61 (m, 3H), 2.38 (s, 6H), 6.26 (dq, 1H, J=377.5 Hz, 6.24 Hz), 7.24-7.27 (m, 4H), 7.51-7.58 (m, 4H).

$^{13}$C-NMR (75 MHz, CDCl$_3$, CDCl$_3$) δ: 21.90, 123.02, 123.81, 130.14, 130.28, 133.22, 133.35, 142.44.

$^{31}$P-NMR (121 MHz, CDCl$_3$, 85% H$_3$PO$_4$) δ: −1.44−−0.16 (m), 1.62-3.19 (m).

Elemental Analysis for C$_{14}$H$_{18}$BP Calculated; C, 73.72; H, 7.95; P, 13.58. Found; C, 73.65; H, 7.93; P, 13.54.

Reference Example 19

(S)-6,6'-dibromo-2,2'-bis(methoxymethyloxy)-1,1'-binaphthyl

To a solution of (S)-6,6'-dibromo-1,1'-bi-2-naphthol (4.0 g, 9.0 mmoL) in dichloromethane (40 mL) was added diisopropylethylamine (3.49 g, 3.0 equivalents) at room temperature (25° C.). Then, chloromethyl methyl ether (1.59 g, 2.2 equivalents) was added at 5° C., and the mixture was stirred at room temperature for 18 hrs. Water (10 mL) was added at 3° C., and the mixture was stirred at room temperature for 30 min. The reaction mixture was partitioned, and the organic layer was washed with 5% aqueous NaCl solution (10 mL). The organic layer was dried over anhydrous magnesium sulfate, filtered by gravity, and the filtrate was concentrated under reduced pressure. The residue was recrystallized from diisopropyl ether to give the title compound (4.28 g, paleyellow white crystals). yield 89.4%.

$^1$H-NMR (300 MHz, CDCl$_3$, TMS) δ: 3.16 (s, 6H), 5.04 (dd, 4H, J=32.32 Hz, 6.85 Hz), 6.98 (d, 2H, J=9.02 Hz), 7.29 (dd, 2H, J=9.03 Hz, 2.01 Hz), 7.60 (d, 2H, J=9.07 Hz), 7.87 (d, 2H, J=9.08 Hz), 8.04 (d, 2H, J=1.93 Hz).

Reference Example 20

(S)-2,2'-bis(methoxymethyloxy)-6,6'-diphenyl-1,1'-binaphthyl

To a solution of (S)-6,6'-dibromo-2,2'-bis(methoxymethyloxy)-1,1'-binaphthyl (2.0 g, 3.76 mmoL) in dimethoxyethane (20 mL) were added dihydroxyphenylborane (1.37 g, 3.0 equivalents), tetrakistriphenylphosphine palladium (0.43 g, 0.1 equivalent) and aqueous sodium carbonate (1.99 g, 3.0 equivalents) solution (2 mL) at room temperature (25° C.). The mixture was stirred under reflux for 8 hrs. Water (10 mL) and ethyl acetate (20 mL) were added at 3° C., and the mixture was stirred at room temperature for 30 min. The reaction mixture was partitioned, and the organic layer was washed with 5% aqueous NaCl solution (10 mL). The organic layer was dried over anhydrous magnesium sulfate, filtered by gravity, and the filtrate was concentrated under reduced pressure. The residue was purified by column chromatography (silica gel 25 g, n-hexane/ethyl acetate=5/1). Effective fraction was concentrated under reduced pressure to give the title compound (1.63 g, yellow amorphous form). yield 82.2%.

$^1$H-NMR (300 MHz, CDCl$_3$, TMS) δ: 3.22 (s, 6H), 5.10 (dd, 4H, J=29.74 Hz, 6.77 Hz), 7.29-7.39 (m, 4H), 7.45-7.57 (m, 6H), 7.63-7.73 (m, 6H), 8.05 (d, 2H, J=9.00 Hz), 8.12 (d, 2H, J=1.66 Hz).

Reference Example 21

(S)-6,6'-diphenyl-2,2'-bis(trifluoromethanesulfonyloxy)-1,1'-binaphthyl

To a solution of (S)-2,2'-bis(methoxymethyloxy)-6,6'-diphenyl-1,1'-binaphthyl (1.63 g, 3.08 mmoL) in THF (5 mL) was added 6M aqueous HCl solution (5 mL), and the mixture was stirred under reflux for 7 hrs. 30% Aqueous NaOH solution and ethyl acetate (20 mL) were added at 3° C. and the mixture was stirred at room temperature for 30 min. The reaction mixture was partitioned, and the organic layer was washed with water (10 mL) and 5% aqueous NaCl solution (10 mL). The organic layer was dried over anhydrous magnesium sulfate, filtered by gravity, and the filtrate was concentrated under reduced pressure. The residue was purified by column chromatography (silica gel 25 g, n-hexane/ethyl acetate=10/1). To a solution of the residue in acetonitrile (15 mL) was added pyridine (0.86 g, 2.7 equivalents) at room temperature. Then, trifluoromethanesulfonic anhydride (2.84 g, 2.5 equivalents) was added at 5° C., and the mixture was stirred at room temperature for 2 hrs. Water (10 mL) was added at 3° C. and then ethyl acetate (30 mL) was added. The mixture was stirred at room temperature for 30 min. The reaction mixture was partitioned, and the organic layer was washed with water (10 mL) and 5% aqueous NaCl solution (10 mL). The organic layer was dried over anhydrous magnesium sulfate, filtered by gravity, and the filtrate was concentrated under reduced pressure. The residue was purified by column chromatography (silica gel 25 g, n-hexane/ethyl acetate=10/1). Effective fraction was concentrated under reduced pressure to give the title compound (0.74 g, colorless amorphous form). yield 34.0%

$^1$H-NMR (300 MHz, CDCl$_3$, TMS) δ: 7.36-7.43 (m, 4H), 7.47-7.52 (m, 4H), 7.65-7.73 (m, 8H), 8.20-8.22 (m, 4H).

$^{13}$C-NMR (75 MHz, CDCl$_3$, CDCl$_3$) δ: 119.75, 125.97, 127.30, 127.39, 127.71, 127.93, 128.97, 132.16, 132.24, 132.69, 139.92, 140.03, 145.30.

Elemental Analysis for C$_{34}$H$_{20}$F$_6$O$_6$S Calculated; C, 58.12; H, 2.87. Found; C, 57.86; H, 3.01.

Reference Example 22

7,7'-dimethoxy-1,1'-bi-2-naphthol

To a solution of 7-methoxy-2-naphthol (5.0 g, 28.7 mmoL) in dichloromethane (50 mL) was added a Cu(OH)Cl-tetramethylethylenediamine complex (1.33 g, 0.1 equivalent) at room temperature (25° C.), and the mixture was stirred at room temperature for 8 hrs. Water (20 mL) was added at 3° C., and the mixture was stirred at room temperature for 30 min. The reaction mixture was partitioned, and the organic layer was washed with 5% aqueous NaCl solution (10 mL). Then the organic layer was dried over anhydrous magnesium sulfate, filtered by gravity, and the filtrate was concentrated under reduced pressure. Ethyl acetate (50 mL) and silica gel (10 g) were added to the residue, and the mixture was stirred at room temperature for 1 hr. The filtrate was concentrated under reduced pressure to give the title compound (5.10 g, yellow-brown amorphous form). yield 100%.

$^1$H-NMR (300 MHz, CDCl$_3$, TMS) δ: 3.58 (s, 6H), 5.07 (s, 2H), 6.49 (d, 2H, J=2.43 Hz), 7.03 (dd, 2H, J=8.89 Hz, 2.49 Hz), 7.22 (d, 2H, J=8.84 Hz), 7.78 (d, 2H, J=8.90 Hz), 7.88 (d, 2H, J=8.85 Hz).

$^{13}$C-NMR (75 MHz, CDCl$_3$, CDCl$_3$) δ: 55.54, 103.58, 110.47, 115.50, 116.43, 125.20, 130.39, 131.51, 135.11, 153.74, 159.52.

Reference Example 23

7,7'-dimethoxy-2,2'-bis(trifluoromethanesulfonyloxy)-1,1'-binaphthyl

To a solution of 7,7'-dimethoxy-1,1'-bi-2-naphthol (5.10 g, 14.3 mmoL) in acetonitrile (50 mL) was added pyridine (3.05 g, 2.7 equivalents) at room temperature (25° C.). Then trifluoromethanesulfonic anhydride (10.12 g, 2.5 equivalents) was added at 5° C., and the mixture was stirred at room temperature for 5 hrs. Water (30 mL) was added at 3° C., and ethyl acetate (50 mL) was added. The mixture was stirred at room temperature for 30 min. The reaction mixture was partitioned, and the organic layer was washed with water (10 mL) and 5% aqueous NaCl solution (10 mL). Then the organic layer was dried over anhydrous magnesium sulfate, filtered by gravity, and the filtrate was concentrated under reduced pressure. Ethyl acetate (30 mL) and activated carbon (1.0 g) were added to the residue and the mixture was stirred at room temperature for 1 hr. The filtrate was concentrated under reduced pressure and the residue was recrystallized from diisopropyl ether to give the title compound (5.80 g, red-brown white crystals). yield 66.5%.

$^1$H-NMR (300 MHz, CDCl$_3$, TMS) δ: 3.55 (s, 6H), 6.56 (s, 2H), 7.26 (dd, 2H, J=8.99 Hz, 2.51 Hz), 7.48 (d, 2H, J=8.95 Hz), 7.92 (d, 2H, J=8.98 Hz), 8.06 (d, 2H, J=8.95 Hz).

$^{13}$C-NMR (75 MHz, CDCl$_3$, CDCl$_3$) δ: 55.61, 105.41, 117.11, 120.49, 122.63, 128.27, 130.26, 131.86, 134.98, 146.39, 159.57.

Elemental Analysis for C$_{24}$H$_{16}$F$_6$O$_8$S$_2$ Calculated; C, 47.22; H, 2.64. Found; C, 46.93; H, 2.55.

Example 1 bis(3,5-dimethylphenyl)phosphine-borane complex

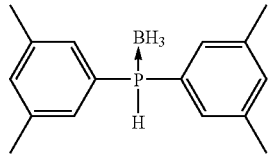

(Production Method 1)

Under an argon atmosphere, a solution of cerium chloride (14.3 g, 3.0 equivalents) in THF (40 mL) was stirred at room temperature (25° C.) for 30 min. Sodium borohydride (2.19 g, 3.0 equivalents) was added, and the mixture was stirred at room temperature for 1 hr. Bis(3,5-dimethylphenyl)phosphine oxide (5.0 g, 19.3 mmoL) synthesized in Reference Example 2 and lithium aluminum hydride (0.88 g, 1.2 equivalents) were successively added at 5° C. and the mixture was stirred at room temperature for 3 hrs. Water (40 mL) was added at 3° C., and then toluene (40 mL) and 6M-HCl (20 mL) were added. The mixture was stirred at room temperature for 30 min. The reaction mixture was partitioned, and the organic layer was dried over anhydrous magnesium sulfate, filtered by gravity. The filtrate was concentrated under reduced pressure and the residue was recrystallized from diisopropyl ether to give the title compound (2.8 g, white crystals). yield 57.4%.

(Production Method 2)

Under a nitrogen stream, a solution of cerium chloride (2.87 g, 2.99 equivalents) in THF (20 mL) was stirred at room temperature (25° C.) for 40 min. Sodium borohydride (0.44 g, 2.99 equivalents) was added, and the mixture was stirred at room temperature for 1 hr. Bis(3,5-dimethylphenyl)phosphine oxide (1.00 g, 3.89 mmol) synthesized in Reference Example 2 and lithium aluminum hydride (0.17 g, 1.16 equivalents) were successively added at −12° C. The mixture was stirred for 4 hrs. Water (10 mL) and then toluene (20 mL) were added at −10° C., and 6M-HCl (3 mL) was added at −5° C. The mixture was stirred at room temperature for 30 min. The reaction mixture was partitioned, and the organic layer was concentrated under reduced pressure. The concentrate was purified by silica gel column chromatography (10 g, toluene) and an effective fraction was concentrated under reduced pressure. The residue was recrystallized from heptane to give the title compound (0.70 g, white powder). yield 70.6%. melting point: 106.5° C.

$^1$H-NMR (300 MHz, CDCl$_3$, TMS) δ: 0.30-1.80 (m, 3H), 2.35 (s, 12H), 6.20 (dq, 1H, J$_{H\text{-}P}$=377.4 Hz, J=6.9 Hz), 7.14 (s, 2H), 7.26 (s, 2H), 7.30 (s, 2H).

$^{31}$P-NMR (121 MHz, CDCl$_3$, 85% H$_3$PO$_4$) δ: 0.88-1.32 (m), 3.32-5.02 (m).

Example 2

(S)-2,2'-bis[bis(3,5-dimethylphenyl)phosphino]-1,1'-binaphthyl

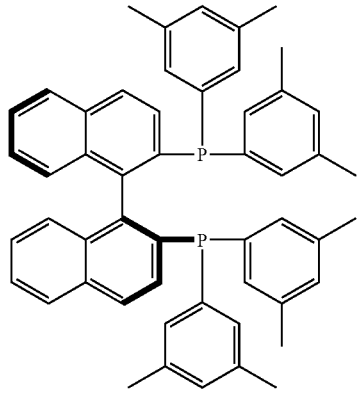

Under an argon atmosphere, to a solution (5 mL) of [1,2-bis(diphenylphosphino)-ethane]dichloronickel (42 mg, 0.1 equivalent), (S)-2,2'-bis(trifluoromethanesulfonyloxy)-1,1'-binaphthyl (399 mg, 0.73 mmoL) synthesized in Reference Example 1 and 1,4-diazabicyclo[2,2,2]octane (489 mg, 6.0 equivalents) in DMF was added at room temperature a bis(3,5-dimethylphenyl)phosphine-borane complex (428 mg, 2.3 equivalents) synthesized in Example 1. The mixture was stirred at room temperature for 30 min. and then at 110° C. for 96 hrs. DMF was evaporated under reduced pressure and methanol was added to the residue to give the title compound (329 mg, pale-yellow white crystals). yield 62%.

$^1$H-NMR (300 MHz, CDCl$_3$, TMS) δ: 2.06 (s, 12H), 2.13 (s, 12H), 6.70-6.73 (m, 10H), 6.81 (s, 2H), 6.90 (d, 2H, J=8.46 Hz), 7.01 (dd, 2H, J=7.14 Hz, 7.14 Hz), 7.39 (dd, 2H, J=6.99 Hz, 6.99 Hz), 7.52 (dd, 2H, J=8.49 Hz, 2.28 Hz), 7.84-7.88 (m, 4H).

$^{31}$P-NMR (121 MHz, CDCl$_3$, 85% H$_3$PO$_4$) δ: −14.25 (s).

(ref.: $^{31}$P-NMR (161 MHz, CDCl$_3$, 85% H$_3$PO$_4$) δ: −14.9. Journal of Organic Chemistry, vol. 59, p. 3064 (1994)

Elemental Analysis for C$_{52}$H$_{48}$P$_2$ Calculated; C, 84.99; H, 6.58; P, 8.43. Found; C, 84.60; H, 6.58; P, 8.07.

Example 3 bis(4-methoxyphenyl)phosphine-borane complex

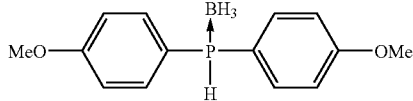

Under an argon atmosphere, a solution of cerium chloride (7.03 g, 3.0 equivalents) in THF (20 mL) was stirred at room temperature (25° C.) for 30 min. Sodium borohydride (1.08 g, 3.1 equivalents) was added, and the mixture was stirred at room temperature for 1 hr. Then bis(4-methoxyphenyl)phosphine oxide (2.5 g, 9.1 mmoL) synthesized in Reference Example 3 and lithium aluminum hydride (0.43 g, 1.2 equivalents) were successively added at 5° C. and the mixture was stirred at room temperature for 3 hrs. Water (20 mL) was added at 3° C., and then toluene (50 mL) and 6M-HCl (10 mL) were added. The mixture was stirred at room temperature for 30 min. The reaction mixture was partitioned, and the aqueous layer was extracted 3 times with toluene (20 mL). The combined organic layer was washed successively with 5% aqueous NaHCO$_3$ solution (20 mL) and 5% aqueous NaCl solution (20 mL). Then the organic layer was dried over anhydrous magnesium sulfate, filtered by gravity, and the filtrate was concentrated under reduced pressure. The residue was purified by column chromatography (silica gel 30 g, n-hexane/ethyl acetate=5/1→2/1). The residue was recrystallized from heptane to give the title compound (0.98 g, white crystals). yield 41.3%. melting point: 65.8° C.

$^1$H-NMR (300 MHz, CDCl$_3$, TMS) δ: 0.43-1.57 (m, 3H), 3.82 (s, 6H), 6.24 (dq, 1H, J=377.9 Hz, 6.78 Hz), 6.95 (dd, 4H, J=8.71 Hz, 1.72 Hz), 7.53-7.60 (m, 4H).

$^{31}$P-NMR (121 MHz, CDCl$_3$, 85% H$_3$PO$_4$) δ: −4.53--2.73 (m), −1.26-0.40 (m), −4.15 (m).

Example 4

(S)-2,2'-bis[bis(4-methoxyphenyl)phosphino]-1,1'-binaphthyl

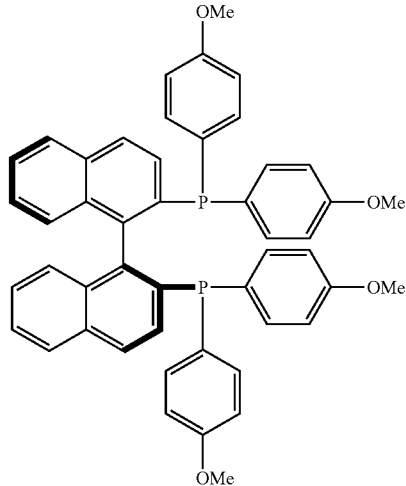

Under an argon atmosphere, to a solution (5 mL) of [1,2-bis(diphenylphosphino)-ethane]dichloronickel (53 mg, 0.1 equivalent), (S)-2,2'-bis(trifluoromethanesulfonyloxy)-1,1'-binaphthyl (500 mg, 0.91 mmoL) synthesized in Reference Example 1 and 1,4-diazabicyclo[2,2,2]octane (613 mg, 6.0 equivalents) in DMF was added at room temperature bis(4-methoxyphenyl)phosphine-borane complex (543 mg, 2.3 equivalents) synthesized in Example 3 and the mixture was stirred at room temperature for 30 min. and then at 110° C. for 48 hrs. DMF was evaporated under reduced pressure and methanol was added to the residue to give the title compound (444 mg, white crystals). yield 66%.

$^1$H-NMR (300 MHz, CDCl$_3$, TMS) δ: 3.73 (s, 12H), 6.64 (d, 4H, J=8.35 Hz), 6.69 (d, 4H, J=8.19 Hz), 6.80 (d, 2H, J=8.49 Hz), 6.92-7.03 (m, 10H), 7.30-7.38 (m, 2H), 7.40-7.45 (m, 2H), 7.82 (d, 2H, J=8.13 Hz), 7.87 (d, 2H, J=8.52 Hz).

$^{31}$P-NMR (121 MHz, CDCl$_3$, 85% H$_3$PO$_4$) δ: −17.40 (s).

(ref.: $^{31}$P-NMR (161 MHz, CDCl$_3$, 85% H$_3$PO$_4$) δ: −16.8. Journal of Organic Chemistry, vol. 59, p. 3064 (1994)

Example 5 bis(4-dimethylaminophenyl)phosphine-borane complex

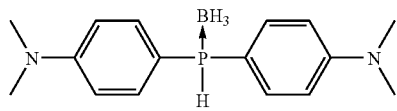

Under an argon atmosphere, a solution of cerium chloride (7.69 g, 3.0 equivalents) in THF (25 mL) was stirred at room temperature (25° C.) for 30 min. Sodium borohydride (1.22 g, 3.1 equivalents) was added, and the mixture was stirred at room temperature for 1 hr. Then bis(4-dimethylaminophenyl)phosphine oxide (3.0 g, 10.4 mmoL) synthesized in Reference Example 4 and lithium aluminum hydride (0.47 g, 1.2 equivalents) were successively added at 5° C., and the mixture was stirred at room temperature for 3 hrs. Water (20 mL) was added at 3° C. and then toluene (40 mL) and 6M-HCl (10 mL) were added. The mixture was stirred at room temperature for 30 min. The reaction mixture was neutralized with NaOH and partitioned. The aqueous layer was extracted with THF (50 mL). The combined organic layer was washed successively with 5% aqueous NaCl solution (20 mL). The organic layer was dried over anhydrous magnesium sulfate, filtered by gravity, and the filtrate was concentrated under reduced pressure. The residue was purified by column chromatography (silica gel 5 g, n-hexane/ethyl acetate=1/1). The residue was recrystallized from heptane to give the title compound (0.61 g, white crystals). yield 20.5%. melting point: 142.6° C.

$^1$H-NMR (300 MHz, CDCl$_3$, TMS) δ: 0.43-1.33 (m, 3H), 3.03 (s, 12H), 6.26 (dq, 1H, J=375.1 Hz, 6.57 Hz), 7.51 (d, 4H, J=8.81 Hz), 7.54 (d, 4H, J=8.81 Hz).

$^{31}$P-NMR (121 MHz, CDCl$_3$, 85% H$_3$PO$_4$) δ: −6.40--4.73 (m), −3.33--1.66 (m).

Example 6

(S)-2,2'-bis[bis(4-dimethylaminophenyl)phosphino]-1,1'-binaphthyl

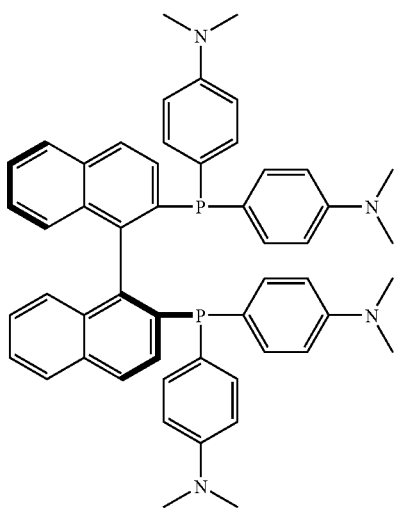

Under an argon atmosphere, to a solution (5 mL) of [1,2-bis(diphenylphosphino)-ethane]dichloronickel (48 mg, 0.1 equivalent), (S)-2,2'-bis(trifluoromethanesulfonyloxy)-1,1'-binaphthyl (507 mg, 0.92 mmoL) synthesized in Reference Example 1 and 1,4-diazabicyclo[2,2,2]octane (620 mg, 6.0 equivalents) in DMF was added at room temperature bis(4-dimethylaminophenyl)phosphine-borane complex (606 mg, 2.3 equivalents) synthesized in Example 5, and the mixture was stirred at room temperature for 30 min. and then at 110° C. for 129 hrs. DMF was evaporated under reduced pressure and methanol was added to the residue to give the title compound (461 mg, yellow-white crystals). yield 62.9%.

$^1$H-NMR (300 MHz, CDCl$_3$, TMS) δ: 2.88 (s, 24H), 6.43 (d, 4H, J=6.79 Hz), 6.50-6.59 (m, 4H), 6.77-7.03 (m, 12H), 7.18-7.26 (m, 2H), 7.51 (d, 2H, J=7.13 Hz), 7.78 (d, 2H, J=7.56 Hz), 7.83 (d, 2H, J=8.28 Hz).

$^{31}$P-NMR (121 MHz, CDCl$_3$, 85% H$_3$PO$_4$) δ: −18.00 (s).

Example 7 bis(4-fluorophenyl)phosphine-borane complex

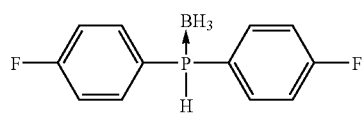

Under an argon atmosphere, a solution of cerium chloride (9.31 g, 3.0 equivalents) in THF (25 mL) was stirred at room temperature (25° C.) for 30 min. Sodium borohydride (1.48 g, 3.1 equivalents) was added, and the mixture was stirred at room temperature for 1 hr. Then bis(4-fluorophenyl)phosphine oxide (3.0 g, 12.6 mmoL) synthesized in Reference Example 5 and lithium aluminum hydride (0.57 g, 1.2 equivalents) were successively added at 5° C. and the mixture was stirred at room temperature for 3 hrs. Water (10 mL) was added at 3° C. and then toluene (30 mL) and 6M-HCl (20 mL) were added and the mixture was stirred at room temperature for 30 min. The reaction mixture was partitioned, and the aqueous layer was extracted with toluene (20 mL). The combined organic layer was washed with 5% aqueous NaCl solution (20 mL). The organic layer was dried over anhydrous magnesium sulfate, filtered by gravity, and the filtrate was concentrated under reduced pressure. The residue was purified by column chromatography (alumina 25 g, n-hexane/ethyl acetate=20/1). The residue was recrystallized from heptane to give the title compound (0.61 g, white crystals). yield 20.4%. melting point: 71.7° C.

$^1$H-NMR (300 MHz, CDCl$_3$, TMS) δ: 0.42-1.36 (m, 3H), 6.32 (dq, 1H, J=380.4 Hz, 6.89 Hz), 7.14-7.20 (m, 4H), 7.62-7.70 (m, 4H).

$^{31}$P-NMR (121 MHz, CDCl$_3$, 85% H$_3$PO$_4$) δ: −3.29−−1.21 (m), −0.29-1.91 (m).

Example 8

(S)-2,2'-bis[bis(4-fluorophenyl)phosphino]-1,1'-binaphthyl

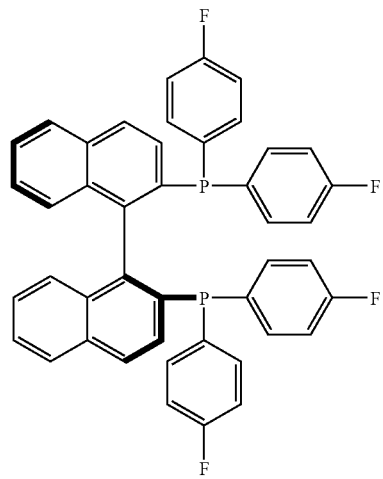

Under an argon atmosphere, to a solution (5 mL) of [1,2-bis(diphenylphosphino)ethane]dichloronickel (48 mg, 0.1 equivalent), (S)-2,2'-bis(trifluoromethanesulfonyloxy)-1,1'-binaphthyl (507 mg, 0.92 mmoL) synthesized in Reference Example 1 and 1,4-diazabicyclo[2,2,2]octane (620 mg, 6.0 equivalents) in DMF was added at room temperature bis(4-fluorophenyl)phosphine-borane complex (500 mg, 2.3 equivalents) synthesized in Example 7, and the mixture was stirred at room temperature for 30 min. then at 110° C. for 129 hrs. DMF was evaporated under reduced pressure and methanol was added to the residue to give the title compound (344 mg, yellow white crystals). yield 53.8%.

$^1$H-NMR (300 MHz, CDCl$_3$, TMS) δ: 6.74-7.07 (m, 16H), 7.34-7.41 (m, 4H), 7.41-7.93 (m, 4H), 7.85 (d, 2H, J=8.20 Hz), 7.91 (d, 2H, J=8.47 Hz).

$^{31}$P-NMR (121 MHz, CDCl$_3$, 85% H$_3$PO$_4$) δ: −16.63 (s).

(ref.: $^{31}$P-NMR (161 MHz, CDCl$_3$, 85% H$_3$PO$_4$) δ: −17.0. Journal of Organic Chemistry, vol. 59, p. 3064 (1994)

Example 9 bis(3,5-di-tert-butyl-4-methoxyphenyl)phosphine-borane complex

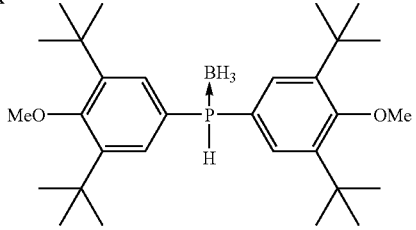

Under an argon atmosphere, a solution of cerium chloride (4.55 g, 3.0 equivalents) in THF (25 mL) was stirred at room temperature (25° C.) for 30 min. Sodium borohydride (0.72 g, 3.1 equivalents) was added, and the mixture was stirred at room temperature for 1 hr. Then bis(3,5-di-tert-butyl-4-methoxyphenyl)phosphine oxide (3.0 g, 6.16 mmoL) synthesized in Reference Example 7 and lithium aluminum hydride (0.28 g, 1.2 equivalents) were successively added at 5° C., and the mixture was stirred at room temperature for 18 hrs. Water (10 mL) was added at 3° C., and toluene (30 mL) and 6M-HCl (20 mL) were added. The mixture was stirred at room temperature for 30 min. The reaction mixture was partitioned and the aqueous layer was extracted with toluene (30 mL). The combined organic layer was washed successively with 5% aqueous NaCl solution (20 mL). The organic layer was dried over anhydrous magnesium sulfate, filtered by gravity, and the filtrate was concentrated under reduced pressure. The residue was purified by column chromatography (alumina 25 g, n-hexane). The residue was recrystallized from heptane to give the title compound (1.18 g, white crystals). yield 39.6%. melting point: 134.7° C.

$^1$H-NMR (300 MHz, CDCl$_3$, TMS) δ: 0.37-1.08 (m. 3H), 1.39 (s, 36H), 3.69 (s, 6H), 6.23 (dq, 1H, J=376.2 Hz, 6.78 Hz), 7.50 (d, 4H, J=12.18 Hz).
$^{31}$P-NMR (121 MHz, CDCl$_3$, 85% H$_3$PO$_4$) δ: −3.33--1.46 (m), −0.13-1.80 (m).

Example 10

(S)-2,2'-bis[bis(3,5-di-tert-butyl-4-methoxyphenyl)phosphino]-1,1'-binaphthyl

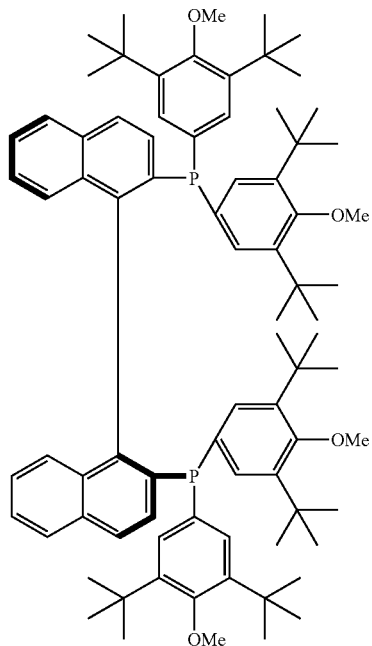

Under an argon atmosphere, to a solution (5 mL) of [1,2-bis(diphenylphosphino)-ethane]dichloronickel (48 mg, 0.1 equivalent), (S)-2,2'-bis(trifluoromethanesulfonyloxy)-1,1'-binaphthyl (507 mg, 0.91 mmoL) synthesized in Reference Example 1 and 1,4-diazabicyclo[2,2,2]octane (620 mg, 6.0 equivalents) in DMF was added a bis(3,5-di-tert-butyl-4-methoxyphenyl)phosphine-borane complex (1.03 g, 2.3 equivalents) synthesized in Example 9 at room temperature and the mixture was stirred at room temperature for 30 min. then at 110° C. for 153 hrs. DMF was evaporated under reduced pressure and methanol was added to the residue to give the title compound (737 mg, yellow white crystals). yield 69%. melting point: 129.5° C. angle of rotation: [α]$_D$=−232° (25° C., c=1.0, CHCl$_3$)

$^1$H-NMR (300 MHz, CDCl$_3$, TMS) δ: 1.21 (s, 36H), 1.24 (s, 36H), 3.58 (s, 6H), 3.64 (s, 6H), 6.64 (d, 2H, J=7.60 Hz), 6.77 (d, 2H, J=7.10 Hz), 6.92-7.00 (m, 4H), 7.13-7.20 (m, 4H), 7.30-7.37 (m, 2H), 7.42-7.51 (m, 2H), 7.77 (d, 2H, J=6.91 Hz), 7.86 (d, 2H, J=8.02 Hz).
$^{13}$C-NMR (75 MHz, CDCl$_3$, CDCl$_3$) δ: 33.34, 33.49, 36.96, 37.19, 65.44, 65.53, 126.64, 127.23, 128.76, 128.80, 128.92, 131.84, 132.95, 134.51, 144.02, 160.37, 161.31.
$^{31}$P-NMR (121 MHz, CDCl$_3$, 85% H$_3$PO$_4$) δ: −15.02 (s).
mass spectrometry (ESI-HR); Calculated; 1189.7332 Found; 1189.7350 (M−H)

Example 11

(S)-2,2'-bis[bis(4-methylphenyl)phosphino]-1,1'-binaphthyl

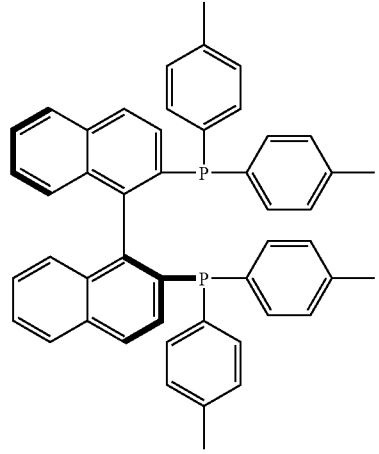

Under an argon atmosphere, to a solution (5 mL) of [1,2-bis(diphenylphosphino)-ethane]dichloronickel (48 mg, 0.1 equivalent) and (S)-2,2'-bis(trifluoromethanesulfonyloxy)-1,1'-binaphthyl (500 mg, 0.91 mmoL) synthesized in Reference Example 1 and 1,4-diazabicyclo[2,2,2]octane (610 mg, 6.0 equivalents) in DMF was added bis(4-methylphenyl)phosphine-borane complex (0.476 g, 2.3 equivalents) synthesized in Reference Example 18 at room temperature and the mixture was stirred at room temperature for 30 min. and then at 110° C. for 73 hrs. DMF was evaporated under reduced pressure and methanol was added to the residue to give the title compound (488 mg, white crystals). yield 79.2%.

$^1$H-NMR (300 MHz, CDCl$_3$, TMS) δ: 2.27 (s, 6H), 2.29 (s, 6H), 6.86-7.03 (m, 20H), 7.38-7.41 (m, 2H), 7.47-7.50 (m, 2H), 7.85 (d, 2H, J=8.16 Hz), 7.89 (d, 2H, J=8.48 Hz).
$^{31}$P-NMR (121 MHz, CDCl$_3$, 85% H$_3$PO$_4$) δ: −15.73 (s).
Elemental Analysis for C$_{48}$H$_{40}$P$_2$ Calculated; C, 84.93; H, 5.94; P, 9.13. Found; C, 84.52; H, 5.90; P, 9.09.

Example 12 bis(2-methylphenyl)phosphine-borane complex

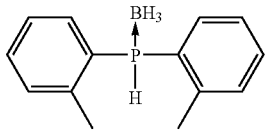

Under an argon atmosphere, a solution of cerium chloride (8.66 g, 3.0 equivalents) in THF (80 mL) was stirred at room temperature (25° C.) for 30 min. Sodium borohydride (1.37 g, 3.1 equivalents) was added, and the mixture was stirred at room temperature for 1 hr. Then bis(2-methylphenyl)phosphine oxide (2.7 g, 11.72 mmoL) synthesized in Reference Example 9 and lithium aluminum hydride (0.53 g, 1.2 equivalents) were successively added at 5° C., and the mixture was stirred at room temperature for 4 hrs. Toluene (80 mL) was added at 3° C., and then 3M-HCl (30 mL) was added. The mixture was stirred at room temperature for 30 min. The reaction mixture was partitioned, and the aqueous layer was extracted with toluene (20 mL). The combined organic layer was washed with 5% aqueous NaCl solution (20 mL). The organic layer was dried over anhydrous magnesium sulfate, filtered by gravity, and the filtrate was concentrated under reduced pressure. Toluene (20 mL) and silica gel (10 g) were added to the residue and the mixture was stirred at room temperature for 10 min. The mixture was filtered by gravity, and the filtrate was concentrated under reduced pressure. THF (5 mL) and $BH_3 \cdot THF$ (5 mL) were added to the residue at 5° C., and the mixture was stirred at room temperature for 1 hr. The mixture was concentrated under reduced pressure and the residue was recrystallized from heptane to give the title compound (1.15 g, white crystals). yield 43.0%. melting point: 78.0° C.

$^1$H-NMR (300 MHz, $CDCl_3$, TMS) δ: 0.42-1.63 (m, 3H), 2.32 (s, 6H), 6.47 (dq, 1H, J=377.5 Hz, 6.63 Hz), 7.21-7.31 (m, 4H), 7.38-7.43 (m, 2H), 7.59 (d, 1H, J=13.56 Hz), 7.61 (d, 1H, J=13.53 Hz).

$^{13}$C-NMR (75 MHz, $CDCl_3$, $CDCl_3$) δ: 20.81, 20.88, 126.36, 126.52, 130.85, 130.95, 131.67, 131.70, 133.82, 134.01, 141.42.

$^{31}$P-NMR (121 MHz, $CDCl_3$, 85% $H_3PO_4$) δ: −15.58-−14.22 (m), −12.67-−11.33 (m).

Example 13

(S)-2,2'-bis[bis(2-methylphenyl)phosphino]-1,1'-binaphthyl

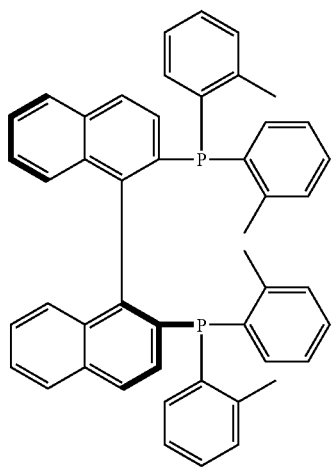

Under an argon atmosphere, to a solution (5 mL) of [1,2-bis(diphenylphosphino)-ethane]dichloronickel (96 mg, 0.1 equivalent), (S)-2,2'-bis(trifluoromethanesulfonyloxy)-1,1'-binaphthyl (1.0 g, 1.81 mmoL) synthesized in Reference Example 1 and 1,4-diazabicyclo[2,2,2]octane (1.22 g, 6.0 equivalents) in DMF was added at room temperature bis(2-methylphenyl)phosphine-borane complex (0.95 g, 2.3 equivalents) synthesized in Example 12 and the mixture was stirred at room temperature for 30 min. and then at 110° C. for 96 hrs. DMF was evaporated under reduced pressure and methanol was added to the residue to give the title compound (684 mg, white crystals). yield 55.5%.

$^1$H-NMR (300 MHz, $CDCl_3$, TMS) δ: 2.01 (s, 6H), 2.03 (s, 6H), 6.91-7.31 (m, 24H), 7.68-7.89 (m, 4H).

$^{31}$P-NMR (121 MHz, $CDCl_3$, 85% $H_3PO_4$) δ: −28.67 (s).

Example 14 bis(4-methoxy-3,5-dimethylphenyl)phosphine-borane complex

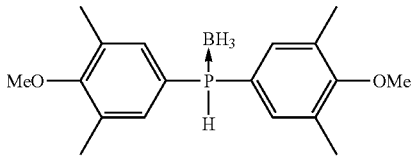

Under an argon atmosphere, a solution of cerium chloride (10.54 g, 3.0 equivalents) in THF (80 mL) was stirred at room temperature (25° C.) for 30 min. Sodium borohydride (1.67 g, 3.1 equivalents) was added, and the mixture was stirred at room temperature for 1 hr. Bis(4-methoxy-3,5-dimethylphenyl)phosphine oxide (4.54 g, 0.014 moL) synthesized in Reference Example 10 and lithium aluminum hydride (0.65 g, 1.2 equivalents) were successively added at 5° C. The mixture was stirred at room temperature for 4 hrs. Toluene (100 mL) was added at 3° C. and then 3M-HCl (40 mL) was added. The mixture was stirred at room temperature for 30 min. The reaction mixture was partitioned, and the aqueous layer was extracted with toluene (20 mL). The combined organic layer was washed with 5% aqueous NaCl solution (20 mL). The organic layer was dried over anhydrous magnesium sulfate, filtered by gravity, and the filtrate was concentrated under reduced pressure. Toluene (20 mL) and silica gel (10 g) were added to the residue and the mixture was stirred at room temperature for 10 min. The mixture was filtered by gravity, and the filtrate was concentrated under reduced pressure. The residue was recrystallized from heptane to give the title compound (3.14 g, white crystals). yield 69.6%. melting point: 81.6° C.

$^1$H-NMR (300 MHz, $CDCl_3$, TMS) δ: 0.37-1.56 (m, 3H), 2.27 (s, 12H), 3.72 (s, 6H), 6.13 (dq, 1H, J=377.5 Hz, 6.84 Hz), 7.27 (d, 4H, J=15.30 Hz).

$^{13}$C-NMR (75 MHz, $CDCl_3$, $CDCl_3$) δ: 16.07, 59.59, 120.59, 121.37, 131.97, 132.12, 133.32, 133.45, 159.87.

$^{31}$P-NMR (121 MHz, $CDCl_3$, 85% $H_3PO_4$) δ: −1.57-−0.32 (m), 1.38-2.83 (m).

Example 15

(S)-2,2'-bis[bis(4-methoxy-3,5-dimethylphenyl)phosphino]-1,1'-binaphthyl

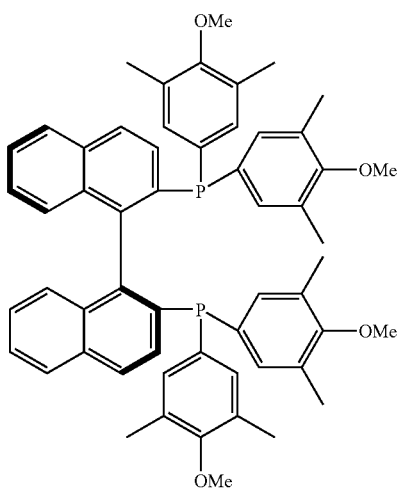

Under an argon atmosphere, to a solution (5 mL) of [1,2-bis(diphenylphosphino)-ethane]dichloronickel (96 mg, 0.1 equivalent), (S)-2,2'-bis(trifluoromethanesulfonyloxy)-1,1'-binaphthyl (1.0 g, 1.81 mmoL) synthesized in Reference Example 1 and 1,4-diazabicyclo[2,2,2]octane (1.22 g, 6.0 equivalents) in DMF was added at room temperature a bis(4-methoxy-3,5-dimethylphenyl)phosphine-borane complex (1.32 g, 2.3 equivalents) synthesized in Example 14, and the mixture was stirred at room temperature for 30 min. and then at 110° C. for 96 hrs. DMF was evaporated under reduced pressure and methanol was added to the residue to give the title compound (513 mg, white crystals). yield 33.1%.

$^1$H-NMR (300 MHz, CDCl$_3$, TMS) δ: 2.07 (s, 24H), 3.64 (s, 6H), 3.66 (s, 6H), 6.70-6.96 (m, 12H), 7.30-7.40 (m, 2H), 7.51-7.53 (m, 2H), 7.79-7.92 (m, 4H).

$^{31}$P-NMR (121 MHz, CDCl$_3$, 85% H$_3$PO$_4$) δ: −14.47 (s).

Example 16 bis(1,3-benzodioxol-5-yl)phosphine-borane complex

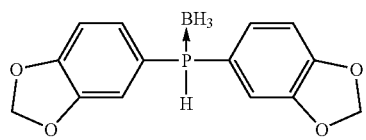

Under an argon atmosphere, a solution of cerium chloride (8.66 g, 3.0 equivalents) in THF (80 mL) was stirred at room temperature (25° C.) for 30 min. Sodium borohydride (1.37 g, 3.1 equivalents) was added, and the mixture was stirred at room temperature for 1 hr. Then bis(1,3-benzodioxol-5-yl) phosphine oxide (3.4 g, 0.012 moL) synthesized in Reference Example 11 and lithium aluminum hydride (0.53 g, 1.2 equivalents) were successively added at 5° C. and the mixture was stirred at room temperature for 4 hrs. Toluene (80 mL) was added at 3° C. and then 3M-HCl (30 mL) was added. The mixture was stirred at room temperature for 30 min. The reaction mixture was partitioned, and the aqueous layer was extracted with toluene (20 mL). The combined organic layer was washed with 5% aqueous NaCl solution (20 mL) and the organic layer was dried over anhydrous magnesium sulfate, filtered by gravity, and the filtrate was concentrated under reduced pressure. The residue was purified by column chromatography (silica gel 25 g, toluene). The residue was recrystallized from heptane to give the title compound (2.33 g, white crystals). yield 69.1%. melting point: 88.8° C.

$^1$H-NMR (300 MHz, CDCl$_3$, TMS) δ: 0.42-1.61 (m, 3H), 5.58 (q, 0.5H, J=6.78 Hz), 6.01 (s, 4H), 6.84-6.90 (m, 2.5H), 7.04 (dd, 2H, J=10.79 Hz, 1.44 Hz), 7.18 (dd, 1H, J=12.37 Hz, 1.45 Hz), 7.21 (dd, 1H, J=12.37 Hz, 1.46 Hz).

$^{13}$C-NMR (75 MHz, CDCl$_3$, CDCl$_3$) δ: 102.10, 109.53, 109.70, 112.43, 112.59, 118.95, 119.75, 128.37, 128.51, 148.70, 148.90, 151.15.

$^{31}$P-NMR (121 MHz, CDCl$_3$, 85% H$_3$PO$_4$) δ: 1.42-2.83 (m), 4.55-6.00 (m).

Elemental Analysis for C$_{14}$H$_{14}$BO$_4$P Calculated; C, 58.38; H, 4.90; P, 10.75. Found; C, 58.36; H, 4.92; P, 10.67.

Example 17

(S)-2,2'-bis[bis(1,3-benzodioxol-5-yl)phosphino]-1,1'-binaphthyl

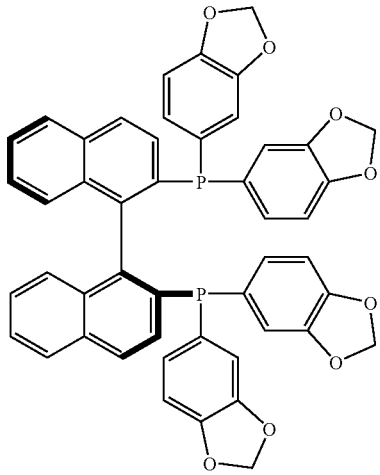

Under an argon atmosphere, to a solution (5 mL) of [1,2-bis(diphenylphosphino)-ethane]dichloronickel (86 mg, 0.1 equivalent), (S)-2,2'-bis(trifluoromethanesulfonyloxy)-1,1'-binaphthyl (0.9 g, 0.91 mmoL) synthesized in Reference Example 1 and 1,4-diazabicyclo[2,2,2]octane (1.1 g, 6.0 equivalents) in DMF was added at room temperature bis(1,3-benzodioxol-5-yl)phosphine-borane complex (1.08 g, 2.3 equivalents) synthesized in Example 16, and the mixture was stirred at room temperature for 30 min. and then at 110° C. for 96 hrs. DMF was evaporated under reduced pressure and methanol was added to the residue to give the title compound (310 mg, green white crystals). yield 23.8%.

$^{31}$P-NMR (121 MHz, CDCl$_3$, 85% H$_3$PO$_4$) δ: −12.46 (s).

(ref.: $^{31}$P-NMR (162 MHz, CDCl$_3$) δ: −12.1. JP-A-H9-124669)

Example 18 bis(2-naphthyl)phosphine-borane complex

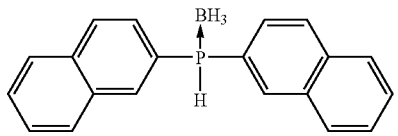

Under an argon atmosphere, a solution of cerium chloride (8.66 g, 3.0 equivalents) in THF (80 mL) was stirred at room temperature (25° C.) for 30 min. Sodium borohydride (1.37 g, 3.1 equivalents) was added, and the mixture was stirred at room temperature for 1 hr. Then bis(2-naphthyl)phosphine oxide (3.54 g, 0.012 moL) synthesized in Reference Example 12 and lithium aluminum hydride (0.53 g, 1.2 equivalents) were successively added at 5° C. and the mixture was stirred at room temperature for 3 hrs. Toluene (80 mL) was added at 0° C. and then 3M-HCl (30 mL) was added. The mixture was stirred at room temperature for 30 min. The reaction mixture was partitioned, and the aqueous layer was extracted with toluene (40 mL). The combined organic layer was washed with 5% aqueous NaCl solution (20 mL). The organic layer was dried over anhydrous magnesium sulfate, filtered by gravity, and the filtrate was concentrated under reduced pressure. Toluene (30 mL) and silica gel (10 g) were added to the residue and the mixture was stirred at room temperature for 10 min. The mixture was filtered by gravity, and the filtrate was concentrated under reduced pressure. The residue was recrystallized from heptane to give the title compound (2.23 g, white crystals). yield 63.3%. melting point: 113.2° C.

$^1$H-NMR (300 MHz, CDCl$_3$, TMS) δ: 0.68-1.85 (m, 3H), 6.58 (dq, 1H, J=378.6 Hz, 6.88 Hz), 7.56-7.61 (m, 6H), 7.88-7.91 (m, 6H), 8.32 (d, 2H, J=13.56 Hz).

$^{13}$C-NMR (75 MHz, CDCl$_3$, CDCl$_3$) δ: 123.41, 127.53, 128.23, 128.31, 128.61, 128.97, 129.30, 129.43, 133.22, 135.00, 135.15.

$^{31}$P-NMR (121 MHz, CDCl$_3$, 85% H$_3$PO$_4$) δ: 1.11-2.42 (m), 4.30-5.48 (m).

Elemental Analysis for C$_{20}$H$_{18}$BP Calculated; C, 80.03; H, 6.04; P, 10.32. Found; C, 80.40; H, 5.92; P, 9.95.

Example 19

(S)-2,2'-bis[bis(2-naphthyl)phosphino]-1,1'-binaphthyl

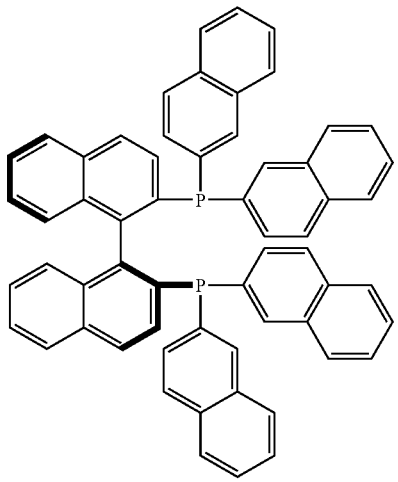

Under an argon atmosphere, to a solution (5 mL) of [1,2-bis(diphenylphosphino)ethane]dichloronickel (96 mg, 0.1 equivalent), (S)-2,2'-bis(trifluoromethanesulfonyloxy)-1,1'-binaphthyl (1.0 g, 1.81 mmoL) synthesized in Reference Example 1 and 1,4-diazabicyclo[2,2,2]octane (1.22 g, 6.0 equivalents) in DMF was added at room temperature a bis(2-naphthyl)phosphine-borane complex (1.25 g, 2.3 equivalents) synthesized in Example 18, and the mixture was stirred at room temperature for 30 min. and then at 110° C. for 101 hrs. DMF was evaporated under reduced pressure and methanol was added to the residue to give the title compound (875 mg, white crystals). yield 58.7%.

$^{31}$P-NMR (121 MHz, CDCl$_3$, 85% H$_3$PO$_4$) δ: −12.99 (s).

(ref.: $^{31}$P-NMR (162 MHz, CDCl$_3$) δ: −13.57. JP-A-H9-124669)

Example 20 bis(4-chlorophenyl)phosphine-borane complex

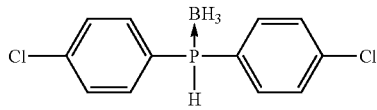

Under an argon atmosphere, a solution of cerium chloride (8.66 g, 3.0 equivalents) in THF (80 mL) was stirred at room temperature (25° C.) for 30 min. Sodium borohydride (1.37 g, 3.1 equivalents) was added, and the mixture was stirred at room temperature for 1 hr. Then bis(4-chlorophenyl)phosphine oxide (3.18 g, 0.012 moL) synthesized in Reference Example 13 and lithium aluminum hydride (0.53 g, 1.2 equivalents) were successively added at 5° C., and the mixture was stirred at room temperature for 4 hrs. Toluene (80 mL) was added at 0° C., and 3M-HCl (30 mL) was added. The mixture was stirred at room temperature for 30 min. The reaction mixture was partitioned, and the aqueous layer was extracted with toluene (20 mL). The combined organic layer was washed with 5% aqueous NaCl solution (20 mL) and the organic layer was dried over anhydrous magnesium sulfate, filtered by gravity, and the filtrate was concentrated under reduced pressure. Toluene (20 mL) and silica gel (10 g) were added to the residue and the mixture was stirred at room temperature for 10 min. The mixture was filtered by gravity, and the filtrate was concentrated under reduced pressure. THF (5 mL) and BH$_3$.THF (5 mL) were added to the residue at 5° C., and the mixture was stirred at room temperature for 1 hr. The mixture was concentrated under reduced pressure and the residue was recrystallized from heptane to give the title compound (1.58 g, white crystals). yield 50.3%.

$^1$H-NMR (300 MHz, CDCl$_3$, TMS) δ: 0.41-1.60 (m, 3H), 6.28 (dq, 1H, J=381.6 Hz, 6.96 Hz), 7.36-7.44 (m, 4H), 7.54-7.65 (m, 4H).

$^{13}$C-NMR (75 MHz, CDCl$_3$, CDCl$_3$) δ: 123.83, 124.60, 128.92, 129.46, 129.61, 132.17, 134.10, 134.24, 138.62.

$^{31}$P-NMR (121 MHz, CDCl$_3$, 85% H$_3$PO$_4$) δ: −1.06-0.33 (m), 2.08-3.47 (m).

Example 21

(S)-2,2'-bis[bis(4-chlorophenyl)phosphino]-1,1'-binaphthyl

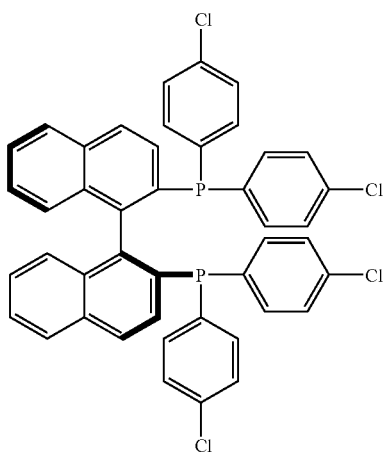

Under an argon atmosphere, to a solution (5 mL) of [1,2-bis(diphenylphosphino)-ethane]dichloronickel (96 mg, 0.1 equivalent), (S)-2,2'-bis(trifluoromethanesulfonyloxy)-1,1'-binaphthyl (1.0 g, 1.81 mmoL) synthesized in Reference Example 1 and 1,4-diazabicyclo[2,2,2]octane (1.22 g, 6.0 equivalents) in DMF was added at room temperature a bis(4-chlorophenyl)phosphine-borane complex (1.29 g, 2.6 equivalents) synthesized in Example 20. The mixture was stirred at room temperature for 30 min. and then at 110° C. for 96 hrs. The reaction mixture was subjected to $^{31}$P-NMR measurement to confirm the title compound.

$^{31}$P-NMR (121 MHz, CDCl$_3$, 85% H$_3$PO$_4$) δ: −15.80 (s).
(ref.: $^{31}$P-NMR (161 MHz, CDCl$_3$, 85% H$_3$PO$_4$) δ: −16.8. Journal of Organic Chemistry, vol. 59, p. 3064 (1994))

Example 22 bis(p-tert-butylphenyl)phosphine-borane complex

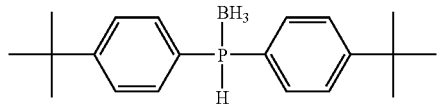

Under a nitrogen stream, a solution of cerium chloride (19.84 g, 2.98 equivalents) in THF (160 mL) was stirred at room temperature (25° C.) for 30 min. Sodium borohydride (3.11 g, 3.04 equivalents) was added, and the mixture was stirred at room temperature for 1.5 hrs. Then bis(p-tert-butylphenyl)phosphine oxide (8.49 g, 27.0 mmol) synthesized in Reference Example 15 and lithium aluminum hydride (1.55 g, 1.21 equivalents) were successively added at −17° C. and the mixture was stirred at room temperature for 2 hrs. Toluene (80 mL) was added at −10° C. and then 6M-HCl (25 mL) was added and water (25 mL) was added at 4° C. The mixture was stirred at room temperature for 30 min. The reaction mixture was partitioned, and the organic layer was washed successively with water (30 mL), 10% aqueous NaHCO$_3$ solution (30 mL) and 10% aqueous NaCl solution (30 mL). The organic layer was dried over anhydrous magnesium sulfate, filtered by gravity, and further passed through a membrane filter (0.2 μm) under reduced pressure. The filtrate was concentrated under reduced pressure. The residue was dissolved in THF (100 mL) and a borane-THF complex (10 mL, 0.38 equivalent) was added at room temperature. The mixture was stirred for 16 hrs. and concentrated under reduced pressure. Toluene (30 mL) was added to the residue for dissolution, and the mixture was purified by silica gel column chromatography (silica gel 100 g, toluene), an effective fraction was concentrated under reduced pressure. The residue was recrystallized from n-hexane and dried (reduced pressure, 40° C.) to give the title compound (6.33 g, white powder). yield 75.0%. melting point: 151.5° C.

$^1$H-NMR (300 MHz, CDCl$_3$, TMS) δ: 0.43-1.52 (m, 3H), 1.33 (s, 18H), 6.28 (dq, 1H, J$_{H-P}$=384 Hz, J=6.9 Hz), 7.46 (s, 1H), 7.47 (s, 1H), 7.49 (s, 1H), 7.50 (s, 1H), 7.59 (s, 1H), 7.62 (s, 1H), 7.63 (s, 1H), 7.65 (s, 1H).

$^{13}$C-NMR (75 MHz, CDCl$_3$, CDCl$_3$) δ: 31.04, 34.91, 122.46, 123.24, 125.99, 126.13, 132.68, 132.81, 154.99, 155.02.

$^{31}$P-NMR (121 MHz, CDCl$_3$, 85% H$_3$PO$_4$) δ: −2.42-−1.52 (m), 0.82-1.52 (m).

Example 23

(S)-2,2'-bis[bis(p-tert-butylphenyl)phosphino]-1,1'-binaphthyl

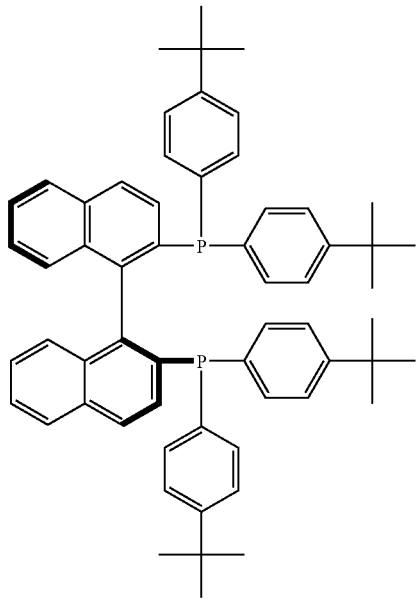

Under an argon atmosphere, to a solution (5 mL) of [1,2-bis(diphenylphosphino)ethane]dichloronickel (0.08 g, 0.10 equivalent), (S)-2,2'-bis(trifluoromethanesulfonyloxy)-1,1'-binaphthyl (0.78 g, 1.41 mmol) synthesized in Reference Example 1 and 1,4-diazabicyclo[2,2,2]octane (0.94 g, 5.97 equivalents) in DMF was added at room temperature a bis(p- tert-butylphenyl)phosphine-borane complex (1.02 g, 2.31 equivalents) synthesized in Example 22, and the mixture was stirred at room temperature for 30 min. and then at 110° C. for 96 hrs. DMF solution was evaporated under reduced pressure and methanol was added to the residue to give the title compound (0.79 g, pale-yellow powder). yield 66%

$^1$H-NMR (300 MHz, CDCl$_3$, TMS) δ: 1.25 (s, 18H), 1.27 (s, 18H), 6.68-6.73 (m, 4H), 6.94-6.96 (m, 4H), 7.07 (d, 4H, J=8.0 Hz), 7.11-7.13 (m, 4H), 7.23-7.27 (m, 6H), 7.47 (d, 2H, J=8.4 Hz), 7.81 (d, 2H, J=8.1 Hz), 7.86 (d, 2H, J=8.5 Hz).

$^{13}$C-NMR (75 MHz, DMSO, DMSO) δ: 30.91, 30.94, 34.13, 34.15, 124.49, 124.54, 124.59, 124.72, 125.00, 125.66, 127.00, 127.09, 130.10, 132.33, 132.46, 132.59, 132.71, 132.97, 133.72, 133.86, 134.01, 136.21, 144.10, 150.03, 150.80.

$^{31}$P-NMR (121 MHz, CDCl$_3$, 85% H$_3$PO$_4$) δ: −16.04 (s).

mass spectrometry (ESI-HR); Calculated; 847.4562 Found; 847.4496 (MH$^+$)

Example 24 bis(3,5-di-tert-butylphenyl)phosphine-borane complex

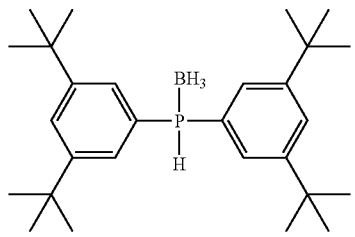

Under a nitrogen stream, a solution of cerium chloride (4.88 g, 3.00 equivalents) in THF (40 mL) was stirred at room temperature (25° C.) for 30 min. Sodium borohydride (0.75 g, 3.00 equivalents) was added, and the mixture was stirred at room temperature for 1 hr. Then bis(3,5-di-tert-butylphenyl) phosphine oxide (2.81 g, 6.6 mmol) synthesized in Reference Example 16 and lithium aluminum hydride (0.39 g, 1.23 equivalents) were successively added at −9° C. and the mixture was stirred for 1.5 hrs. Toluene (20 mL) was added at 4° C., 6M-HCl (6 mL) was added and water (10 mL) was added at 4° C., and the mixture was stirred at room temperature for 30 min. The reaction mixture was partitioned, and the organic layer was dried over anhydrous magnesium sulfate, filtered by gravity, and passed through a membrane filter (0.2 μm) under reduced pressure. To the filtrate was added a borane-THF complex (7 mL, 1.08 equivalents) at room temperature and the mixture was stirred for 16 hrs. and concentrated under reduced pressure. To the concentrate was added a borane-THF complex (10 mL, 1.55 equivalents) at room temperature and the mixture was concentrated under reduced pressure. Toluene (10 mL) was added to the residue for dissolution and the mixture was purified by silica gel column chromatography (silica gel 25 g, toluene). The effective fraction was concentrated under reduced pressure. The residue was recrystallized from n-hexane and dried (reduced pressure, 40° C.) to give the title compound (2.03 g, white powder). yield 72.7%. melting point: 135.4° C.

$^1$H-NMR (300 MHz, CDCl$_3$, TMS) δ: 0.55-1.80 (m, 3H), 1.34 (s, 36H), 6.33 (dq, 1H, J$_{H-P}$=375.5 Hz, J=6.8 Hz), 7.51 (s, 1H), 7.51 (s, 1H), 7.55 (s, 1H), 7.55 (s, 1H), 7.58 (s, 1H), 7.59 (s, 1H).

$^{13}$C-NMR (75 MHz, CDCl$_3$, CDCl$_3$) δ: 31.26, 34.91, 122.46, 123.24, 125.99, 126.13, 132.68, 132.81, 154.99, 155.02.

$^{31}$P-NMR (121 MHz, CDCl$_3$, 85% H$_3$PO$_4$) δ: 0.95-1.22 (m), 3.88-4.75 (m).

Example 25

(S)-2,2'-bis[bis(3,5-di-tert-butylphenyl)phosphino]-1,1'-binaphthyl

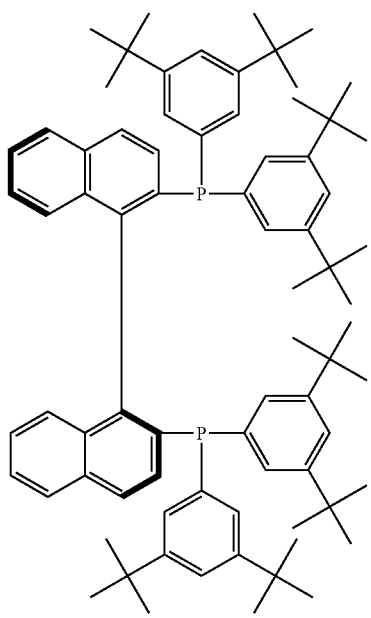

Under an argon atmosphere, to a solution (5 mL) of [1,2-bis(diphenylphosphino)ethane]dichloronickel (0.07 g, 0.10 equivalent), (S)-2,2'-bis(trifluoromethanesulfonyloxy)-1,1'-binaphthyl (0.77 g, 1.41 mmol) synthesized in Reference Example 1 and 1,4-diazabicyclo[2,2,2]octane (0.94 g, 5.96 equivalents) in DMF was added a bis(3,5-di-tert-butylphenyl) phosphine-borane complex (1.00 g, 1.68 equivalents) synthesized in Example 24 at room temperature and the mixture was stirred at room temperature for 30 min. and then at 110° C. for 96 hrs. DMF solution was evaporated under reduced pressure, and methanol was added to the residue to give the title compound (0.38 g, white powder). yield 30%. melting point: 217.8° C.

$^1$H-NMR (300 MHz, CDCl$_3$, TMS) δ: 1.11 (s, 36H), 1.14 (s, 36H), 6.71 (d, 2H, J=8.3 Hz), 6.77-6.80 (m, 2H), 6.95-6.98 (m, 4H), 7.14-7.23 (m, 8H), 7.25-7.28 (m, 2H), 7.54 (d, 2H, J=8.5 Hz), 7.77 (d, 2H, J=8.1 Hz), 7.85 (d, 2H, 8.5 Hz).

$^{13}$C-NMR (75 MHz, DMSO, DMSO) δ: 31.03, 34.32, 34.44, 120.71, 121.90, 125.03, 125.55, 126.95, 127.06, 127.18, 127.23, 128.08, 128.23, 128.38, 130.41, 132.79, 136.79, 137.65, 145.03, 145.82, 149.22, 149.30, 149.35, 149.40

$^{31}$P-NMR (121 MHz, CDCl$_3$, 85% H$_3$PO$_4$) δ: −12.16 (s).

mass spectrometry (ESI-HR); Calculated; 1071.7066 Found; 1071.7039 (MH$^+$)

Example 26 bis(m-tolyl)phosphine-borane complex

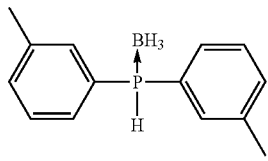

Under a nitrogen stream, a solution of cerium chloride (26.40 g, 3.00 equivalents) in THF (220 mL) was stirred at room temperature (25° C.) for 30 min. Sodium borohydride (4.06 g, 3.00 equivalents) was added, and the mixture was stirred at room temperature for 1.5 hrs. Then bis(m-tolyl)phosphine oxide (8.22 g, 35.7 mmol) synthesized in Reference Example 17 and lithium aluminum hydride (2.06 g, 1.22 equivalents) were successively added at −9° C. and the mixture was stirred for 3 hrs. 6M-HCl (33 mL) was added at −3° C., then water (33 mL) was added and toluene (130 mL) was added at 4° C. The mixture was stirred at room temperature for 30 min. The reaction mixture was partitioned, and the organic layer was washed successively with water (50 mL), 10% aqueous $NaHCO_3$ solution (50 mL) and 10% aqueous NaCl solution (50 mL). The organic layer was dried over anhydrous magnesium sulfate, filtered by gravity, and further passed through a membrane filter (0.2 μm) under reduced pressure. A borane-THF complex (36 mL, 1.02 equivalents) was added to the filtrate at around 0° C. and the mixture was stirred at room temperature for 13.5 hrs. A borane-THF complex (6.2 mL, 0.18 equivalent) was further added at room temperature, and the mixture was concentrated under reduced pressure. The residue was recrystallized from n-hexane and dried (reduced pressure, 40° C.) to give the title compound (1.70 g, white powder). yield 21%

$^1$H-NMR (300 MHz, DMSO, TMS) δ: 0.58-1.75 (m, 3H), 2.34 (s, 6H), 5.88-5.98 (m, 0.5H), 7.20-7.31 (m, 0.5H), 7.37-7.53 (m, 8H).

$^{13}$C-NMR (75 MHz, DMSO, DMSO) δ: 21.24, 126.48, 129.45, 129.60, 130.03, 130.15, 132.76, 133.07, 133.20, 139.00, 139.18.

$^{31}$P-NMR (121 MHz, $CDCl_3$, 85% $H_3PO_4$) δ: −4.22-−3.00 (m), −0.89-0.23 (m).

Example 27

(S)-2,2'-bis[bis(m-tolyl)phosphino]-1,1'-binaphthyl

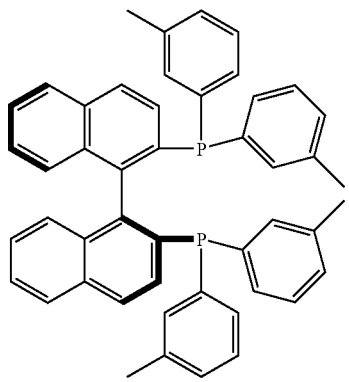

Under an argon atmosphere, to a solution (5 mL) of [1,2-bis(diphenylphosphino)ethane]dichloronickel (0.10 g, 0.10 equivalent), (S)-2,2'-bis(trifluoromethanesulfonyloxy)-1,1'-binaphthyl (1.05 g, 1.91 mmol) synthesized in Reference Example 1 and 1,4-diazabicyclo[2,2,2]octane (1.28 g, 5.99 equivalents) in DMF was added at room temperature a bis(m-tolyl)phosphine-borane complex (1.00 g, 2.31 equivalents) synthesized in Example 26, and the mixture was stirred at room temperature for 30 min. and then at 110° C. for 96 hrs. The reaction mixture was subjected to $^{31}$P-NMR measurement to confirm the title compound.

$^{31}$P-NMR (121 MHz, $CDCl_3$, 85% $H_3PO_4$) δ: −14.5 (s).

(ref.: $^{31}$P-NMR (161 MHz, $CDCl_3$, 85% $H_3PO_4$) δ: −14.4. *Journal of Organic Chemistry*, vol. 59, p. 3064 (1994)

Example 28

(S)-2,2'-bis(diphenylphosphino)-6,6'-diphenyl-1,1'-binaphthyl

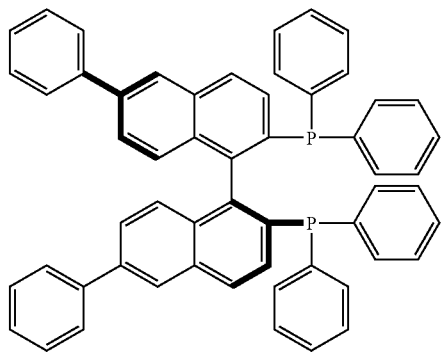

Under an argon atmosphere, to a solution (5 mL) of [1,2-bis(diphenylphosphino)ethane]dichloronickel (52 mg, 0.1 equivalent), (S)-6,6'-diphenyl-2,2'-bis(trifluoromethanesulfonyloxy)-1,1'-binaphthyl (700 mg, 0.99 mmoL) synthesized in Reference Example 21 and 1,4-diazabicyclo[2,2,2]octane (670 mg, 6.0 equivalents) in DMF was added a diphenylphosphine-borane complex (0.458 g, 2.3 equivalents) at room temperature, and the mixture was stirred at room temperature for 30 min. and then at 110° C. for 90 hrs. DMF was evaporated under reduced pressure and methanol was added to the residue to give the title compound (412 mg, slightly brown white crystals). yield 53.4%.

$^1$H-NMR (300 MHz, $CDCl_3$, TMS) δ: 6.93 (d, 2H, J=8.76 Hz), 7.12-7.22 (m, 20H), 7.29 (s, 2H), 7.35-7.51 (m, 8H), 7.64-7.67 (m, 4H), 7.99 (d, 2H, J=8.76 Hz), 8.07 (d, 2H, J=1.64 Hz).

$^{13}$C-NMR (75 MHz, $CDCl_3$, $CDCl_3$) δ: 125.99, 127.74, 128.51, 128.83, 129.21, 134.66, 141.35.

$^{31}$P-NMR (121 MHz, $CDCl_3$, 85% $H_3PO_4$) δ: −13.82 (s).

Example 29

2,2'-bis(diphenylphosphino)-7,7'-dimethoxy-1,1'-binaphthyl

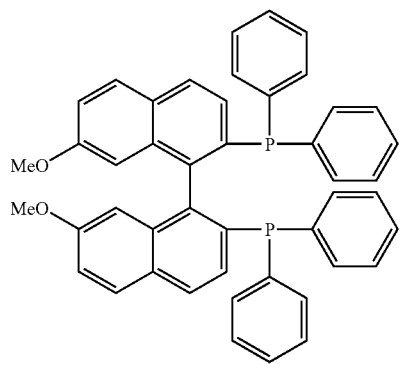

Under an argon atmosphere, to a solution (5 mL) of [1,2-bis(diphenylphosphino)-ethane]dichloronickel (53 mg, 0.1 equivalent), 7,7'-dimethoxy-2,2'-bis(trifluoromethanesulfonyloxy)-1,1'-binaphthyl (610 mg, 0.99 mmoL) synthesized in Reference Example 23 and 1,4-diazabicyclo[2,2,2]octane (670 mg, 6.0 equivalents) in DMF was added a diphenylphosphine-borane complex (0.458 g, 2.3 equivalents) at room temperature, and the mixture was stirred at room temperature for 30 min. and then at 110° C. for 77 hrs. DMF was evaporated under reduced pressure and methanol was added to the residue to give the title compound (120 mg, yellow white crystals). yield 17.7%.

$^1$H-NMR (300 MHz, CDCl$_3$, TMS) δ: 3.16 (s, 6H), 6.05 (d, 2H, J=2.26 Hz), 7.01 (dd, 2H, J=9.00 Hz, 2.49 Hz), 7.12-7.19 (m, 20H), 7.38 (d, 2H, J=8.44 Hz), 7.74 (d, 2H, J=8.88 Hz), 7.83 (d, 2H, J=8.38 Hz).

$^{13}$C-NMR (75 MHz, CDCl$_3$, CDCl$_3$) δ: 54.98, 106.07, 119.52, 127.77, 128.18, 128.41, 128.97, 129.63, 132.90, 134.78, 135.08, 146.39, 159.56.

$^{31}$P-NMR (121 MHz, CDCl$_3$, 85% H$_3$PO$_4$) δ: −13.82 (s).

Example 30

(S)-2,2'-bis(diphenylphosphino)-1,1'-binaphthyl

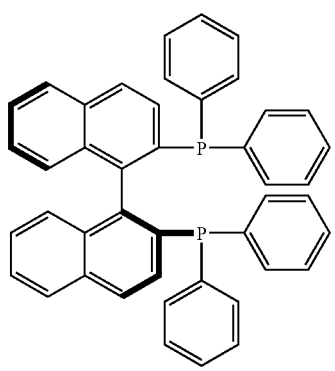

Under an argon atmosphere, to a solution (5 mL) of [1,2-bis(diphenylphosphino)-ethane]dichloronickel (53 mg, 0.1 equivalent), (S)-2,2'-bis(trifluoromethanesulfonyloxy)-1,1'-binaphthyl (500 mg, 0.91 mmoL) synthesized in Reference Example 1 and 1,4-diazabicyclo[2,2,2]octane (613 mg, 6.0 equivalents) in DMF was added a diphenylphosphine-borane complex (418 mg, 2.3 equivalents) at room temperature, and the mixture was stirred at room temperature for 30 min. and then at 110° C. for 96 hrs. DMF was evaporated under reduced pressure and methanol was added to the residue to give the title compound (401 mg, pale-yellow white crystals). yield 71%.

$^1$H-NMR (300 MHz, CDCl$_3$, TMS) δ: 6.83 (d, 2H, J=8.26 Hz), 6.89-6.94 (m, 2H), 7.07-7.20 (m, 20H), 7.32-7.37 (m, 2H), 7.43-7.47 (m, 2H), 7.85 (d, 2H, J=8.14 Hz), 7.89 (d, 2H, J=8.49 Hz).

$^{31}$P-NMR (121 MHz, CDCl$_3$, 85% H$_3$PO$_4$) δ: −14.90 (s).

mass spectrometry (ESI-HR); Calculated; 623.2058 Found; 623.2030 (MH$^+$)

Example 31

(S)-2,2'-bis[bis(3,5-dimethylphenyl)phosphino]-1,1'-binaphthyl

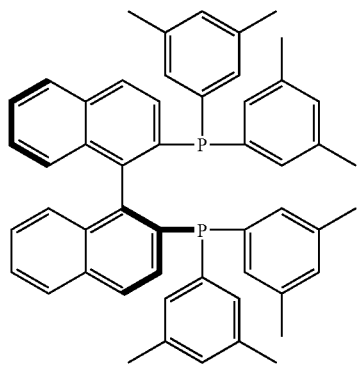

In the same manner as in Example 2 and changing the amine to be used to 1) tetramethylethylenediamine, 2) triethylamine, 3) diisopropylethylamine, 4) diethylamine or 5) pyridine, (S)-2,2'-bis[bis(3,5-dimethylphenyl)phosphino]-1,1'-binaphthyl was produced. The results are shown in Table 1.

TABLE 1

| | Amine | yield |
|---|---|---|
| 1 | tetramethylethylenediamine | 48% |
| 2 | triethylamine | 42% |
| 3 | diisopropylethylamine | 42% |
| 4 | diethylamine | 40% |
| 5 | pyridine | 27% |

Example 32

(S)-2,2'-bis[bis(3,5-dimethylphenyl)phosphino]-1,1'-binaphthyl

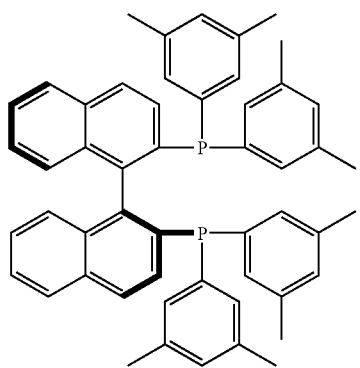

In the same manner as in Example 2 and changing the nickel catalyst to 1) $NiCl_2$, 2) $NiCl_2 \cdot bis(diphenyl)phosphinyl$ ferrocene or 3) $NiCl_2$, bis(diphenyl)phosphinoethane, (S)-2,2'-bis[bis(3,5-dimethylphenyl)phosphino]-1,1'-binaphthyl was produced. The results are shown in Table 2. For calculation of HPLC area (%), HPLC conditions (column: ZORBAX Rx-C8, 4.6×250 mm, solution: $MeCN/H_2O=90/10$, flow rate: 1.0 mL/min, detection wavelength: 254 nm) were used. In 3), $NiCl_2$ and bis(diphenyl)phosphinoethane were separately added.

TABLE 2

| | HPLC area (%) | |
|---|---|---|
| nickel catalyst | (S)-2,2'-bis[bis(3,5-dimethylphenyl)-phosphino]-1,1'-binaphthyl (product) | (S)-2,2'-bis(trifluoromethane-sulfonyloxy)-1,1'-binaphthyl (starting material) |
| 1  $NiCl_2$ | 24.8% | 13.1% |
| 2  $NiCl_2 \cdot$ bis(diphenyl)-phosphinyl ferrocene | 43.9% | 7.5% |
| 3  $NiCl_2$, bis(diphenyl)-phosphino-ethane | 29.2% | 13.1% |

Example 33

Asymmetric Hydrogenation of Methyl (Z)-α-acetamide Cinnamate

To a solution of $Rh(cod)_2OTf$ (4.27 mg, 0.0091 mmoL) in methanol (1 mL) was added (S)-2,2'-bis[bis(3,5-di-tert-butyl-4-methoxyphenyl)phosphino]-1,1'-binaphthyl (12.65 mg, 0.011 mmoL) synthesized in Example 10, and the mixture was stirred at room temperature (25° C.) for 30 min. To a solution of methyl (Z)-α-acetamide cinnamate (0.10 g, 0.456 mmoL) in methanol (4 mL) was added an Rh complex solution prepared in the above for hydrogenation at hydrogen pressure of 1.0 MPa and 25° C. for 24 hrs. The reaction mixture was measured by GC (column: CHIRASIL VAL, 0.25 mm×30 m) to give conversion rate >99.9%, optical purity 91.43% ee (R).

Comparative Example 1

Asymmetric Hydrogenation of Methyl (Z)-α-acetamide Cinnamate

To a solution of $Rh(cod)_2OTf$ (4.27 mg, 0.0091 mmoL) in methanol (1 mL) was added (S)-2,2'-bis(diphenylphosphino)-1,1'-binaphthyl (6.79 mg, 0.011 mmoL) synthesized in Example 30, and the mixture was stirred at room temperature (25° C.) for 30 min. To a solution of methyl (Z)-α-acetamide cinnamate (0.10 g, 0.456 mmoL) in methanol (4 mL) was added an Rh complex solution prepared in the above for hydrogenation at hydrogen pressure of 1.0 MPa and 25° C. for 24 hrs. The reaction mixture was measured by GC (column: CHIRASIL VAL, 0.25 mm×30 m) to give conversion rate >99.9%, optical purity 15.33% ee (R).

Industrial Applicability

According to the production method of the present invention, compound (I) and a salt thereof useful for the asymmetric synthesis reaction for the production of a compound useful as an optically active pharmaceutical product (e.g., a drug for the prophylaxis or treatment of increased urinary frequency or urinary incontinence, a drug for the prophylaxis or treatment of Alzheimer's disease, a drug for the prophylaxis or treatment of hyperlipidemia etc.) or an intermediate therefor can be produced effectively. The compound (I) and a salt thereof, particularly a complex of an optical isomer thereof with a transition metal shows superior stereoselective rate, chemical yield, catalytic property and the like in the above-mentioned asymmetric synthesis reaction.

The invention claimed is:

1. A production method of a phosphine-borane complex represented by the formula

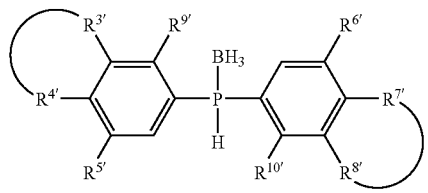

wherein $R^{3'}$, $R^{5'}$, $R^{6'}$ and $R^{8'}$ are each a hydrogen atom, a lower alkyl group or a lower alkoxy group, $R^{4'}$ and $R^{7'}$ are each a fluorine atom, a chlorine atom, a tert-butyl group, a mono-lower alkylamino group or a di-lower alkylamino group, and $R^{9'}$ and $R^{10'}$ are each a hydrogen atom or a lower alkyl group ($R^{3'}$ and $R^{4'}$, and $R^{7'}$ and $R^{8'}$ may form a lower alkylenedioxy group) (provided that $R^{3'}$, $R^{4'}$, $R^{5'}$, $R^{6'}$, $R^{7'}$, $R^{8'}$, $R^{9'}$ and $R^{10'}$ are not hydrogen atoms at the same time), or a salt thereof, which comprises reducing a compound represented by the formula

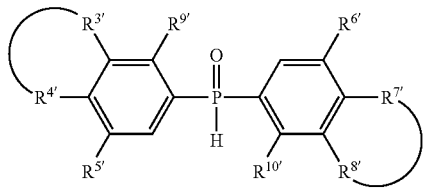

wherein each symbol is as defined above, or a salt thereof, with lithium aluminum hydride in the presence of cerium chloride and sodium borohydride.

2. A phosphine-borane complex represented by the formula

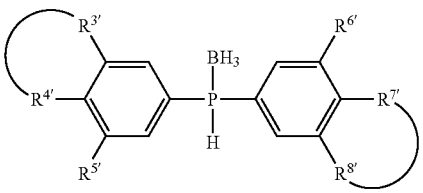

wherein $R^{3'}$, $R^{5'}$, $R^{6'}$ and $R^{8'}$ are each a hydrogen atom, a lower alkyl group or a lower alkoxy group, and $R^{4'}$ and $R^{7'}$ are each a fluorine atom, a chlorine atom, a tert-butyl group, a mono-lower alkylamino group or a di-lower alkylamino group ($R^{3'}$ and $R^{4'}$, and $R^{7'}$ and $R^{8'}$ may each form a lower alkylenedioxy group) (provided that a compound wherein $R^{5'}$ and $R^{6'}$ are hydrogen atoms, and $R^{3'}$ and $R^{4'}$, and $R^{7'}$ and $R^{8'}$ form a methyldioxy group is excluded), or a salt thereof.

* * * * *